US010729767B2

(12) United States Patent
Panicker et al.

(10) Patent No.: US 10,729,767 B2
(45) Date of Patent: Aug. 4, 2020

(54) HUMANIZED ANTI-C1S ANTIBODIES AND METHODS OF INHIBITING C1S CLEAVAGE

(71) Applicant: Bioverativ USA Inc., South San Francisco, CA (US)

(72) Inventors: Sandip Panicker, South San Francisco, CA (US); Graham Parry, South San Francisco, CA (US)

(73) Assignee: Bioverativ USA Inc., Waltham, MA (US)

( * ) Notice: Subject to any disclaimer, the term of this patent is extended or adjusted under 35 U.S.C. 154(b) by 158 days.

(21) Appl. No.: 15/564,904

(22) PCT Filed: Apr. 5, 2016

(86) PCT No.: PCT/US2016/026038
§ 371 (c)(1),
(2) Date: Oct. 6, 2017

(87) PCT Pub. No.: WO2016/164358
PCT Pub. Date: Oct. 13, 2016

(65) Prior Publication Data
US 2018/0092974 A1 Apr. 5, 2018

Related U.S. Application Data

(60) Provisional application No. 62/200,997, filed on Aug. 4, 2015, provisional application No. 62/143,636, filed on Apr. 6, 2015.

(51) Int. Cl.
*A61K 39/395* (2006.01)
*C07K 16/28* (2006.01)
*C07K 16/18* (2006.01)
*A61K 39/00* (2006.01)
*C07K 16/40* (2006.01)

(52) U.S. Cl.
CPC .......... *A61K 39/3955* (2013.01); *C07K 16/18* (2013.01); *C07K 16/28* (2013.01); *A61K 2039/505* (2013.01); *C07K 16/40* (2013.01); *C07K 2317/76* (2013.01); *C07K 2317/90* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,945,039 A | 7/1990 | Suzuki et al. | |
| 6,090,777 A | 7/2000 | Hack et al. | |
| 7,049,282 B2 | 5/2006 | Frank et al. | |
| 7,071,299 B2 | 7/2006 | West et al. | |
| 7,666,627 B2 | 2/2010 | Gal et al. | |
| 7,897,561 B2 | 3/2011 | Kotwal et al. | |
| 7,919,094 B2 | 4/2011 | Schwaeble et al. | |
| 7,923,010 B2 | 4/2011 | Christadoss et al. | |
| 8,071,532 B2 | 12/2011 | Mannesse et al. | |
| 8,148,330 B2 | 4/2012 | Barres et al. | |
| 8,221,756 B2 | 7/2012 | Fung et al. | |
| 8,329,169 B2 | 12/2012 | Fung et al. | |
| 8,415,288 B2 | 4/2013 | Mannesse et al. | |
| 8,501,705 B2 | 8/2013 | Christadoss et al. | |
| 8,545,850 B2 | 10/2013 | Chen et al. | |
| 8,877,197 B2 | 11/2014 | Van Vlasselaer et al. | |
| 8,945,562 B2 | 2/2015 | Van Vlasselaer et al. | |
| 9,074,003 B2 | 7/2015 | Van Vlasselaer et al. | |
| 9,074,004 B2 | 7/2015 | Van Vlasselaer et al. | |
| 9,206,259 B2 | 12/2015 | Van Vlasselaer et al. | |
| 9,512,233 B2 | 12/2016 | Van Vlasselaer et al. | |
| 9,562,092 B2 | 2/2017 | Van Vlasselaer et al. | |
| 9,562,106 B2 | 2/2017 | Van Vlasselaer et al. | |
| 10,450,382 B2 | 10/2019 | van Vlasselaer et al. | |
| 10,457,745 B2 | 10/2019 | van Vlasselaer et al. | |
| 2002/0037915 A1 | 3/2002 | Illig et al. | |
| 2002/0102256 A1 | 8/2002 | West et al. | |
| 2004/0115194 A1 | 6/2004 | Wang | |
| 2004/0219147 A1 | 11/2004 | Bell | |
| 2005/0004031 A1 | 1/2005 | Subasinghe et al. | |
| 2005/0032157 A1 | 2/2005 | Gal et al. | |
| 2005/0079174 A1 | 4/2005 | Barbera-Guillem et al. | |
| 2005/0222027 A1 | 10/2005 | Chiang et al. | |
| 2005/0267035 A1 | 12/2005 | West et al. | |

(Continued)

FOREIGN PATENT DOCUMENTS

| | | | |
|---|---|---|---|
| EP | 2266606 A1 | 12/2010 | |
| JP | 2007-535474 A | 12/2007 | |

(Continued)

OTHER PUBLICATIONS

D'Angelo et al., Many Routes to an Antibody Heavy-Chain CDR3:Necessary, Yet Insufficient, for Specific Binding (Frontiers in Immunology vol. 9, Article 395 Mar. 2018; doi:10.3389/fimmu.2018.00395 (Year: 2018).*

Piche-Nicholas et al., MABS 2018, vol. 10, No. 1, 81-94, doi.org/10.1080/19420862.2017.1389355 (Year: 2018).*

Caldas, C. et al., "Humanization of the anti-CD18 antibody 6.7: an unexpected effect of a framework residue in binding to antigen," *Mol. Immunol.*, 39(15):941-952 (2003) (Elsevier Pub., Cambridge, MA).

Du, J. et al., "Molecular basis of recognition of human osteopontin by 23C3, a potential therapeutic antibody for treatment of rheumatoid arthritis," *J. Mol. Biol.*, 382(4):835-842 (2008), United Kingdom.

(Continued)

*Primary Examiner* — Phillip Gambel
(74) *Attorney, Agent, or Firm* — Wolf, Greenfield & Sacks, P.C.

(57) ABSTRACT

The present disclosure provides humanized anti-C1s antibodies. The present disclosure provides nucleic acids comprising nucleotide sequences encoding the humanized anti-C1s antibodies; and host cells comprising the nucleic acids. The present disclosure provides compositions comprising the humanized anti-C1s antibodies. The present disclosure provides methods of use of the humanized anti-C1s antibodies.

32 Claims, 17 Drawing Sheets

Specification includes a Sequence Listing.

(56) References Cited

U.S. PATENT DOCUMENTS

| | | |
|---|---|---|
| 2005/0271660 A1 | 12/2005 | Wang |
| 2006/0002937 A1 | 1/2006 | Schwaeble et al. |
| 2006/0008883 A1 | 1/2006 | Lazar et al. |
| 2006/0018896 A1 | 1/2006 | Schwaeble et al. |
| 2006/0148015 A1 | 7/2006 | Roos et al. |
| 2007/0172483 A1 | 7/2007 | Schwaeble et al. |
| 2008/0075712 A1 | 3/2008 | Hattori et al. |
| 2008/0160015 A1 | 7/2008 | Gilles et al. |
| 2008/0206242 A1 | 8/2008 | Lawrence et al. |
| 2009/0259019 A1 | 10/2009 | Willis et al. |
| 2009/0269356 A1 | 10/2009 | Epstein et al. |
| 2009/0324585 A1 | 12/2009 | Robinson et al. |
| 2010/0074899 A1 | 3/2010 | Schwaeble et al. |
| 2010/0143343 A1 | 6/2010 | Halstead et al. |
| 2010/0143344 A1 | 6/2010 | Baas et al. |
| 2010/0166862 A1 | 7/2010 | Francois et al. |
| 2011/0002931 A1 | 1/2011 | Tamburini |
| 2011/0020337 A1 | 1/2011 | Schwaeble et al. |
| 2011/0091450 A1 | 4/2011 | Schwaeble et al. |
| 2011/0104156 A1 | 5/2011 | Christadoss et al. |
| 2011/0190221 A1 | 8/2011 | Francois et al. |
| 2011/0281757 A1 | 11/2011 | Tyan et al. |
| 2011/0311549 A1 | 12/2011 | Schwaeble et al. |
| 2011/0312505 A1 | 12/2011 | Reddy et al. |
| 2012/0195880 A1 | 8/2012 | Barres et al. |
| 2012/0225056 A1 | 9/2012 | Rother et al. |
| 2012/0230953 A1 | 9/2012 | Goldenberg et al. |
| 2012/0244139 A1 | 9/2012 | Madison et al. |
| 2012/0251549 A1 | 10/2012 | Fung et al. |
| 2012/0258095 A1 | 10/2012 | Demopulos et al. |
| 2012/0263717 A1 | 10/2012 | Dennis et al. |
| 2012/0282263 A1 | 11/2012 | Dudler et al. |
| 2012/0308566 A1 | 12/2012 | Martin et al. |
| 2012/0309943 A1 | 12/2012 | Kumada et al. |
| 2012/0315266 A1 | 12/2012 | Olson et al. |
| 2012/0328601 A1 | 12/2012 | Barres et al. |
| 2013/0064820 A1 | 3/2013 | Magro |
| 2013/0078245 A1 | 3/2013 | Holers et al. |
| 2013/0123473 A1 | 5/2013 | Goldenberg et al. |
| 2013/0202612 A1 | 8/2013 | Lin et al. |
| 2013/0203678 A1 | 8/2013 | Francois et al. |
| 2013/0224187 A1 | 8/2013 | Rother et al. |
| 2013/0237589 A1 | 9/2013 | Benedict et al. |
| 2013/0244941 A1 | 9/2013 | Mannesse et al. |
| 2013/0259860 A1 | 10/2013 | Smith et al. |
| 2013/0261287 A1 | 10/2013 | Sabbadini et al. |
| 2013/0273052 A1 | 10/2013 | Gies et al. |
| 2014/0127208 A1 | 5/2014 | Van Vlasselaer et al. |
| 2014/0140933 A1 | 5/2014 | Van Vlasselaer et al. |
| 2015/0329645 A1 | 11/2015 | van Vlasselaer et al. |
| 2016/0159890 A1 | 6/2016 | Rosenthal et al. |
| 2017/0226229 A1 | 8/2017 | Van Vlasselaer et al. |
| 2017/0226230 A1 | 8/2017 | Van Vlasselaer et al. |
| 2018/0169240 A1 | 6/2018 | Parry et al. |

FOREIGN PATENT DOCUMENTS

| | | |
|---|---|---|
| JP | 2008-533156 A | 8/2008 |
| JP | 2013-136530 A | 7/2013 |
| JP | 6538561 B2 | 7/2019 |
| WO | WO-0157079 A2 | 8/2001 |
| WO | WO-03009803 A2 | 2/2003 |
| WO | WO-2006101860 A1 | 9/2006 |
| WO | WO-2008074227 A1 | 6/2008 |
| WO | WO 2012/028622 A2 | 3/2012 |
| WO | WO-2013093027 A1 | 6/2013 |
| WO | WO-2014066744 A2 | 5/2014 |
| WO | WO-2014071206 A2 | 5/2014 |
| WO | WO 2015/084999 A1 | 6/2015 |
| WO | WO-2016164358 A1 | 10/2016 |
| WO | WO-2016210172 A1 | 12/2016 |
| WO | WO 2018/071676 A1 | 4/2018 |
| WO | WO 2018/170145 A1 | 9/2018 |

OTHER PUBLICATIONS

Foote, J. et al., "Antibody framework residues affecting the conformation of the hypervariable loops," *J. Mol. Biol.* 224:487-499, Elsevier, Netherlands (1992) (Elsevier Pub., Cambridge, MA).

[No Author Listed] True North Therapeutics: Study NCT02502903. Jul. 14, 2016 (v3). Retrieved from the Internet: https://clinicaltrials.gov/ct2/history/NCT02502903?V_1=View#StudyPageTop on May 23, 2018. 7 pages.

D'Angelo et a., Many Routes to an Antibody Heavy-Chain CDR3: Necessary, Yet Insufficient, for Specific Binding. Front Immunol. Mar. 8, 2018;9:395. doi: 10.3389/fimmu.2018.00395. eCollection 2018.

Derhaschnig et al., Combined integrated protocol/basket trial design for a first-in-human trial. Orphanet J Rare Dis. Oct. 4, 2016;11(1):134.

Jaeger et al., Therapeutic Rationale and Clinical Development of TNT009, an Upstream Classical Pathway Inhibitor, for Cold Agglutinin Disease. Blood. 2015;126:3560. Retrieved from the Internet: http://www.bloodjournal.org/content/126/23/3560. 7 pages.

Jilma et al., Chronic Inhibition of Complement C1s by TNT009 Produces Sustained, Complete Remission in Patients with Severe, Transfusion-Dependent Cold Agglutinin Disease (CAD). Blood. 2016;128:2435. Retrieved from the Internet: http://www.bloodjournal.org/content/128/22/2435 on Apr. 9, 2019. 8 pages.

Moore et al., Engineered Fc variant antibodies with enhanced ability to recruit complement and mediate effector functions. MAbs. Mar.-Apr. 2010; 2(2):181-9.

Mühlbacher et al., Blockade of HLA Antibody-Triggered Classical Complement Activation in Sera From Subjects Dosed With the Anti-C1s Monoclonal Antibody TNT009-Results from a Randomized First-in-Human Phase 1 Trial. Transplantation. Oct. 2017;101(10):2410-2418. doi: 10.1097/TP.0000000000001804.

Panicker et al., TNT009 Prevents Erythrocyte C3 Fragment Opsonization and Rescues Reticulocytes from Destruction in Patients with Cold Agglutinin Disease. Blood. 2016;128:94. Retrieved from the Internet: http://www.bloodjournal.org/content/128/22/94 on Apr. 9, 2019. 7 pages.

Almagro, J.C. and Fransson, J., "Humanization of Antibodies," Frontiers in Bioscience 13:1619-1633, Frontiers in Bioscience Publications, United States (2008).

An, Z., et al., "IgG2m4, an Engineered Antibody Isotype with Reduced Fc function," Mabs 1(6):572-579, Philadelphia, PA: Taylor & Francis, United States (Nov.-Dec. 2009).

Anti-Complement C1 s Antibody, Cat# LS-C121168, LifeSpan Biosciences, accessed at http://www.lsbio.com/antibodies/anti-complement-c1s-antibody-mouse-anti-human-monoclonal-for-ihc-western-blot-ls-c121168/124626, 2014.

Anti-Complement C1 s Antibody, Cat# LS-C6208, LifeSpan Biosciences, accessed at http://www.lsbio.com/antibodies/anticomplement-c1s-antibody-mouse-anti-human-monoclonal-ls-c6208/6949, 2014.

Anti-Complement C1 s Antibody [clone 2011], Cat# LS-C173719, LifeSpan Biosciences, accessed at http://www.lsbio.com/antibodies/anti-complement-c1s-antibody-clone-2d11-mouse-anti-humanmonoclonal-for-ihc-western-blot-ls-c173719/181143, 2014.

Anti-Complement C1 s Antibody [clone 2A8], Cat# LS-C173720, LifeSpan Biosciences, accessed at http://www.lsbio.com/antibodies/anti-complement-c1s-anti body-clone-2a8-mouse-anti-human-monoclonal-for-ihewestern-blot-ls-c173720/181144, 2014.

Anti-Complement C1 s Antibody [clone 2F5], Cat# LS-C173425, LifeSpan Biosciences, accessed at http://www.lsbio.com/antibodies/anti-complement-c1s-antibody-ciane-2f5-mouse-anti-human-monoclonalfor-western-blot-ls-c173425/180849, 2014.

Anti-Complement C1 s Antibody [clone 401 0], Cat# LS-C173540, LifeSpan Biosciences, accessed at http://www.lsbio.com/anti bodies/anti-complement-c1s-antibody-clone-4d10-mouse-anti-human-monoclonal-for-westernblot-ls-c173540/180964, 2014.

Anti-Complement C1 s Antibody [clone 409], Cat# LS-C173424, LifeSpan Biosciences, accessed at http://www.lsbio.com/antibodies/anti-complement-c1s-antibody-ciane-4d9-mouse-anti-human-monoclonalfor-western-blot-ls-c173424/180848, 2014.

(56) References Cited

OTHER PUBLICATIONS

Anti-Complement C1 s Antibody [clone 49], Cat# LS-C6209, LifeSpan Biosciences, accessed at http://www.lsbio.com/antibodies/anti-complement-c1s-antibody-ciane-49-mouse-anti-human-monoclonalls-c6209/6950, 2014.

Anti-Complement C1 s Antibody [clone 5F2], Cat# LS-C173718, LifeSpan Biosciences, accessed at http://www.lsbio.com/antibodies/anti-complement-c1s-anti body-clone-5f2-mouse-anti-human-monoclonal-for-ihc-western-blot-ls-c173718/181142, 2014.

Anti-Complement C1s Antibody (aa1-688), Cat# LS-C128271, LifeSpan Biosciences, accessed at http://www.lsbio.com/antibodies/anti-complement-c1s-antibody-aa1-688-mouse-anti-human-polyclonal-for-western-blot-ls-c128271/131891, 2014.

Anti-Complement C1s Antibody [clone M81], Cat# LS-C140039, accessed at LifeSpan Biosciences, accessed at http://www.lsbio.com/antibodies/anti-complement-c1s-antibody-clone-m81-mouse-anti-human-monoclonal-for-ihc-western-blot-ls-c140039/144752, 2014.

Anti-Complement C1s Antibody (Internal) [clone EPR9066(B)], Cat# LS-C154717, LifeSpan Biosciences, accessed at http://www.lsbio.com/antibodies/anti-complement-c1s-antibody-internal-clone-epr9066b-rabbit-anti-human-monoclonal-for-ihc-western-blot-ls-c154717/161392, 2014.

Anti-Complement C1s Antibody (Internal) [clone EPR9067(B)], Cat# LS-C154704, LifeSpan Biosciences, accessed at http://www.lsbio.com/antibodies/anti-complement-c1s-antibody-internal-clone-epr9067b-rabbit-anti-human-monoclonal-for-western-blot-ls-c154704/161379, 2014.

Basiglio, C.L., et al., "Complement Activation and Disease: Protective Effects of Hyperbilirubinaemia," Clinical Science 118(2):99-113, London : Portland Press on behalf of the Medical Research Society and the Biochemical Society, England (Oct. 2009).

Brahmi, Z., et al., "Synergistic Inhibition of Human Cell-Mediated Cytotoxicity by Complement Component Antisera Indicates That Target Cell Lysis May Result From an Enzymatic Cascade Involving Granzymes and Perforin," Nature Immunology 14(5-6):271-285, New York : S. Karger, Switzerland (Sep. 1995).

Carroll, S., et al., "Antibody-Mediates Inhibition of Human C1s and the Classical Complement Pathway," Immunobiology 218(8):1041-1048, Amsterdam : Elsevier, Netherlands (Aug. 2013).

Carroll., "Strategies for Generating Therapeutic Antibodies," Dissertation, The University of Texas at Austin, 170 pages (Aug. 2012).

Chen, C., et al., "Enhancement and Destruction of Antibody Function by Somatic Mutation: Unequal Occurrence Is Controlled by V Gene Combinatorial Associations," The EMBO Journal 14(12):2784-2794, Wiley Blackwell, England (1995).

Colman, P.M., "Effects of Amino Acid Sequence Changes on Antibody-antigen Interactions," Research in Immunology 145(1):33-36, Elsevier, France (Jan. 1994).

Gal, P., et al., "C1s, the Protease Messenger of C1. Structure, Function and Physiological Significance," Immunobiology 205(4-5):383-394, Amsterdam : Elsevier, Netherlands (Sep. 2002).

Gal, P., et al., "Early Complement Proteases: C1r, C1s and MASPs. A Structural Insight into Activation and Functions," Molecular Immunology 46(14):2745-2752, Elmsford, N. Y., Pergamon Press, England (May 2009).

Hamad, I., et al., "Complement Activation by PEGylated Single-Walled Carbon Nanotubes Is Independent of C1q and Alternative Pathway Turnover," Molecular Immunology 45(14):3797-3803, Elmsford, N. Y., Pergamon Press, England (Aug. 2008 ).

Heinz, H.P., et al., "Monoclonal Antibodies Against Components of the Classical Pathway of Complement," Complement and Inflammation 6(3):166-174, New York : Karger, Switzerland (1989).

Kidmose, R.T., et al., "Structural Basis for Activation of the Complement System by Component C4 Cleavage," Proceedings of the National Academy of Sciences 109(38):15425-15430, Washington, DC : National Academy of Sciences, United States (Sep. 2012).

Kussie, P.H., et al., "A Single Engineered Amino Acid Substitution Changes Antibody Fine Specificity," Journal of Immunology 152(1):146-152, American Association of Immunologists, United States (1994).

Matsumoto, M., et al., "Acceleration of Site-To-Site Transfer of C1-by a Monoclonal Antibody to C1-s ," Molecular Immunology 26(8):697-703, Oxford, Elmsford, N. Y., Pergamon Press, England (Aug. 1989).

Matsumoto, M., et al., "Functional Analysis of Activated C1s, a Subcomponent of the First Component of Human Complement, by Monoclonal Antibodies," Journal of Immunology 137(9):2907-2912, Baltimore : Williams & Wilkins, United States (Nov. 1986).

Matsumoto, M., et al., "Probing the C4-Binding Site on C1s with Monoclonal Antibodies. Evidence for a C4/C4b-Binding Site on the Gamma-Domain," Journal of Immunology 142(8):2743-2750, Baltimore : Williams & Wilkins, United States (Apr. 1989).

Nagaki, K., et al., "Specific Antisera to C1s: Detection of Different Electrophoretic Species of C1s," Journal of Immunology 103(1):141-145, Baltimore : Williams & Wilkins, United States (Jul. 1969).

Nakagawa, K., et al., "Complement C1s Activation in Degenerating Articular Cartilage of Rheumatoid Arthritis Patients: Immunohistochemical Studies With an Active Form Specific Antibody," Annals of the Rheumatic Diseases 58(3):175-181, London : BMJ, England (Mar. 1999).

Nakagawa, K., et al., "Coordinated Change Between Complement C1s Production and Chondrocyte Differentiation In Vitro," Cell and Tissue Research 289(2):299-305, Berlin, New York, Springer-Verlag, Germany (Aug. 1997).

Phuan, P.W., et al., "C1q-targeted Monoclonal Antibody Prevents Complement-Dependent Cytotoxicity and Neuropathology in in Vitro and Mouse Models of Neuromyelitis Optica," Acta Neuropathologica 125(6):829-840, Berlin : Springer Verlag, Germany (Jun. 2013).

Reddy M.P., et al., "Elimination of Fc Receptor-Dependent Effector Functions of a Modified IgG4 Monoclonal Antibody to Human CD4," Journal of Immunology 164(4):1925-1933, American Association of Immunologists, United States (2000).

Rossi, V., et al., "Baculovirus-mediated Expression of Truncated Modular Fragments from the Catalytic Region of Human Complement Serine Protease C1s. Evidence for the Involvement of Both Complement Control Protein Modules in the Recognition of the C4 Protein Substrate," Journal of Biological Chemistry 273(2):1232-1239, Baltimore, MD : American Society for Biochemistry and Molecular Biology, United States (Jan. 1998).

Rudikoff, S., et al., "Single Amino Acid Substitution Altering Antigen-binding Specificity," Proceedings of the National Academy of Sciences of the United States of America 79(6):1979-1983, National Academy of Sciences, Washington (Mar. 1982).

Sakiyama, H., et al., "Biochemical Characterization and Tissue Distribution of Hamster Complement C1s," Journal of Immunology 46(1):183-187, Bethesda, MD : American Association of Immunologists, United States (Jan. 1991).

Sakiyama, H., et al., "Complement C1s, a Classical Enzyme with Novel Functions at the Endochondral Ossification Center: Immunohistochemical Staining of Activated C1s with a Neoantigen-Specific Antibody," Cell and Tissue Research 288(3):557-565, Berlin, New York, Springer-Verlag, Germany (Jun. 1997).

Sakiyama, H., et al., "Site-Directed Mutagenesis of Hamster Complement C1s: Characterization with an Active Form-Specific Antibody and Possible Involvement of C1S in Tumorigenicity," International Journal of Cancer 66(6):768-771, New York, NY : Wiley-Liss, United States (Jun. 1996).

Thielens, N.M., et al., "Comparative Study of the Fluid-Phase Proteolytic Cleavage of Human Complement Subcomponents C4 and C2 by C1s and C1r2-C1s2," FEBS Letters 165(1):111-116, West Sussex : John Wiley & Sons Ltd, England (Jan. 1984).

Tseng, Y., et al., "Probing the Structure of C1 with an Anti-C1s Monoclonal Antibody: The Possible Existence of Two Forms of C1 in Solution," Molecular Immunology 34(8-9):671-679, Oxford, Elmsford, N. Y., Pergamon Press, England (Jun. 1997).

Veerhuis, R., et al., "Early Complement Components in Alzheimer's Disease Brains," Acta Neuropathologica 91(1):53-60, Berlin : Springer Verlag, Germany (1996).

Wines, B.D., et al., "The IgG Fc Contains Distinct Fc Receptor (FcR) Binding Sites: The Leukocyte Receptors Fc Gamma RI and Fc Gamma RIIa Bind to a Region in the Fc Distinct from that Recognized by Neonatal FcR and Protein A," Journal of Immunol-

(56) References Cited

OTHER PUBLICATIONS ogy 164(10):5313-5318, Bethesda, MD : American Association of Immunologists, United States (May 2000).

Brown et al., Tolerance of single, but not multiple, amino acid replacements in antibody VH CDR 2: a means of minimizing B cell wastage from somatic hypermutation? J Immunol. May 1, 1996;156(9):3285-91.

Angal et al., A single amino acid substitution abolishes the heterogeneity of chimeric mouse/human (IgG4) antibody. Mol Immunol. Jan. 1993;30(1):105-8.

Fitzpatrick et al., An open label clinical trial of complement inhibition in multifocal motor neuropathy. J Peripher Nerv Syst. Jun. 2011;16:84-91.

Hinson et al., Prediction of Neuromyelitis Optica Attack Severity by Quantitation of Complement-Mediated Injury to Aquaporin-4-Expressing Cells. Arch Neurol. Sep. 2009;66(9):1164-7.

Iwata et al., Bullous pemphigoid: role of complement and mechanisms for blister formation within the lamina lucida. Exp Derm. May 7, 2013;22:381-5.

Kusner et al., Effect of complement and its regulation on myasthenia gravis pathogenesis. Expert Rev Clin Immunol. Jan. 2008;4(1):43-52.

Piche-Nicholas et al., Changes in complementarity-determining regions significantly alter IgG binding to the neonatal Fc receptor (FcRn) and pharmacokinetics. MAbs. Jan. 2018;10(1):81-94. doi: 10.1080/19420862.2017.1389355. Epub Nov. 3, 2017.

Ricklin et al., Complement in Immune and Inflammatory Disorders: Pathophysiological Mechanisms, Apr. 15, 2013;190(8):3831-8.

Sethi et al., Membranoproliferative Glomerulonephritis and C3 Glomerulopathy: Resolving the Confusion. Kidney Int. Mar. 2012;81(5):434-441.

Shi et al., TNT003, an inhibitor of the serine protease C1s, prevents complement activation induced by cold agglutinins. Blood. Jun. 26, 2014;123(26):4015-22. doi: 10.1182/blood-2014-02-556027. Epub Apr. 2, 2014.

Strobel et al., Hemolytic Transfusion Reactions. Transfus Med Hemother. Sep. 18, 2008;35:346-353.

Susuki et al., Anti-GM1 antibodies cause complement-mediated disruption of sodium channel clusters in peripheral motor nerve fibers. J Neurosci. Apr. 11, 2007;27(15):3956-67.

Tichaczek-Goska, Deficiencies and Excessive Human Complement System Activation in Disorders of Multifarious Etiology. Adv Clin Exp Med. Jan.-Feb. 2012;21(1):105-14.

\* cited by examiner

Figure 1
VH Variant 1

```
        10         20         30         40         50         60         70         80         90        100
GAGGTTCAGCTGGTGCAGTCTGGGGCTGAGGTTAAGAAGCCTAAGGCTTAAGGGCCTCAGTCAAGTTGTCCTGCACAGCTTCTGGCTTTAACATTAAAGGACTATA
 E  V  Q  L  V  Q  S  G  A  E  L  K  K  P  G  A  S  V  K  L  S  C  T  A  S  G  F  N  I  K  D  Y
                                    10                   20                   30
       110        120        130        140        150        160        170        180        190        200
TACACTGGGTGAAGCAGAGGCCTGGACAGGGCCTGGAGTGGATTGGAAGGATTGATCCTGAGGATGGTGAAACTAAATATGCCCCGAAGTTCCAAGGAAAGGTCAA
 I  H  W  V  K  Q  A  P  G  Q  G  L  E  W  I  G  R  I  D  P  A  D  G  H  T  K  Y  A  P  K  F  Q  G  K
                40                          50      52 a  b  c        60
       210        220        230        240        250        260        270        280        290        300
GGCCACTATAACTGCAGACACATCCAACACAGCCTACCTGCAGCTCAGCAGCCTGACATCTGAGGACACTGCCGTCTATTACTGTGCTAGATATGGT
 A  T  I  T  A  D  T  S  N  T  A  Y  L  Q  L  S  S  L  T  S  E  D  T  A  V  Y  Y  C  A  R  Y  G
                70                82 a  b  c           80                                90
       310        320        330        340        350
TAGGGGAGGGGTCTTTGACTACTGGGGCCAAGGCACCACTGTCACAGTCTCCTCA
 Y  G  E  V  F  D  Y  W  G  Q  G  T  T  V  T  V  S  S
        100 a  b                  110              113
```

CDR definitions and protein sequence numbering according to Kabat. CDR nucleotide and protein sequences are highlighted in red.

Figure 2
VH Variant 2

```
         10         20         30         40         50         60         70         80         90        100
GAGGTTCAGCTGGTGCAGTCTGGGGCTGAGGTGAAGAAGCCAGGGGCCTCAGTCAAGGTTGTCTGCACAGCTTCTGGCTTTAACATTAAAGACGACTATA
 E  V  Q  L  V  Q  S  G  A  E  V  K  K  P  G  A  S  V  K  V  S  C  T  A  S  G  F  N  I  K  D  D  Y
                                 10                        20                        30

110        120        130        140        150        160        170        180        190        200
TACACTGGGTGAAGCAGGCCCCTGGACAAGGGCCTGGAGTGGATTGGAAGGATTGATCCTGCGAATGGTGATACTAAATATGCCCCGAAGTTCCAAGTCAA
 I  H  W  V  K  Q  A  P  G  Q  G  L  E  W  I  G  R  I  D  P  A  N  G  D  T  K  Y  A  P  K  F  Q  V  K
              40                        50       52 a b c                 60

210        220        230        240        250        260        270        280        290        300
GGGCACTATAACTGCAGACACATCCAGCAACACAGCCTACCTGGAACTTAGCAGCCTGAGATCTGAGGACACTGCCGTCTATTACTGTGCTAGATATGGT
 G  T  I  T  A  D  T  S  S  N  T  A  Y  L  E  L  S  S  L  R  S  E  D  T  A  V  Y  Y  C  A  R  Y  G
                     70                        80  82 a b c                   90

310        320        330        340        350
TACGGAAGGGAGGTGTTTGACTACTGGGGCCAAGGCACCACTGTCACAGTCTCCTCA
 Y  G  R  E  V  F  D  Y  W  G  Q  G  T  T  V  T  V  S  S
         100 a b               110                113
```

CDR definitions and protein sequence numbering according to Kabat. CDR nucleotide and protein sequences are highlighted in red.

Figure 3
VH Variant 3

```
         10         20         30         40         50         60         70         80         90        100
CAGGTTCAGCTGGTGCAGTCTGGGGCTGAGGTGAAGAAGCCAGGGGCCTCAGTCAAGGTTGTCCTGCAAGCTTCTGGCTTAACATTAAAGAGGACTATA
 Q  V  Q  L  V  Q  S  G  A  E  V  K  K  P  G  A  S  V  K  V  S  C  T  A  S  G  F  N  I  K  D  Y
              1                   10                  20                  30

110        120        130        140        150        160        170        180        190        200
TACACTGGGTGAAGCAGGCCCCTGGACAAGGGCTTGGAGTGGATTGGAAGGATTGATCCTGCAGATGGTAATACTAAATATGATCCGAAGTTCCAGGTCAA
 I  H  W  V  K  Q  A  P  G  Q  G  L  E  W  I  G  R  I  D  P  A  D  G  N  T  K  Y  A  P  K  F  Q  V  K
              40                  50       52 a  b  c          60

210        220        230        240        250        260        270        280        290        300
AGTCACTATAACTGCAGACACATCCACCAGCACAGCCTACCTGGAGCTGAGCAGCCTGAGATCTGAAGACACTGCGGTCTATTACTGTGCTAGATATGGT
 V  T  I  T  A  D  T  S  T  S  T  A  Y  L  E  L  S  S  L  R  S  E  D  T  A  V  Y  Y  C  A  R  Y  G
              70                  80       82 a  b  c          90

310        320        330        340        350
TACGGGGAGGGAGGTCTTTGACTACTGGGGCCAAGGCACCACTGTCACAGTCTCCTCA
 Y  G  E  G  G  L  D  Y  W  G  Q  G  T  T  V  T  V  S  S
                  100 a  b                   110       113
```

CDR definitions and protein sequence numbering according to Kabat. CDR nucleotide and protein sequences are highlighted in red.

Figure 4
VH Variant 4

```
         10          20          30          40          50          60          70          80          90         100
CAGGTTCAGCTGGTGCAGTCTGGGGCTGAGGTGAAGAAGCCAGGGGCCTCAGTCAAGGTCTCCTGCACAGCTTCTGGCTTTAACATTAAAGACGAGTATA
 Q  V  Q  L  V  Q  S  G  A  E  V  K  K  P  G  A  S  V  K  V  S  C  T  A  S  G  F  N  I  K  D  E  Y
                                 10                          20                          30

110         120         130         140         150         160         170         180         190         200
TACACTGGGTGCGCCAGGCCCCTGGACAAGGGCTTGAGTGGATTGGAAGGATTGATCCTGCGAATGGTAATACTAAATATGCCCCGAAGTTCCAAGGTAAA
 Y  H  W  V  R  Q  A  P  G  Q  G  L  E  W  I  G  R  I  D  P  A  N  G  N  T  K  Y  A  P  K  F  Q  G  K
                 40                          50  52 a  b  c                          60

210         220         230         240         250         260         270         280         290         300
AGTCACTATAACTGGAGACACATCCACCAGCACCTACATGGAGCTGAGCAGCCTGAGATCTGAGGACACTGCCGTCTATTACTGTGCTAGAGATGGT
 S  H  Y  N  W  R  H  I  H  Q  H  L  H  G  A  E  Q  P  E  I  *  G  H  C  R  L  L  L  V  L  E  M
                         70                          80 82 a  b  c                          90

310         320         330         340         350
TAGGGAGGAGGTCTTTGATTACTGGGGCCAAGGCACCACTGTCACAGTCTCCTCA
 *  G  G  G  L  *  L  L  G  P  R  H  H  C  H  S  L  L
         100 a  b                     110         113
```

CDR definitions and protein sequence numbering according to Kabat. CDR nucleotide and protein sequences are highlighted in red.

Figure 5
VH Variant 5

```
         10          20          30          40          50          60          70          80          90         100
CAGGTTCAGCTGGTGCAGTCTGGGGCTGAGGTGAAGAAGCCAGGGGCCTCAGTGAAGGTCTCCTGCGAAGCTTCTGGCTTTAACATTAAAGACGACTATA
 Q  V  Q  L  V  Q  S  G  A  E  V  K  K  P  G  A  S  V  K  V  S  C  A  A  S  G  F  N  I  K  D  D  Y
                         10                          20                          30

110         120         130         140         150         160         170         180         190         200
TAGACTGGGTGCGCCAGGCCCCTGGACAAGGGCCTGGAGTGGATGGGACTTGGAAAGGATTGATCCTGCTGATGGTGATACTAAATATGCCCCGAAGTTCCAAGTCAA
 I  D  W  V  R  Q  A  P  G  Q  G  L  E  W  I  G  R  I  D  P  A  D  G  D  T  K  Y  A  P  K  F  Q  V  K
                         40                          50   52 a b c                  60

210         220         230         240         250         260         270         280         290         300
AGTCACTATAACTGCAGACACATCCACAAGCACCAGCCTACATGGAGCTGAGCAGCCTGAGATCTGAGGACACTGCCGTGTATTACTGTGCTAGATATGGT
 V  T  I  T  A  D  T  S  T  S  T  A  Y  M  E  L  S  S  L  R  S  E  D  T  A  V  Y  Y  C  A  R  Y  G
                         70                    80  82 a b c                          90

310         320         330         340         350
TACGGGACGGAGTGTTTGACTACTGGGGCCAAGGCACCACTGTCACAGTCTCCTCA
 Y  G  R  E  C  L  T  T  G  G  Q  G  T  T  V  T  V  S  S
             100 a b                          110      113
```

CDR definitions and protein sequence numbering according to Kabat. CDR nucleotide and protein sequences are highlighted in red.

Figure 6
VK Variant 1

```
         10          20          30          40          50          60          70          80          90         100
GACATTGTGCTGACCCAATCTCCAGACTCTTTGGCTGTGTCTCTCGGGGAGAGGGCCACCATCTCCTGCAAGGCCAGCCAAAGTGTTGATTATGATGGTG
 D  I  V  L  T  Q  S  P  D  S  L  A  V  S  L  G  E  R  A  T  I  S  C  K  A  S  Q  S  V  D  Y  D  G
                        10                      20                          27a b c d 110         120         130         140         150         160         170         180         190         200
ATAGTTATATGAACTGGTACCAACAGAAAACAGGACAGCCACCCAAACTCCTCATTTATGCAGCAAATCCTTATTATGGAGTGCCAGCAAGGTTTAG
 D  S  Y  M  N  W  Y  Q  Q  K  T  G  Q  P  P  K  L  L  I  Y  A  A  S  N  L  E  S  G  I  P  A  R  F  S
 30                     40                          50                          60

210         220         230         240         250         260         270         280         290         300
TGGCAGTGGGTCTGGGACAGACTTCACCCTCACCATCAGCAGCCTGGAGGAGGAGGATTTTGCAATCTATTACTGTCAGCAAAGTAATGAAGATCCTTGG
 G  S  G  S  G  T  D  F  T  L  T  I  S  S  L  E  E  E  D  F  A  I  Y  Y  C  Q  Q  S  N  E  D  P  W
                    70                          80                          90

310         320         330
ACGTTCGGTGGAGGCACCAAGGTGGAAATCAAA
 T  F  G  G  G  T  K  V  E  I  K
                    100         108a
```

CDR definitions and protein sequence numbering according to Kabat CDR nucleotide and protein sequences are highlighted in red.

Figure 7
VK Variant 2

```
         10         20         30         40         50         60         70         80         90        100
GACATTGTGCTGACCCAATCTCCAGACTCTTTGGCTGTGTCTCTCGGGGAGAGGGCCACCATCTCCTGCAAGGCCAGCCAAAGTGTTGATTATGATGGTG
 D  I  V  L  T  Q  S  P  D  S  L  A  V  S  L  G  E  R  A  T  I  S  C  K  A  S  Q  S  V  D  Y  D  G
              10                      20                      27 a b c d 110        120        130        140        150        160        170        180        190        200
ATAGTTATATGAACTGGTACCAACAAAAACCAGGACAGCCACCCAAACTCCTCATTTATGCTGCATCCAATTTGGAATCTGGCATCCCAGCCAGGTTTAG
 D  S  Y  M  N  W  Y  Q  Q  K  P  G  Q  P  P  K  L  L  I  Y  A  A  S  N  L  E  S  G  I  P  A  R  F
    30                     40                              50                            60

210        220        230        240        250        260        270        280        290        300
TGGCAGTGGGTCTGGGACAGACTTCACCCTCACCATCAGCAGCCTGGAGCCTGAGGATTTTGCAATCTATTACTGTCAACAAAGTAATGAAGACCCGTGG
 S  G  S  G  T  D  F  T  L  T  I  S  S  L  E  P  E  D  F  A  I  Y  Y  C  Q  Q  S  N  E  D  P  W
               70                         80                              90

310        320        330
ACGTTCGGTGGAGGCACCAAGGTGGAAATCAAA
 T  F  G  G  G  T  K  V  E  I  K
          100                  106 a
```

CDR definitions and protein sequence numbering according to Kabat. CDR nucleotide and protein sequences are highlighted in red.

Figure 8
VK Variant 5

```
         10         20         30         40         50         60         70         80         90        100
GACATTGTGCTGACCCAATCTCCAGACTCTTTGGCTGTGTCTCTCGGGGAGAGGGCCACCATCTCCTGCAAGGCCAGCCAAAGTGTTGATTATGATGGTG
 D  I  V  L  T  Q  S  P  D  S  L  A  V  S  L  G  E  R  A  T  I  S  C  K  A  S  Q  S  V  D  Y  D  G
                     10                  20                  30               27 a b c d 110        120        130        140        150        160        170        180        190        200
ATAGTTATATGAATTGGTACCAACAAAAACCAGGACAGCCACCCAAACTCCTCATTTATGATGCATCGAATTTGGAATCTGGCATCCCAGCCAGGTTTAG
  S  Y  M  N  W  Y  Q  Q  K  P  G  Q  P  P  K  L  L  I  Y  D  A  S  N  L  E  S  G  I  P  A  R  F  S
 30                  40                  50                  60

210        220        230        240        250        260        270        280        290        300
TGGCAGTGGGTCTGGGACAGACTTCACCCTCACCATCAGCAGCCTGGAGCCTGAAGATTTTGCAGTCTATTACTGTCAGCAAAGTAATGAAGACCCGTGG
  G  S  G  S  G  T  D  F  T  L  T  I  S  S  L  E  P  E  D  F  A  V  Y  Y  C  Q  Q  S  N  E  D  P  W
                     70                  80                  90

310        320        330
ACGTTCGGTGGAGGCACCAAGGTGGAAATCAAA
  T  F  G  G  G  T  K  V  E  I  K
              100            106 a
```

CDR definitions and protein sequence numbering according to Kabat. CDR nucleotide and protein sequences are highlighted in red.

Figure 9 – Table 2: VH Variants

| Amino Acid Position | TNT005 (Parental Antibody) | VH Variant 1 | VH Variant 2 | VH Variant 3 | VH Variant 4 | VH Variant 5 |
|---|---|---|---|---|---|---|
| 1 | E | E | E | Q | Q | Q |
| 5 | Q | V | V | V | V | V |
| 11 | L | L | V | V | V | V |
| 12 | V | K | K | K | K | K |
| 13 | R | K | K | K | K | K |
| 20 | L | L | L | L | V | V |
| 23 | T | T | T | T | T | A |
| 38 | K | K | K | K | R | R |
| 40 | R | A | A | A | A | A |
| 42 | E | G | G | G | G | G |
| 67 | A | A | A | V | V | V |
| 75 | S | T | T | T | T | T |
| 76 | N | N | N | S | S | S |
| 80 | L | L | L | L | M | M |
| 81 | Q | Q | E | E | E | E |
| 83 | E | T | R | R | R | R |
| 109 | L | V | V | V | V | V |

Figure 10

Table 3: VK Variants

| Amino Acid Position | TNT005 (Parental Antibody) | VK Variant 1 | VK Variant 2 | VK Variant 5 |
|---|---|---|---|---|
| 9 | A | D | D | D |
| 17 | Q | E | E | E |
| 40 | T | T | P | P |
| 46 | I | I | I | I |
| 74 | N | T | T | T |
| 76 | H | S | S | S |
| 77 | P | S | S | S |
| 78 | V | L | L | L |
| 80 | E | E | P | P |
| 83 | A | F | F | F |
| 85 | I | I | I | V |
| 104 | L | V | V | V |

Figure 11
Table 4

| antibody | Direct Binding Ab to aC1s EC50 (M) | Competition Binding w/ 50pM Biot-005 IC50 (M) | Classical Pathway Inhibition IC50 (M) |
|---|---|---|---|
| TNT005.001 | 5.586E-11 | 3.952E-11 | 1.061E-09 |
| biotin-TNT005.001 | 8.28E-11 | Not Tested | Not Tested |
| humanized VH1/Vk1 | 2.007E-10 | 1.238E-10 | 1.2E-09 |
| humanized VH1/Vk2 | 8.797E-11 | 5.566E-11 | 1.137E-09 |
| humanized VH1/Vk5 | 1.074E-10 | 1.288E-10 | 1.257E-09 |
| humanized VH2/Vk1 | 1.374E-10 | 1.44E-10 | 1.234E-09 |
| humanized VH2/Vk2 | 1.335E-10 | 1.576E-10 | 1.259E-09 |
| humanized VH2/Vk5 | 1.239E-10 | 1.678E-10 | 1.272E-09 |
| humanized VH3/Vk1 | 1.68E-10 | 1.79E-10 | 1.27E-09 |
| humanized VH3/Vk2 | 1.63E-10 | 1.83E-10 | 1.26E-09 |
| humanized VH3/Vk5 | 1.38E-10 | 1.58E-10 | 1.38E-09 |
| humanized VH4/Vk1 | 1.52E-10 | 1.52E-10 | 1.35E-09 |
| humanized VH4/Vk2 | 1.19E-10 | 1.58E-10 | 1.31E-09 |
| humanized VH4/Vk5 | 2.05E-10 | 1.56E-10 | 1.54E-09 |
| humanized VH5/Vk1 | 1.13E-10 | 4.49E-11 | 1.06E-09 |
| humanized VH5/Vk2 | 1.64E-10 | 1.48E-10 | 1.31E-09 |
| humanized VH5/Vk5 | 1.65E-10 | 1.37E-10 | 1.33E-09 |

Figure 12
Table 5

| Humanized TNT005 Variant | $K_D$ (M) | $K_{on}$ (1/Ms) | $k_{dis}$ (1/s) | $R^2$ |
|---|---|---|---|---|
| VH1/Vk1 | 2.277E-10 | 8.641E+05 | 1.967E-04 | 0.996 |
| VH1/Vk2 | 2.078E-10 | 8.177E+05 | 1.699E-04 | 0.996 |
| VH1/Vk5 | 2.169E-10 | 7.763E+05 | 1.684E-04 | 0.996 |
| VH2/Vk1 | 2.508E-10 | 8.294E+05 | 2.080E-04 | 0.996 |
| VH2/Vk2 | 2.059E-10 | 8.354E+05 | 1.720E-04 | 0.997 |
| VH2/Vk5 | 2.080E-10 | 7.979E+05 | 1.660E-04 | 0.996 |
| VH3/Vk2 | 5.850E-10 | 8.379E+05 | 4.902E-04 | 0.997 |
| VH5/Vk1 | 4.572E-10 | 1.030E+06 | 4.710E-04 | 0.996 |

Figure 13

EPTMYGEILSPNYPQAYPSEVEKSWDIEVPEGYIHLYFTHLDIELSENCAYDSVQIISG
DTEEGRLCGQRSSNNPHSPIVEEFQVPYNKLQVIFKSDFSNEERFTGFAAYVATDINEC
TDFVDVPCSHFCNNFIGGYFCSCPPEYFLHDDMKNCGVNCSGDVFTALIGEIASPNYPKP
YPENSRCEYQIRLEKGFQVVVTLREDFDVEAADSAGNCLDSLVFVAGDRQFGPYCGHGF
PGPLNIETKSNALDIIFQTDLTGQKKGWKLRYHGDPMPCPKEDTPNSVWEPAKAKYVFRD
VVQITCLDGFEVVEGRVGATSFYSTCQSNGKWSNSKLKCQPVDCGIPESIENGKVEDPES
TLFGSVIRYTCEEPYYYMENGGGGEYHCAGNGSWVNEVLGPELPKCVPVCGVPREPFEEK
QRIIGGSDADIKNFPMQVFFDNPWAGGALINEYWLTAAHVVEGNREPTMYVGSTSVQTS
RLAKSKMLTPEHVFIHPGWKLLEVPEGRTNFDNDIALVRLKDPVKMGPTVSPICLPGTSS
DYNLMDGDLGLISGWGRTEKRDRAVRLKAARLPVAPLRKCKEVKVEKPTADAEAYVFTPN
MICAGGEKGMDSCKGDSGGAFAVQDPNDKTKFYAAGLVSWGPQCGTYGLYTRVKNYVDWI
MKTMQENSTPRED (SEQ ID NO: 9)

SEQUENCE LISTING

```
<160> NUMBER OF SEQ ID NOS: 27

<210> SEQ ID NO 1
<211> LENGTH: 15
<212> TYPE: PRT
<213> ORGANISM: Mus musculus

<400> SEQUENCE: 1

Lys Ala Ser Gln Ser Val Asp Tyr Asp Gly Asp Ser Tyr Met Asn
1               5                   10                  15

<210> SEQ ID NO 2
<211> LENGTH: 7
<212> TYPE: PRT
<213> ORGANISM: Mus musculus

<400> SEQUENCE: 2

Asp Ala Ser Asn Leu Glu Ser
1               5

<210> SEQ ID NO 3
<211> LENGTH: 9
<212> TYPE: PRT
<213> ORGANISM: Mus musculus

<400> SEQUENCE: 3

Gln Gln Ser Asn Glu Asp Pro Trp Thr
1               5

<210> SEQ ID NO 4
<211> LENGTH: 5
<212> TYPE: PRT
<213> ORGANISM: Mus musculus

<400> SEQUENCE: 4

Asp Asp Tyr Ile His
1               5

<210> SEQ ID NO 5
<211> LENGTH: 17
<212> TYPE: PRT
<213> ORGANISM: Mus musculus

<400> SEQUENCE: 5

Arg Ile Asp Pro Ala Asp Gly His Thr Lys Tyr Ala Pro Lys Phe Gln
1               5                   10                  15

Val

<210> SEQ ID NO 6
```

```
<211> LENGTH: 10
<212> TYPE: PRT
<213> ORGANISM: Mus musculus

<400> SEQUENCE: 6

Tyr Gly Tyr Gly Arg Glu Val Phe Asp Tyr
1               5                   10

<210> SEQ ID NO 7
<211> LENGTH: 111
<212> TYPE: PRT
<213> ORGANISM: Mus musculus

<400> SEQUENCE: 7

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Thr Gly Gln Pro Pro
        35                  40                  45

Lys Ile Leu Ile Tyr Asp Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Ile Tyr Tyr Cys Gln Gln Ser Asn
                85                  90                  95

Glu Asp Pro Trp Thr Phe Gly Gly Gly Thr Lys Leu Glu Ile Lys
            100                 105                 110

<210> SEQ ID NO 8
<211> LENGTH: 119
<212> TYPE: PRT
<213> ORGANISM: Mus musculus

<400> SEQUENCE: 8

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Asp
            20                  25                  30

Tyr Ile His Trp Val Lys Gln Arg Pro Glu Gln Gly Leu Glu Trp Ile
        35                  40                  45

Gly Arg Ile Asp Pro Ala Asp Gly His Thr Lys Tyr Ala Pro Lys Phe
    50                  55                  60

Gln Val Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Tyr Gly Tyr Gly Arg Glu Val Phe Asp Tyr Trp Gly Gln Gly
            100                 105                 110

Thr Thr Leu Thr Val Ser Ser
        115

<210> SEQ ID NO 9
<211> LENGTH: 673
<212> TYPE: PRT
<213> ORGANISM: Homo sapiens

<400> SEQUENCE: 9

Glu Pro Thr Met Tyr Gly Glu Ile Leu Ser Pro Asn Tyr Pro Gln Ala
```

```
1               5                   10                  15
Tyr Pro Ser Glu Val Glu Lys Ser Trp Asp Ile Glu Val Pro Glu Gly
            20                  25                  30

Tyr Gly Ile His Leu Tyr Phe Thr His Leu Asp Ile Glu Leu Ser Glu
            35                  40                  45

Asn Cys Ala Tyr Asp Ser Val Gln Ile Ile Ser Gly Asp Thr Glu Glu
            50                  55                  60

Gly Arg Leu Cys Gly Gln Arg Ser Ser Asn Pro His Ser Pro Ile
65                      70                  75                  80

Val Glu Glu Phe Gln Val Pro Tyr Asn Lys Leu Gln Val Ile Phe Lys
                    85                  90                  95

Ser Asp Phe Ser Asn Glu Glu Arg Phe Thr Gly Phe Ala Ala Tyr Tyr
                    100                 105                 110

Val Ala Thr Asp Ile Asn Glu Cys Thr Asp Phe Val Asp Val Pro Cys
                    115                 120                 125

Ser His Phe Cys Asn Asn Phe Ile Gly Gly Tyr Phe Cys Ser Cys Pro
                    130                 135                 140

Pro Glu Tyr Phe Leu His Asp Asp Met Lys Asn Cys Gly Val Asn Cys
145                     150                 155                 160

Ser Gly Asp Val Phe Thr Ala Leu Ile Gly Glu Ile Ala Ser Pro Asn
                    165                 170                 175

Tyr Pro Lys Pro Tyr Pro Glu Asn Ser Arg Cys Glu Tyr Gln Ile Arg
                    180                 185                 190

Leu Glu Lys Gly Phe Gln Val Val Thr Leu Arg Arg Glu Asp Phe
                    195                 200                 205

Asp Val Glu Ala Ala Asp Ser Ala Gly Asn Cys Leu Asp Ser Leu Val
        210                     215                 220

Phe Val Ala Gly Asp Arg Gln Phe Gly Pro Tyr Cys Gly His Gly Phe
225                     230                 235                 240

Pro Gly Pro Leu Asn Ile Glu Thr Lys Ser Asn Ala Leu Asp Ile Ile
                    245                 250                 255

Phe Gln Thr Asp Leu Thr Gly Gln Lys Lys Gly Trp Lys Leu Arg Tyr
                    260                 265                 270

His Gly Asp Pro Met Pro Cys Pro Lys Glu Asp Thr Pro Asn Ser Val
            275                 280                 285

Trp Glu Pro Ala Lys Ala Lys Tyr Val Phe Arg Asp Val Val Gln Ile
            290                 295                 300

Thr Cys Leu Asp Gly Phe Glu Val Val Glu Gly Arg Val Gly Ala Thr
305                     310                 315                 320

Ser Phe Tyr Ser Thr Cys Gln Ser Asn Gly Lys Trp Ser Asn Ser Lys
                    325                 330                 335

Leu Lys Cys Gln Pro Val Asp Cys Gly Ile Pro Glu Ser Ile Glu Asn
            340                 345                 350

Gly Lys Val Glu Asp Pro Glu Ser Thr Leu Phe Gly Ser Val Ile Arg
            355                 360                 365

Tyr Thr Cys Glu Glu Pro Tyr Tyr Met Glu Asn Gly Gly Gly
            370                 375                 380

Glu Tyr His Cys Ala Gly Asn Gly Ser Trp Val Asn Glu Val Leu Gly
385                     390                 395                 400

Pro Glu Leu Pro Lys Cys Val Pro Val Cys Gly Val Pro Arg Glu Pro
                    405                 410                 415

Phe Glu Glu Lys Gln Arg Ile Ile Gly Gly Ser Asp Ala Asp Ile Lys
            420                 425                 430
```

```
Asn Phe Pro Trp Gln Val Phe Asp Asn Pro Trp Ala Gly Gly Ala
        435                 440                 445

Leu Ile Asn Glu Tyr Trp Val Leu Thr Ala Ala His Val Val Glu Gly
450                 455                 460

Asn Arg Glu Pro Thr Met Tyr Val Gly Ser Thr Ser Val Gln Thr Ser
465                 470                 475                 480

Arg Leu Ala Lys Ser Lys Met Leu Thr Pro Glu His Val Phe Ile His
                485                 490                 495

Pro Gly Trp Lys Leu Leu Glu Val Pro Glu Gly Arg Thr Asn Phe Asp
            500                 505                 510

Asn Asp Ile Ala Leu Val Arg Leu Lys Asp Pro Val Lys Met Gly Pro
        515                 520                 525

Thr Val Ser Pro Ile Cys Leu Pro Gly Thr Ser Ser Asp Tyr Asn Leu
    530                 535                 540

Met Asp Gly Asp Leu Gly Leu Ile Ser Gly Trp Gly Arg Thr Glu Lys
545                 550                 555                 560

Arg Asp Arg Ala Val Arg Leu Lys Ala Ala Arg Leu Pro Val Ala Pro
                565                 570                 575

Leu Arg Lys Cys Lys Glu Val Lys Val Glu Lys Pro Thr Ala Asp Ala
            580                 585                 590

Glu Ala Tyr Val Phe Thr Pro Asn Met Ile Cys Ala Gly Gly Glu Lys
        595                 600                 605

Gly Met Asp Ser Cys Lys Gly Asp Ser Gly Gly Ala Phe Ala Val Gln
    610                 615                 620

Asp Pro Asn Asp Lys Thr Lys Phe Tyr Ala Ala Gly Leu Val Ser Trp
625                 630                 635                 640

Gly Pro Gln Cys Gly Thr Tyr Gly Leu Tyr Thr Arg Val Lys Asn Tyr
                645                 650                 655

Val Asp Trp Ile Met Lys Thr Met Gln Glu Asn Ser Thr Pro Arg Glu
            660                 665                 670

Asp

<210> SEQ ID NO 10
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 10

Glu Val Gln Leu Val Gln Ser Gly Ala Glu Leu Lys Lys Pro Gly Ala
1               5                   10                  15

Ser Val Lys Leu Ser Cys Thr Ala Ser Gly Phe Asn Ile Lys Asp Asp
            20                  25                  30

Tyr Ile His Trp Val Lys Gln Ala Pro Gly Gln Gly Leu Glu Trp Ile
        35                  40                  45

Gly Arg Ile Asp Pro Ala Asp Gly His Thr Lys Tyr Ala Pro Lys Phe
    50                  55                  60

Gln Val Lys Ala Thr Ile Thr Ala Asp Thr Ser Thr Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Tyr Gly Tyr Gly Arg Glu Val Phe Asp Tyr Trp Gly Gln Gly
            100                 105                 110
```

Thr Thr Val Thr Val Ser Ser
        115

<210> SEQ ID NO 11
<211> LENGTH: 357
<212> TYPE: DNA
<213> ORGANISM: Artificial Sequence
<220> FEATURE:
<223> OTHER INFORMATION: Synthetic nucleotide

<400> SEQUENCE: 11

```
gaggttcagc tggtgcagtc tggggctgag cttaagaagc caggggcctc agtcaagttg      60
tcctgcacag cttctggctt taacattaaa gacgactata cactgggt gaagcaggcc       120 cctggacagg gcctggagtg gattggaagg attgatcctg cggatggtca tactaaatat    180
gccccgaagt tccaagtcaa ggccactata actgcagaca catccaccaa cacagcctac    240
ctgcagctca gcagcctgac atctgaggac actgccgtct attactgtgc tagatatggt    300
tacgggaggg aggtctttga ctactggggc caaggcacca ctgtcacagt ctcctca       357
```

<210> SEQ ID NO 12
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 12

Glu Val Gln Leu Val Gln Ser Gly Ala Glu Val Lys Lys Pro Gly Ala
1               5                   10                  15

Ser Val Lys Leu Ser Cys Thr Ala Ser Gly Phe Asn Ile Lys Asp Asp
            20                  25                  30

Tyr Ile His Trp Val Lys Gln Ala Pro Gly Gln Gly Leu Glu Trp Ile
        35                  40                  45

Gly Arg Ile Asp Pro Ala Asp Gly His Thr Lys Tyr Ala Pro Lys Phe
    50                  55                  60

Gln Val Lys Ala Thr Ile Thr Ala Asp Thr Ser Thr Asn Thr Ala Tyr
65                  70                  75                  80

Leu Glu Leu Ser Ser Leu Arg Ser Glu Asp Thr Ala Val Tyr Tyr Cys
                85                  90                  95

Ala Arg Tyr Gly Tyr Gly Arg Glu Val Phe Asp Tyr Trp Gly Gln Gly
            100                 105                 110

Thr Thr Val Thr Val Ser Ser
        115

<210> SEQ ID NO 13
<211> LENGTH: 357
<212> TYPE: DNA
<213> ORGANISM: Artificial Sequence
<220> FEATURE:
<223> OTHER INFORMATION: Synthetic nucleotide

<400> SEQUENCE: 13

```
gaggttcagc tggtgcagtc tggggctgag gtgaagaagc caggggcctc agtcaagttg      60
tcctgcacag cttctggctt taacattaaa gacgactata cactgggt gaagcaggcc       120 cctggacagg gcctggagtg gattggaagg attgatcctg cggatggtca tactaaatat    180
gccccgaagt tccaagtcaa ggccactata actgcagaca catccaccaa cacagcctac    240
ctggagctca gcagcctgag atctgaggac actgccgtct attactgtgc tagatatggt    300
```
tacgggaggg aggtctttga ctactggggc caaggcacca ctgtcacagt ctccctca    357

<210> SEQ ID NO 14
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 14

Gln Val Gln Leu Val Gln Ser Gly Ala Glu Val Lys Lys Pro Gly Ala
1               5                   10                  15

Ser Val Lys Leu Ser Cys Thr Ala Ser Gly Phe Asn Ile Lys Asp Asp
            20                  25                  30

Tyr Ile His Trp Val Lys Gln Ala Pro Gly Gln Gly Leu Glu Trp Ile
        35                  40                  45

Gly Arg Ile Asp Pro Ala Asp Gly His Thr Lys Tyr Ala Pro Lys Phe
    50                  55                  60

Gln Val Lys Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Tyr Gly Tyr Gly Arg Glu Val Phe Asp Tyr Trp Gly Gln Gly
            100                 105                 110

Thr Thr Val Thr Val Ser Ser
        115

<210> SEQ ID NO 15
<211> LENGTH: 357
<212> TYPE: DNA
<213> ORGANISM: Artificial Sequence
<220> FEATURE:
<223> OTHER INFORMATION: Synthetic nucleotide

<400> SEQUENCE: 15
caggttcagc tggtgcagtc tggggctgag gtgaagaagc caggggcctc agtcaaggtg    60
tcctgcacag cttctggctt aacattaaa gacgactata tacactgggt gcgccaggcc    120
cctggacagg gcctggagtg gattggaagg attgatcctg cggatggtca tactaaatat    180
gccccgaagt tccaagtcaa agtcactata actgcagaca catccaccag cacagcctac    240
atggagctca gcagcctgag atctgaggac actgccgtct attactgtgc tagatatggt    300
tacgggaggg aggtctttga ctactggggc caaggcacca ctgtcacagt ctccctca     357

<210> SEQ ID NO 16
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 16

Gln Val Gln Leu Val Gln Ser Gly Ala Glu Val Lys Lys Pro Gly Ala
1               5                   10                  15

Ser Val Lys Val Ser Cys Thr Ala Ser Gly Phe Asn Ile Lys Asp Asp
            20                  25                  30

Tyr Ile His Trp Val Arg Gln Ala Pro Gly Gln Gly Leu Glu Trp Ile
        35                  40                  45

Gly Arg Ile Asp Pro Ala Asp Gly His Thr Lys Tyr Ala Pro Lys Phe
    50                  55                  60

Gln Val Lys Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Gly Tyr Gly Arg Glu Val Phe Asp Tyr Trp Gly Gln Gly
            100                 105                 110

Thr Thr Val Thr Val Ser Ser
        115

<210> SEQ ID NO 17
<211> LENGTH: 357
<212> TYPE: DNA
<213> ORGANISM: Artificial Sequence
<220> FEATURE:
<223> OTHER INFORMATION: Synthetic nucleotide

<400> SEQUENCE: 17
caggttcagc tggtgcagtc tggggctgag gtgaagaagc caggggcctc agtcaaggtc      60
tcctgcacag cttctggctt taacattaaa gacgactata cactgggt gcgccaggcc     120 cctggacagg gcctggagtg gattggaagg attgatcctg cggatggtca tactaaatat    180
gccccgaagt tccaagtcaa agtcactata actgcagaca catccaccag cacagcctac    240
atggagctca gcagcctgag atctgaggac actgccgtct attactgtgc tagatatggt    300
tacgggaggg aggtctttga ctactggggc caaggcacca ctgtcacagt ctcctca       357

<210> SEQ ID NO 18
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 18

Gln Val Gln Leu Val Gln Ser Gly Ala Glu Val Lys Lys Pro Gly Ala
1               5                   10                  15

Ser Val Lys Val Ser Cys Ala Ala Ser Gly Phe Asn Ile Lys Asp Asp
            20                  25                  30

Tyr Ile His Trp Val Arg Gln Ala Pro Gly Gln Gly Leu Glu Trp Ile
        35                  40                  45

Gly Arg Ile Asp Pro Ala Asp Gly His Thr Lys Tyr Ala Pro Lys Phe
    50                  55                  60

Gln Val Lys Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Gly Tyr Gly Arg Glu Val Phe Asp Tyr Trp Gly Gln Gly
            100                 105                 110

Thr Thr Val Thr Val Ser Ser
        115

<210> SEQ ID NO 19
<211> LENGTH: 357
<212> TYPE: DNA
<213> ORGANISM: Artificial Sequence
<220> FEATURE:
<223> OTHER INFORMATION: Synthetic nucleotide

<400> SEQUENCE: 19

```
caggttcagc tggtgcagtc tggggctgag gtgaagaagc caggggcctc agtcaaggtc      60
tcctgcgcag cttctggctt taacattaaa gacgactata tacactgggt gcgccaggcc     120
cctggacagg gcctggagtg gattggaagg attgatcctg cggatggtca tactaaatat     180
gccccgaagt tccaagtcaa agtcactata actgcagaca catccaccag cacagcctac     240
atggagctca gcagcctgag atctgaggac actgccgtct attactgtgc tagatatggt     300
tacgggaggg aggtctttga ctactggggc caaggcacca ctgtcacagt ctcctca        357
```

<210> SEQ ID NO 20
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 20

```
Asp Ile Val Leu Thr Gln Ser Pro Asp Ser Leu Ala Val Ser Leu Gly
1               5                   10                  15

Glu Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Thr Gly Gln Pro Pro
        35                  40                  45

Lys Ile Leu Ile Tyr Asp Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Glu Glu Asp Phe Ala Ile Tyr Tyr Cys Gln Gln Ser Asn
                85                  90                  95

Glu Asp Pro Trp Thr Phe Gly Gly Gly Thr Lys Val Glu Ile Lys
            100                 105                 110
```

<210> SEQ ID NO 21
<211> LENGTH: 333
<212> TYPE: DNA
<213> ORGANISM: Artificial Sequence
<220> FEATURE:
<223> OTHER INFORMATION: Synthetic nucleotide

<400> SEQUENCE: 21

```
gacattgtgc tgacccaatc tccagactct ttggctgtgt ctctcgggga gagggccacc      60
atctcctgca aggccagcca aagtgttgat tatgatggtg atagttatat gaactggtac     120
caacaaaaaa caggacagcc acccaaaatc ctcatttatg atgcatccaa tttggaatct     180
ggcatcccag ccaggtttag tggcagtggg tctgggacag acttcaccct caccatcagc     240
agcctggagg aggaggattt tgcaatctat tactgtcagc aaagtaatga agacccgtgg     300
acgttcggtg aggcaccaa ggtggaaatc aaa                                   333
```

<210> SEQ ID NO 22
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 22

```
Asp Ile Val Leu Thr Gln Ser Pro Asp Ser Leu Ala Val Ser Leu Gly
1               5                   10                  15

Glu Arg Ala Thr Ile Ser Cys Lys Ala Ser Gln Ser Val Asp Tyr Asp
            20                  25                  30
```

```
                    20                  25                  30

Gly Asp Ser Tyr Met Asn Trp Tyr Gln Gln Lys Pro Gly Gln Pro Pro
                35                  40                  45

Lys Ile Leu Ile Tyr Asp Ala Ser Asn Leu Glu Ser Gly Ile Pro Ala
 50                 55                  60

Arg Phe Ser Gly Ser Gly Ser Gly Thr Asp Phe Thr Leu Thr Ile Ser
 65                 70                  75                  80

Ser Leu Glu Pro Glu Asp Phe Ala Ile Tyr Tyr Cys Gln Gln Ser Asn
                85                  90                  95

Glu Asp Pro Trp Thr Phe Gly Gly Gly Thr Lys Val Glu Ile Lys
                100                 105                 110

<210> SEQ ID NO 23
<211> LENGTH: 333
<212> TYPE: DNA
<213> ORGANISM: Artificial Sequence
<220> FEATURE:
<223> OTHER INFORMATION: Synthetic nucleotide

<400> SEQUENCE: 23
gacattgtgc tgacccaatc tccagactct ttggctgtgt ctctcgggga gagggccacc    60
atctcctgca aggccagcca aagtgttgat tatgatggtg atagttatat gaactggtac   120
caacaaaaac caggacagcc acccaaaatc ctcatttatg atgcatccaa tttggaatct   180
ggcatcccag ccaggtttag tggcagtggg tctgggacag acttcaccct caccatcagc   240
agcctggagc ctgaggattt tgcaatctat tactgtcagc aaagtaatga agacccgtgg   300
acgttcggtg gaggcaccaa ggtggaaatc aaa                                333

<210> SEQ ID NO 24
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 24

Asp Ile Val Leu Thr Gln Ser Pro Asp Ser Leu Ala Val Ser Leu Gly
  1               5                  10                  15

Glu Arg Ala Thr Ile Ser Cys Lys Ala Ser Gln Ser Val Asp Tyr Asp
                20                  25                  30

Gly Asp Ser Tyr Met Asn Trp Tyr Gln Gln Lys Pro Gly Gln Pro Pro
                35                  40                  45

Lys Leu Leu Ile Tyr Asp Ala Ser Asn Leu Glu Ser Gly Ile Pro Ala
 50                 55                  60

Arg Phe Ser Gly Ser Gly Ser Gly Thr Asp Phe Thr Leu Thr Ile Ser
 65                 70                  75                  80

Ser Leu Glu Pro Glu Asp Phe Ala Val Tyr Tyr Cys Gln Gln Ser Asn
                85                  90                  95

Glu Asp Pro Trp Thr Phe Gly Gly Gly Thr Lys Val Glu Ile Lys
                100                 105                 110

<210> SEQ ID NO 25
<211> LENGTH: 333
<212> TYPE: DNA
<213> ORGANISM: Artificial Sequence
<220> FEATURE:
<223> OTHER INFORMATION: Synthetic nucleotide

<400> SEQUENCE: 25
```
gacattgtgc tgacccaatc tccagactct ttggctgtgt ctctcgggga gagggccacc    60
atctcctgca aggccagcca aagtgttgat tatgatggtg atagttatat gaactggtac   120
caacaaaaac caggacagcc acccaaactc ctcatttatg atgcatccaa tttggaatct   180
ggcatcccag ccaggtttag tggcagtggg tctgggacag acttcaccct caccatcagc   240
agcctggagc ctgaggattt tgcagtctat tactgtcagc aaagtaatga agacccgtgg   300
acgttcggtg gaggcaccaa ggtggaaatc aaa                                333

<210> SEQ ID NO 26
<211> LENGTH: 119
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be glutamine (Q) or glutamic acid (E)
<220> FEATURE:
<221> NAME/KEY: MISC_FEATURE
<222> LOCATION: (5)..(5)
<223> OTHER INFORMATION: Xaa can be glutamine (Q) or valine (V)
<220> FEATURE:
<221> NAME/KEY: MISC_FEATURE
<222> LOCATION: (11)..(11)
<223> OTHER INFORMATION: Xaa can be valine (V) or leucine (L)
<220> FEATURE:
<221> NAME/KEY: MISC_FEATURE
<222> LOCATION: (20)..(20)
<223> OTHER INFORMATION: Xaa can be leucine (L) or valine (V)
<220> FEATURE:
<221> NAME/KEY: MISC_FEATURE
<222> LOCATION: (23)..(23)
<223> OTHER INFORMATION: Xaa can be threonine (T) or alanine (A)
<220> FEATURE:
<221> NAME/KEY: MISC_FEATURE
<222> LOCATION: (38)..(38)
<223> OTHER INFORMATION: Xaa can be lysine (K) or arginine (R)
<220> FEATURE:
<221> NAME/KEY: MISC_FEATURE
<222> LOCATION: (68)..(68)
<223> OTHER INFORMATION: Xaa can be valine (V) or alanine (A)
<220> FEATURE:
<221> NAME/KEY: MISC_FEATURE
<222> LOCATION: (77)..(77)
<223> OTHER INFORMATION: Xaa can be serine (S) or asparagine (N)
<220> FEATURE:
<221> NAME/KEY: MISC_FEATURE
<222> LOCATION: (81)..(81)
<223> OTHER INFORMATION: Xaa can be leucine (L) or methionine (M)
<220> FEATURE:
<221> NAME/KEY: MISC_FEATURE
<222> LOCATION: (82)..(82)
<223> OTHER INFORMATION: Xaa can be glutamic acid (E) or glutamine (Q)
<220> FEATURE:
<221> NAME/KEY: MISC_FEATURE
<222> LOCATION: (87)..(87)
<223> OTHER INFORMATION: Xaa can be arginine (R) or threonine (T)

<400> SEQUENCE: 26

Xaa Val Gln Leu Xaa Gln Ser Gly Ala Glu Xaa Lys Lys Pro Gly Ala
1               5                   10                  15

Ser Val Lys Xaa Ser Cys Xaa Ala Ser Gly Phe Asn Ile Lys Asp Asp
            20                  25                  30

Tyr Ile His Trp Val Xaa Gln Ala Pro Gly Gln Gly Leu Glu Trp Ile
        35                  40                  45

Gly Arg Ile Asp Pro Ala Asp Gly His Thr Lys Tyr Ala Pro Lys Phe
    50                  55                  60

```
Gln Val Lys Xaa Thr Ile Thr Ala Asp Thr Ser Thr Xaa Thr Ala Tyr
 65                  70                  75                  80

Xaa Xaa Leu Ser Ser Leu Xaa Ser Glu Asp Thr Ala Val Tyr Tyr Cys
                 85                  90                  95

Ala Arg Tyr Gly Tyr Gly Arg Glu Val Phe Asp Tyr Trp Gly Gln Gly
            100                 105                 110

Thr Thr Val Thr Val Ser Ser
        115

<210> SEQ ID NO 27
<211> LENGTH: 111
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (44)..(44)
<223> OTHER INFORMATION: Xaa can be threonine (T) or proline (P)
<220> FEATURE:
<221> NAME/KEY: MISC_FEATURE
<222> LOCATION: (50)..(50)
<223> OTHER INFORMATION: Xaa can be isoleucine (I) or leucine (L)
<220> FEATURE:
<221> NAME/KEY: MISC_FEATURE
<222> LOCATION: (84)..(84)
<223> OTHER INFORMATION: Xaa can be glutamic acid (E) or proline (P)
<220> FEATURE:
<221> NAME/KEY: MISC_FEATURE
<222> LOCATION: (89)..(89)
<223> OTHER INFORMATION: Xaa can be isoleucine (I) or valine (V)

<400> SEQUENCE: 27

Asp Ile Val Leu Thr Gln Ser Pro Asp Ser Leu Ala Val Ser Leu Gly
  1               5                  10                  15

Glu Arg Ala Thr Ile Ser Cys Lys Ala Ser Gln Ser Val Asp Tyr Asp
                 20                  25                  30

Gly Asp Ser Tyr Met Asn Trp Tyr Gln Gln Lys Xaa Gly Gln Pro Pro
             35                  40                  45

Lys Xaa Leu Ile Tyr Asp Ala Ser Asn Leu Glu Ser Gly Ile Pro Ala
 50                  55                  60

Arg Phe Ser Gly Ser Gly Ser Gly Thr Asp Phe Thr Leu Thr Ile Ser
 65                  70                  75                  80

Ser Leu Glu Xaa Glu Asp Phe Ala Xaa Tyr Tyr Cys Gln Gln Ser Asn
                 85                  90                  95

Glu Asp Pro Trp Thr Phe Gly Gly Gly Thr Lys Val Glu Ile Lys
            100                 105                 110
```

HUMANIZED ANTI-C1S ANTIBODIES AND METHODS OF INHIBITING C1S CLEAVAGE

CROSS-REFERENCE

This application claims the benefit of U.S. Provisional Patent Application Nos. 62/143,636, filed Apr. 6, 2015, and 62/200,997, filed Aug. 4, 2015, which applications are incorporated herein by reference in their entirety.

REFERENCE TO SEQUENCE LISTING SUBMITTED ELECTRONICALLY VIA EFS-WEB

The content of the electronically submitted sequence listing (Name: 4159_5020002_SequenceListing.TXT; Size: 26,427 bytes; Date of creation: Oct. 5, 2017) was originally submitted in International Application No. PCT/US2016/02038 and is incorporated herein by reference in its entirety.

INTRODUCTION

The complement system is a well-known effector mechanism of the immune response, providing not only protection against pathogens and other harmful agents but also recovery from injury. The complement pathway comprises a number of proteins that typically exist in the body in inactive form. The classical complement pathway is triggered by activation of the first component of complement, referred to as the C1 complex, which consists of C1q, C1r, and C1s proteins. Upon binding of C1 to an immune complex or other activator, the C1s component, a diisopropyl fluorophosphate (DFP)-sensitive serine protease, cleaves complement components C4 and C2 to initiate activation of the classical complement pathway. The classical complement pathway appears to play a role in many diseases and disorders.

SUMMARY

The present disclosure provides humanized anti-C1s antibodies. The present disclosure provides nucleic acids comprising nucleotide sequences encoding the humanized anti-C1s antibodies; and host cells comprising the nucleic acids. The present disclosure provides compositions comprising the humanized anti-C1s antibodies. The present disclosure provides methods of use of the humanized anti-C1s antibodies.

The present disclosure provides a humanized antibody that specifically binds complement component C1s, wherein the antibody comprises: a) a VH region comprising the amino acid sequence:
(Q/E)VQL(V/Q)QSGAE(V/L)KKPGASVK(L/V)SC(T/A)ASGFNIKDDYIHWV(K/R)QAPGQ GLEWIGRID-PADGHTKYAPKFQVK(V/A)TITADTST(S/N)TAY(L/M)(E/Q)LSSL(R/T)SED TAVYYCARYGYGREVFDYWGQGTTVTVSS (SEQ ID NO:26); and b) a VL region comprising the amino acid sequence:

```
                                          (SEQ ID NO: 27)
DIVLTQSPDSLAVSLGERATISCKASQSVDYDGDSYMNWYQQK(T/P)GQ

PPK(I/L)LIYDASNLESGIPARFSGSGSGTDFTLTISSLE(E/P)EDFA (I/V)YYCQQSNEDPWTFGGGTKVEIK.
```

In some cases, the antibody comprises: a) a VH region comprising SEQ ID NO:10; and b) a VL region comprising SEQ ID NO:20. In some cases, the antibody comprises: a) a VH region comprising SEQ ID NO:10; and b) a VL region comprising SEQ ID NO:22. In some cases, the antibody comprises: a) a VH region comprising SEQ ID NO:10; and b) a VL region comprising SEQ ID NO:24. In some cases, the antibody comprises: a) a VH region comprising SEQ ID NO:12; and b) a VL region comprising SEQ ID NO:20. In some cases, the antibody comprises: a) a VH region comprising SEQ ID NO:12; and b) a VL region comprising SEQ ID NO:22. In some cases, the antibody comprises: a) a VH region comprising SEQ ID NO:12; and b) a VL region comprising SEQ ID NO:24. In some cases, the antibody comprises: a) a VH region comprising SEQ ID NO:14; and b) a VL region comprising SEQ ID NO:20. In some cases, the antibody comprises: a) a VH region comprising SEQ ID NO:14; and b) a VL region comprising SEQ ID NO:22. In some cases, the antibody comprises: a) a VH region comprising SEQ ID NO:14; and b) a VL region comprising SEQ ID NO:24. In some cases, the antibody comprises: a) a VH region comprising SEQ ID NO:16; and b) a VL region comprising SEQ ID NO:20. In some cases, the antibody comprises: a) a VH region comprising SEQ ID NO:16; and b) a VL region comprising SEQ ID NO:22. In some cases, the antibody comprises: a) a VH region comprising SEQ ID NO:16; and b) a VL region comprising SEQ ID NO:24. In some cases, the antibody comprises: a) a VH region comprising SEQ ID NO:18; and b) a VL region comprising SEQ ID NO:20. In some cases, the antibody comprises: a) a VH region comprising SEQ ID NO:18; and b) a VL region comprising SEQ ID NO:22. In some cases, the antibody comprises: a) a VH region comprising SEQ ID NO:18; and b) a VL region comprising SEQ ID NO:24. In some cases, the humanized antibody is selected from the group consisting of a Fab fragment, a F(ab')₂ fragment, a scFv, and a Fv. In some cases, the humanized antibody comprises a heavy chain constant region of the isotype IgG1, IgG2, IgG3, or IgG4.

The present disclosure provides a composition comprising: a) a humanized antibody as described above and infra; and b) a pharmaceutically acceptable excipient. In some cases, the composition comprises one or more of a tonicity agent, a suspending agent, an emulsifying agent, a stabilizer, a preservative, a lyoprotectant, a surfactant, and a sugar. The present disclosure provides a container comprising a composition of the present disclosure. In some cases, the container is sterile. In some cases, the container is a vial, a bottle, or a syringe.

The present disclosure provides a method of reducing the level of a complement component cleavage product in an individual (e.g., in a fluid, tissue, or organ of the individual), the method comprising administering to the individual a humanized antibody of the present disclosure as described above or infra, or a composition of the present disclosure as described above or infra, in an amount effective to inhibit C1s and to reduce the level of the cleavage product. In some cases, the complement component cleavage product is a C4 cleavage product (e.g., C4b). In some cases, the complement component cleavage product is a C2 cleavage product (e.g., C2a). In some cases, the complement component cleavage product is a C3 cleavage product. In some cases, the individual is a human. In some cases, the administering is intravenous. In some cases, the administering is intramuscular. In some cases, the administering is intrathecal. In some cases, the administering is subcutaneous. In some cases, reduction of the level of a complement component cleavage product is effective to treat a complement-mediated disorder. In some cases, the complement-mediated disorder is an alloimmune disorder. In some cases, the complement-mediated disorder is an autoimmune disorder.

The present disclosure provides a method of inhibiting C1s-mediated cleavage of a complement component in an individual, the method comprising administering to the individual a humanized antibody of the present disclosure as described above or infra, or a composition of the present disclosure as described above or infra, in an amount effective to inhibit C1s-mediated cleavage of a complement component. In some cases, the individual is a human. In some cases, the administering is intravenous. In some cases, the administering is intramuscular. In some cases, the administering is intrathecal. In some cases, the administering is subcutaneous. In some cases, inhibition of C1s-mediated cleavage of a complement component is effective to treat a complement-mediated disorder. In some cases, the complement-mediated disorder is an alloimmune disorder. In some cases, the complement-mediated disorder is an autoimmune disorder.

The present disclosure provides a method of treating a complement-mediated disease or disorder in an individual, the method comprising administering to the individual a humanized antibody of the present disclosure as described above or infra, or a composition of the present disclosure as described above or infra, in an amount effective to treat the complement-mediated disease or disorder. In some cases, the complement component cleavage product is a C3 cleavage product. In some cases, the individual is a human. In some cases, the administering is intravenous. In some cases, the administering is intramuscular. In some cases, the administering is intrathecal. In some cases, the administering is subcutaneous. In some cases, reduction of the level of a complement component cleavage product is effective to treat a complement-mediated disorder. In some cases, the complement-mediated disorder is an alloimmune disorder. In some cases, the complement-mediated disorder is an autoimmune disorder.

BRIEF DESCRIPTION OF THE DRAWINGS

FIG. 1 depicts an amino acid sequence of humanized VH variant 1 (SEQ ID NO:10) and a nucleotide sequence (SEQ ID NO:11) encoding same.

FIG. 2 depicts an amino acid sequence of humanized VH variant 2 (SEQ ID NO:12) and a nucleotide sequence (SEQ ID NO:13) encoding same.

FIG. 3 depicts an amino acid sequence of humanized VH variant 3 (SEQ ID NO:14) and a nucleotide sequence (SEQ ID NO:15) encoding same.

FIG. 4 depicts an amino acid sequence of humanized VH variant 4 (SEQ ID NO:16) and a nucleotide sequence (SEQ ID NO:17) encoding same.

FIG. 5 depicts an amino acid sequence of humanized VH variant 5 (SEQ ID NO:18) and a nucleotide sequence (SEQ ID NO:19) encoding same.

FIG. 6 depicts an amino acid sequence of humanized Vκ variant 1 (SEQ ID NO:20) and a nucleotide sequence (SEQ ID NO:21) encoding same.

FIG. 7 depicts an amino acid sequence of humanized Vκ variant 2 (SEQ ID NO:22) and a nucleotide sequence (SEQ ID NO:23) encoding same.

FIG. 8 depicts an amino acid sequence of humanized Vκ variant 5 (SEQ ID NO:24) and a nucleotide sequence (SEQ ID NO:25) encoding same.

FIG. 9 provides Table 2, which shows amino acid differences between parental TNT005 VH and exemplary humanized VH variants.

FIG. 10 provides Table 3, which shows amino acid differences between parental TNT005 VL and exemplary humanized VL variants.

FIG. 11 provides Table 4, which shows binding properties of humanized variants of TNT005. Data for direct binding to activated C1s ("aC1s"), competition binding with 50 pM biotinylated-TNT005 ("Biot-005"), and inhibition of the classical complement pathway, are shown.

FIG. 12 provides Table 5, which shows binding properties of humanized variants of TNT005. Affinity data for binding of humanized variants of TNT005 to active human C1s are provided.

FIG. 13 provides an amino acid sequence of human C1s.

DEFINITIONS

Figure 14:
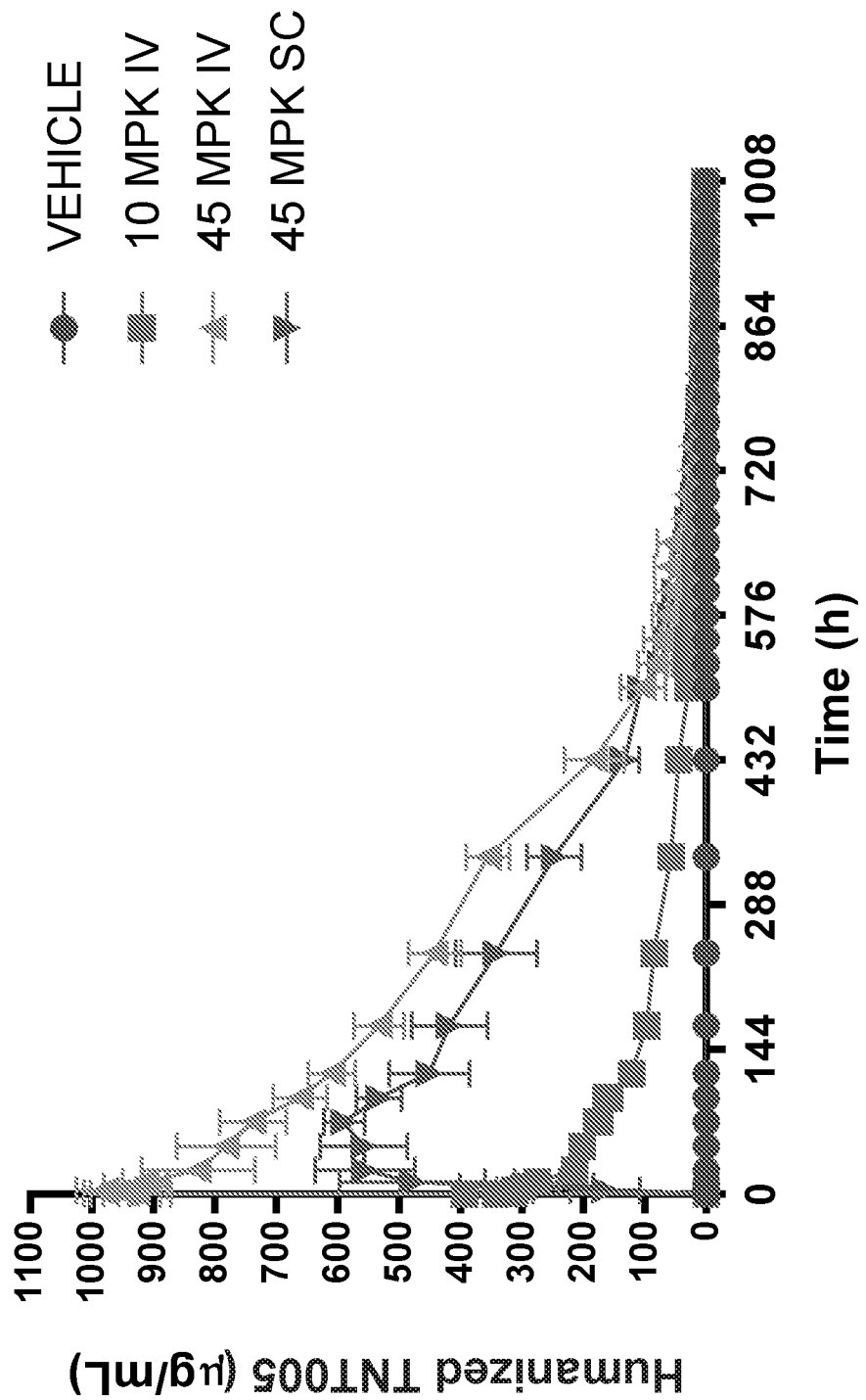
FIG. 14 depicts a pharmacokinetic (PK) profile of a humanized TNT005 variant in cynomolgus monkeys dosed in Phase 1 (Day 1-Day 43).

The terms "antibodies" and "immunoglobulin" include antibodies or immunoglobulins of any isotype, fragments of antibodies that retain specific binding to antigen, including, but not limited to, Fab, Fv, scFv, and Fd fragments, chimeric antibodies, humanized antibodies, single-chain antibodies (scAb), single domain antibodies (dAb), single domain heavy chain antibodies, a single domain light chain antibodies, bi-specific antibodies, multi-specific antibodies, and fusion proteins comprising an antigen-binding (also referred to herein as antigen binding) portion of an antibody and a non-antibody protein. The antibodies can be detectably labeled, e.g., with a radioisotope, an enzyme that generates a detectable product, a fluorescent protein, and the like. The antibodies can be further conjugated to other moieties, such as members of specific binding pairs, e.g., biotin (member of biotin-avidin specific binding pair), and the like. The antibodies can also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies. As used herein, a monoclonal antibody is an antibody produced by a group of identical cells, all of which were produced from a single cell by repetitive cellular replication. That is, the clone of cells only produces a single antibody species. While a monoclonal antibody can be produced using hybridoma production technology, other production methods known to those skilled in the art can also be used (e.g., antibodies derived from antibody phage display libraries). An antibody can be monovalent or bivalent. An antibody can be an Ig monomer, which is a "Y-shaped" molecule that consists of four polypeptide chains: two heavy chains and two light chains connected by disulfide bonds.

The term "humanized immunoglobulin" or "humanized antibody" as used herein refers to an immunoglobulin comprising portions of immunoglobulins of different origin, wherein at least one portion comprises amino acid sequences of human origin. For example, the humanized antibody can comprise portions derived from an immunoglobulin of non-human origin with the requisite specificity, such as a mouse, and from immunoglobulin sequences of human origin (e.g., chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin is an immunoglobulin containing one or more immunoglobulin chains comprising a CDR derived from an antibody of nonhuman origin and a framework region derived from a light and/or heavy chain of human origin (e.g., CDR-grafted antibodies with or without framework changes). Chimeric or CDR-grafted single chain antibodies are also encompassed by the term humanized immunoglobulin. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1. See also, Ladner et al., U.S. Pat. No. 4,946,778; Huston, U.S. Pat. No. 5,476,786; and Bird, R. E. et al., Science, 242: 423-426 (1988)), regarding single chain antibodies.

For example, humanized immunoglobulins can be produced using synthetic and/or recombinant nucleic acids to prepare genes (e.g., cDNA) encoding the desired humanized chain. For example, nucleic acid (e.g., DNA) sequences coding for humanized variable regions can be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. For example, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993)).

"Antibody fragments" comprise a portion of an intact antibody, for example, the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 (1995)); domain antibodies (dAb; Holt et al. (2003) Trends Biotechnol. 21:484); single-chain antibody molecules; and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

"Fv" is the minimum antibody fragment that contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain ($CH_1$) of the heavy chain. Fab fragments differ from Fab' fragments by the addition of a few residues at the carboxyl terminus of the heavy chain $CH_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these classes can be further divided into subclasses (isotypes), e.g., IgG1, IgG2, IgG3, IgG4, IgA, and IgA2. The subclasses can be further divided into types, e.g., IgG2a and IgG2b.

"Single-chain Fv" or "sFv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see *Pluckthun in The Pharmacology of Monoclonal Antibodies, vol.* 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) *Proc. Natl. Acad. Sci. USA* 90:6444-6448.

As used herein, the term "affinity" refers to the equilibrium constant for the reversible binding of two agents (e.g., an antibody and an antigen) and is expressed as a dissociation constant ($K_D$). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1,000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/ or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. A humanized anti-C1s antibody of the present disclosure binds specifically to an epitope within a complement C1s protein. "Specific binding" refers to binding with an affinity of at least about $10^{-7}$ M or greater, e.g., $5 \times 10^{-7}$ M, $10^{-8}$ M, $5 \times 10^{-8}$ M, and greater. "Non-specific binding" refers to binding with an affinity of less than about $10^{-7}$ M, e.g., binding with an affinity of $10^{-6}$ M, $10^{-5}$ M, $10^{-4}$ M, etc.

As used herein, the term "CDR" or "complementarity determining region" is intended to mean the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991) (also referred to herein as Kabat 1991); by Chothia et al., J. Mol. Biol. 196:901-917 (1987) (also referred to herein as Chothia 1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues, which encompass the CDRs, as defined by each of the above cited references are set forth below in Table 1 as a comparison. The CDRs depicted in FIGS. 1-8 were defined in accordance with Kabat 1991.

TABLE 1

CDR Definitions

|  | Kabat[1] | Chothia[2] | MacCallum[3] |
|---|---|---|---|
| $V_H$ CDR-1 | 31-35 | 26-32 | 30-35 |
| $V_H$ CDR-2 | 50-65 | 53-55 | 47-58 |
| $V_H$ CDR-3 | 95-102 | 96-101 | 93-101 |
| $V_L$ CDR-1 | 24-34 | 26-32 | 30-36 |
| $V_L$ CDR-2 | 50-56 | 50-52 | 46-55 |
| $V_L$ CDR-3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the terms "CDR-L1", "CDR-L2", and "CDR-L3" refer, respectively, to the first, second, and third CDRs in a light chain variable region. As used herein, the terms "CDR-H1", "CDR-H2", and "CDR-H3" refer, respectively, to the first, second, and third CDRs in a heavy chain variable region. As used herein, the terms "CDR-1", "CDR-2", and "CDR-3" refer, respectively, to the first, second and third CDRs of either chain's variable region.

As used herein, the term "framework" ("FR") when used in reference to an antibody variable region is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term "framework region" is intended to mean each domain of the framework that is separated by the CDRs. A light chain variable region (VL region) can have four framework regions: FR1, FR2, FR3, and FR4. Similarly, a heavy chain variable region (VH) can have four framework regions: FR1, FR2, FR3, and FR4.

An "isolated" antibody is one that has been identified and separated and/or recovered from a component of its natural environment. Contaminant components of its natural environment are materials that would interfere with diagnostic or therapeutic uses for the antibody, and can include enzymes, hormones, and other proteinaceous or nonproteinaceous solutes. In some embodiments, the antibody will be purified (1) to greater than 90%, greater than 95%, or greater than 98%, by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or nonreducing conditions using Coomassie blue or silver stain. Isolated antibody includes the antibody in situ within recombinant cells since at least one component of the antibody's natural environment will not be present. In some instances, isolated antibody will be prepared by at least one purification step.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

As used herein, the terms "treatment," "treating," "treat" and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which can be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc. Also encompassed by these terms are any animal that has a complement system, such as mammals, fish, and some invertebrates. As such these terms include complement system-containing mammal, fish, and invertebrate companion animals, agricultural animals, work animals, zoo animals, and lab animals.

A "therapeutically effective amount" or "efficacious amount" refers to the amount of an anti-complement C1s antibody that, when administered to a mammal or other subject for treating a disease, is sufficient to effect such treatment for the disease. The "therapeutically effective amount" will vary depending on the anti-complement C1s antibody, the disease and its severity and the age, weight, etc., of the subject to be treated.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, interstitial fluid, ocular fluid, synovial fluid, blood fractions such as plasma and serum, and the like. The term "biological sample" also includes solid tissue samples, tissue culture samples, and cellular samples.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a humanized anti-C1s antibody" includes a plurality of such antibodies and reference to "the framework region" includes reference to one or more framework regions and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a humanized antibody that binds complement C1s protein (i.e., a humanized anti-complement C1s antibody, also referred to herein as a "humanized anti-C1s antibody", a "humanized C1s antibody", and a "subject antibody") and a nucleic acid comprising a nucleotide sequence that encodes such an antibody. The present disclosure also provides a composition comprising a humanized anti-C1s antibody of the present disclosure. The present disclosure provides methods of producing and using antibodies, nucleic acids, and compositions of the present disclosure. The present disclosure provides methods of treating a complement-mediated disease or disorder, involving administering a humanized anti-C1s antibody of the present disclosure.

Anti-Complement C1s Antibodies

The present disclosure provides humanized anti-complement C1s antibodies and pharmaceutical compositions comprising such antibodies. Complement C1s is an attractive target as it is upstream in the complement cascade and has a narrow range of substrate specificity. Of interest in some cases is an antibody that specifically binds the activated form of C1s, e.g., where the antibody does not substantially bind the inactive form of C1s.

An anti-C1s antibody of the present disclosure is humanized, e.g., one or more framework regions of the heavy chain variable region and/or the light chain variable region include sequences derived from a human immunoglobulin framework.

In some cases, an anti-C1s antibody of the present disclosure inhibits C1s-mediated cleavage of complement component C4, e.g., by inhibiting enzymatic activity of the serine-protease domain of C1s. In some cases, an anti-C1s antibody of the present disclosure inhibits C1s-mediated cleavage of complement component C2. In some cases, an anti-C1s antibody of the present disclosure inhibits C1s-mediated cleavage of C4 and C2.

Humanization of a framework region(s) reduces the risk of the antibody eliciting a human-anti-mouse-antibody (HAMA) response in humans. Art-recognized methods of determining immune response can be performed to monitor a HAMA response in a particular patient or during clinical trials. Patients administered humanized antibodies can be given an immunogenicity assessment at the beginning and throughout the administration of the therapy. The HAMA response is measured, for example, by detecting antibodies to the humanized therapeutic reagent, in serum samples from the patient using a method known to one in the art, including surface plasmon resonance technology (BIA-CORE) and/or solid-phase enzyme-linked immunosorbent assay (ELISA) analysis. In many cases, a subject humanized anti-C1s antibody does not substantially elicit a HAMA response in a human subject.

Certain amino acids from the human variable region framework residues are selected for substitution based on their possible influence on CDR conformation and/or binding antigen. The unnatural juxtaposition of murine CDR regions with human variable framework region can result in unnatural conformational restraints, which, unless corrected by substitution of certain amino acid residues, lead to loss of binding affinity.

The selection of amino acid residues for substitution can be determined, in part, by computer modeling. Computer hardware and software for producing three-dimensional images of immunoglobulin molecules are known in the art. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, e.g., those sharing at least 60%, at least 70%, at least 80%, at least 90% sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

CDR and framework regions are as defined by Kabat, Sequences of Proteins of Immunological Interest (National Institutes of Health, Bethesda, Md., 1987 and 1991). An alternative structural definition has been proposed by Chothia et al., J. Mol. Biol. 196:901 (1987); Nature 342:878 (1989); and J. Mol. Biol. 186:651 (1989) (collectively referred to as "Chothia"). When framework residues, as defined by Kabat, supra, constitute structural loop residues as defined by Chothia, supra, the amino acids present in the mouse antibody can be selected for substitution into the humanized antibody. Residues that are "adjacent to a CDR region" include amino acid residues in positions immediately adjacent to one or more of the CDRs in the primary sequence of the humanized immunoglobulin chain, for example, in positions immediately adjacent to a CDR as defined by Kabat, or a CDR as defined by Chothia (See e.g., Chothia and Lesk JMB 196:901 (1987)). These amino acids are particularly likely to interact with the amino acids in the CDRs and, if chosen from the acceptor, to distort the donor CDRs and reduce affinity. Moreover, the adjacent amino acids can interact directly with the antigen (Amit et al., Science, 233:747 (1986)) and selecting these amino acids from the donor can be desirable to keep all the antigen contacts that provide affinity in the original antibody.

In some cases, a humanized anti-C1s antibody of the present disclosure includes at least one humanized $V_H$ framework region. In some cases, an anti-C1s antibody of the present disclosure includes at least one humanized $V_L$ framework region. In some cases, an anti-C1s antibody of the present disclosure includes at least one humanized $V_H$ framework region and at least one humanized $V_L$ framework region.

In some cases, a humanized anti-C1s antibody of the present disclosure includes VL CDRs present in the following amino acid sequence:

```
                                                (SEQ ID NO: 7)
DIVLTQSPASLAVSLGQRATISCKASQSVDYDGDSYMNWYQQKTGQPPKI

LIYDASNLESGIPARFSGSGSGTDFTLNIHPVEEEDAAIYYCQQSNEDPW

TFGGGTKLEIK.
```

In some cases, a humanized anti-C1s antibody of the present disclosure includes VH CDRs present in the following amino acid sequence:

```
                                                (SEQ ID NO: 8)
EVQLQQSGAELVRPGASVKLSCTASGFNIKDDYIHWVKQRPEQGLEWIGR

IDPADGHTKYAPKFQVKATITADTSSNTAYLQLSSLTSEDTAVYYCARYG

YGREVFDYWGQGTTLTVSS.
```

In some cases, a humanized anti-C1s antibody of the present disclosure includes VL CDRs present in SEQ ID NO:7 and VH CDRs present in SEQ ID NO:8.

```
VL CDR1 (CDR-L1): SEQ ID NO: 1: KASQSVDYDGDSYMN

VL CDR2 (CDR-L2): SEQ ID NO: 2: DASNLES

VL CDR3 (CDR-L3): SEQ ID NO: 3: QQSNEDPWT

VH CDR1 (CDR-H1): SEQ ID NO: 4: DDYIH

VH CDR2 (CDR-H2): SEQ ID NO: 5: RIDPADGHTKYAPKFQV

VH CDR3 (CDR-H3): SEQ ID NO: 6: YGYGREVFDY
```

In some cases, a humanized anti-C1s antibody of the present disclosure comprises a light chain variable region comprising CDR amino acid sequences SEQ ID NO:1, SEQ ID NO:2, and SEQ ID NO:3 (CDR-L1, CDR-L2, and CDR-L3, respectively).

In some embodiments, an anti-C1s antibody of the present disclosure comprises a heavy chain variable region comprising CDR amino acid sequences SEQ ID NO:4, SEQ ID NO:5, and SEQ ID NO:6 (CDR-H1, CDR-H2, and CDR-H3, respectively).

In some cases, a humanized anti-C1s antibody of the present disclosure comprises a VH region comprising the following sequence:

```
                                                (SEQ ID NO: 26)
(Q/E)VQL(V/Q)QSGAE(V/L)KKPGASVK(L/V)SC(T/A)ASGFNIK

DDYIHWV(K/R)QAPGQGLEWIGRIDPADGHTKYAPKFQVK(V/A)TITA

DTST(S/N)TAY(L/M)(E/Q)LSSL(R/T)SEDTAVYYCARYGYGREVF

DYWGQGTTVTVSS.
```

In some cases, a humanized anti-C1s antibody of the present disclosure comprises a VH region comprising an amino acid sequence having at least 90%, at least 95%, at least 98%, at least 99%, or 100%, amino acid sequence identity to the amino acid sequence depicted in FIG. 1, and set forth in SEQ ID NO:10, where amino acid 1 is Glu, amino acid 5 is Val, amino acid 11 is Leu, amino acid 12 is Lys, amino acid 13 is Lys, amino acid 20 is Leu, amino acid 23 is Thr, amino acid 38 is Lys, amino acid 40 is Ala, amino acid 42 is Gly, amino acid 67 is Ala, amino acid 75 is Thr, amino acid 76 is Asn, amino acid 80 is Leu, amino acid 81 is Gln, amino acid 83 is Thr, and amino acid 109 is Val, where the numbering of the amino acids is as depicted in FIG. 1.

In some cases, a humanized anti-C1s antibody of the present disclosure comprises a VH region comprising the amino acid sequence depicted in FIG. 1, and set forth in SEQ ID NO:10.

In some cases, a humanized anti-C1s antibody of the present disclosure comprises a VH region comprising an amino acid sequence having at least 90%, at least 95%, at least 98%, at least 99%, or 100%, amino acid sequence identity to the amino acid sequence depicted in FIG. 2 and set forth in SEQ ID NO:12, where amino acid 1 is Glu, amino acid 5 is Val, amino acid 11 is Val, amino acid 12 is Lys, amino acid 13 is Lys, amino acid 20 is Leu, amino acid 23 is Thr, amino acid 38 is Lys, amino acid 40 is Ala, amino acid 42 is Gly, amino acid 67 is Ala, amino acid 75 is Thr, amino acid 76 is Asn, amino acid 80 is Leu, amino acid 81 is Glu, amino acid 83 is Arg, and amino acid 109 is Val, where the numbering of the amino acids is as depicted in FIG. 2.

In some cases, a humanized anti-C1s antibody of the present disclosure comprises a VH region comprising the amino acid sequence depicted in FIG. 2, and set forth in SEQ ID NO:12.

In some cases, a humanized anti-C1s antibody of the present disclosure comprises a VH region comprising an amino acid sequence having at least 90%, at least 95%, at least 98%, at least 99%, or 100%, amino acid sequence identity to the amino acid sequence depicted in FIG. 3 and set forth in SEQ ID NO:14, where amino acid 1 is Gln, amino acid 5 is Val, amino acid 11 is Val, amino acid 12 is Lys, amino acid 13 is Lys, amino acid 20 is Leu, amino acid 23 is Thr, amino acid 38 is Lys, amino acid 40 is Ala, amino acid 42 is Gly, amino acid 67 is Val, amino acid 75 is Thr, amino acid 76 is Ser, amino acid 80 is Leu, amino acid 81 is Glu, amino acid 83 is Arg, and amino acid 109 is Val, where the numbering of the amino acids is as depicted in FIG. 3.

In some cases, a humanized anti-C1s antibody of the present disclosure comprises a VH region comprising the amino acid sequence depicted in FIG. 3, and set forth in SEQ ID NO:14.

In some cases, a humanized anti-C1s antibody of the present disclosure comprises a VH region comprising an amino acid sequence having at least 90%, at least 95%, at least 98%, at least 99%, or 100%, amino acid sequence identity to the amino acid sequence depicted in FIG. 4 and set forth in SEQ ID NO:16, where amino acid 1 is Gln, amino acid 5 is Val, amino acid 11 is Val, amino acid 12 is Lys, amino acid 13 is Lys, amino acid 20 is Val, amino acid 23 is Thr, amino acid 38 is Arg, amino acid 40 is Ala, amino acid 42 is Gly, amino acid 67 is Val, amino acid 75 is Thr, amino acid 76 is Ser, amino acid 80 is Met, amino acid 81 is Glu, amino acid 83 is Arg, and amino acid 109 is Val, where the numbering of the amino acids is as depicted in FIG. 4.

In some cases, a humanized anti-C1s antibody of the present disclosure comprises a VH region comprising the amino acid sequence depicted in FIG. 4, and set forth in SEQ ID NO:16.

In some cases, a humanized anti-C1s antibody of the present disclosure comprises a VH region comprising an amino acid sequence having at least 90%, at least 95%, at least 98%, at least 99%, or 100%, amino acid sequence identity to the amino acid sequence depicted in FIG. 5 and set forth in SEQ ID NO:18, where amino acid 1 is Gln, amino acid 5 is Val, amino acid 11 is Val, amino acid 12 is Lys, amino acid 13 is Lys, amino acid 20 is Val, amino acid 23 is Ala, amino acid 38 is Arg, amino acid 40 is Ala, amino acid 42 is Gly, amino acid 67 is Val, amino acid 75 is Thr, amino acid 76 is Ser, amino acid 80 is Met, amino acid 81 is Glu, amino acid 83 is Arg, and amino acid 109 is Val, where the numbering of the amino acids is as depicted in FIG. 5.

In some cases, a humanized anti-C1s antibody of the present disclosure comprises a VH region comprising the amino acid sequence depicted in FIG. 5, and set forth in SEQ ID NO:18.

In some cases, a humanized anti-C1s antibody of the present disclosure comprises a VL region comprising the following sequence:

```
                                          (SEQ ID NO: 27)
DIVLTQSPDSLAVSLGERATISCKASQSVDYDGDSYMNWYQQK(T/P)GQ

PPK(I/L)LIYDASNLESGIPARFSGSGSGTDFTLTISSLE(E/P)EDFA (I/V)YYCQQSNEDPWTFGGGTKVEIK.
```

In some cases, a humanized anti-C1s antibody of the present disclosure comprises a VL region comprising an amino acid sequence having at least 90%, at least 95%, at least 98%, at least 99%, or 100%, amino acid sequence identity to the amino acid sequence depicted in FIG. 6, and set forth in SEQ ID NO:20, where amino acid 9 is Asp, amino acid 17 is Glu, amino acid 40 is Thr, amino acid 46 is Ile, amino acid 74 is Thr, amino acid 76 is Ser, amino acid 77 is Ser, amino acid 78 is Leu, amino acid 80 is Glu, amino acid 83 is Phe, amino acid 85 is Ile, and amino acid 104 is Val, where the numbering of the amino acids is as depicted in FIG. 6.

In some cases, a humanized anti-C1s antibody of the present disclosure comprises a VL region comprising the amino acid sequence depicted in FIG. 6, and set forth in SEQ ID NO:20.

In some cases, a humanized anti-C1s antibody of the present disclosure comprises a VL region comprising an amino acid sequence having at least 90%, at least 95%, at least 98%, at least 99%, or 100%, amino acid sequence identity to the amino acid sequence depicted in FIG. 7, and set forth in SEQ ID NO:22, where amino acid 9 is Asp, amino acid 17 is Glu, amino acid 40 is Pro, amino acid 46 is Ile, amino acid 74 is Thr, amino acid 76 is Ser, amino acid 77 is Ser, amino acid 78 is Leu, amino acid 80 is Pro, amino acid 83 is Phe, amino acid 85 is Ile, and amino acid 104 is Val, where the numbering of the amino acids is as depicted in FIG. 7.

In some cases, a humanized anti-C1s antibody of the present disclosure comprises a VL region comprising the amino acid sequence depicted in FIG. 7, and set forth in SEQ ID NO:22.

In some cases, a humanized anti-C1s antibody of the present disclosure comprises a VL region comprising an amino acid sequence having at least 90%, at least 95%, at least 98%, at least 99%, or 100%, amino acid sequence identity to the amino acid sequence depicted in FIG. 8 and set forth in SEQ ID NO:24, where amino acid 9 is Asp, amino acid 17 is Glu, amino acid 40 is Pro, amino acid 46 is Leu, amino acid 74 is Thr, amino acid 76 is Ser, amino acid 77 is Ser, amino acid 78 is Leu, amino acid 80 is Pro, amino acid 83 is Phe, amino acid 85 is Val, and amino acid 104 is Val, where the numbering of the amino acids is as depicted in FIG. 8.

In some cases, a humanized anti-C1s antibody of the present disclosure comprises a VL region comprising the amino acid sequence depicted in FIG. 8, and set forth in SEQ ID NO:24.

In some cases, a humanized anti-C1s antibody of the present disclosure comprises: a) a VH variant 1 amino acid sequence depicted in FIG. 1 and as set forth in SEQ ID NO:10; and b) a VL variant 1 amino acid sequence depicted in FIG. 6 and as set forth in SEQ ID NO:20.

In some cases, a humanized anti-C1s antibody of the present disclosure comprises: a) a VH variant 1 amino acid sequence depicted in FIG. 1 and as set forth in SEQ ID NO:10; and b) a VL variant 2 amino acid sequence depicted in FIG. 7 and as set forth in SEQ ID NO:22.

In some cases, a humanized anti-C1s antibody of the present disclosure comprises: a) a VH variant 1 amino acid sequence depicted in FIG. 1 and as set forth in SEQ ID NO:10; and b) a VL variant 5 amino acid sequence depicted in FIG. 8 and as set forth in SEQ ID NO:24.

In some cases, a humanized anti-C1s antibody of the present disclosure comprises: a) a VH variant 2 amino acid sequence depicted in FIG. 2 and as set forth in SEQ ID NO:12; and b) a VL variant 1 amino acid sequence depicted in FIG. 6 and as set forth in SEQ ID NO:20.

In some cases, a humanized anti-C1s antibody of the present disclosure comprises: a) a VH variant 2 amino acid sequence depicted in FIG. 2 and as set forth in SEQ ID NO:12; and b) a VL variant 2 amino acid sequence depicted in FIG. 7 and as set forth in SEQ ID NO:22.

In some cases, a humanized anti-C1s antibody of the present disclosure comprises: a) a VH variant 2 amino acid sequence depicted in FIG. 2 and as set forth in SEQ ID NO:12; and b) a VL variant 5 amino acid sequence depicted in FIG. 8 and as set forth in SEQ ID NO:24.

In some cases, a humanized anti-C1s antibody of the present disclosure comprises: a) a VH variant 3 amino acid sequence depicted in FIG. 3 and as set forth in SEQ ID NO:14; and b) a VL variant 1 amino acid sequence depicted in FIG. 6 and as set forth in SEQ ID NO:20.

In some cases, a humanized anti-C1s antibody of the present disclosure comprises: a) a VH variant 3 amino acid sequence depicted in FIG. 3 and as set forth in SEQ ID NO:14; and b) a VL variant 2 amino acid sequence depicted in FIG. 7 and set forth in SEQ ID NO:22.

In some cases, a humanized anti-C1s antibody of the present disclosure comprises: a) a VH variant 3 amino acid sequence depicted in FIG. 3 and as set forth in SEQ ID NO:14; and b) a VL variant 5 amino acid sequence depicted in FIG. 8 and as set forth in SEQ ID NO: 24.

In some cases, a humanized anti-C1s antibody of the present disclosure comprises: a) a VH variant 4 amino acid sequence depicted in FIG. 4 and as set forth in SEQ ID NO:16; and b) a VL variant 1 amino acid sequence depicted in FIG. 6 and as set forth in SEQ ID NO:20.

In some cases, a humanized anti-C1s antibody of the present disclosure comprises: a) a VH variant 4 amino acid sequence depicted in FIG. 4 and as set forth in SEQ ID NO:16; and b) a VL variant 2 amino acid sequence depicted in FIG. 7 and as set forth in SEQ ID NO:22.

In some cases, a humanized anti-C1s antibody of the present disclosure comprises: a) a VH variant 4 amino acid sequence depicted in FIG. 4 and as set forth in SEQ ID NO:16; and b) a VL variant 5 amino acid sequence depicted in FIG. 8 and as set forth in SEQ ID NO: 24.

In some cases, a humanized anti-C1s antibody of the present disclosure comprises: a) a VH variant 5 amino acid sequence depicted in FIG. 5 and as set forth in SEQ ID NO:18; and b) a VL variant 1 amino acid sequence depicted in FIG. 6 and as set forth in SEQ ID NO:20.

In some cases, a humanized anti-C1s antibody of the present disclosure comprises: a) a VH variant 5 amino acid sequence depicted in FIG. 5 and as set forth in SEQ ID NO:18; and b) a VL variant 2 amino acid sequence depicted in FIG. 7 and as set forth in SEQ ID NO:22.

In some cases, a humanized anti-C1s antibody of the present disclosure comprises: a) a VH variant 5 amino acid sequence depicted in FIG. 5 and as set forth in SEQ ID NO:18; and b) a VL variant 5 amino acid sequence depicted in FIG. 8 and as set forth in SEQ ID NO:24.

In some embodiments, a humanized anti-C1s antibody of the present disclosure binds a complement C1s protein from an individual that has a complement system. In some embodiments, a humanized anti-C1s antibody of the present disclosure binds a complement C1s protein from a mammal, fish, or invertebrate that has a complement system. In some embodiments, a humanized anti-C1s antibody of the present disclosure binds a mammalian complement C1s protein. In some embodiments, a humanized anti-C1s antibody of the present disclosure binds a human complement C1s protein. In some embodiments, a humanized anti-C1s antibody of the present disclosure binds a rat complement C1s protein. In some embodiments, a humanized anti-C1s antibody of the present disclosure binds a complement C1s protein having the amino acid sequence depicted in FIG. 13 (SEQ ID NO:9) Amino acid sequence SEQ ID NO:9 represents *Homo sapiens* complement C1s protein, which has the amino acid sequence set forth in FIG. 13.

In some embodiments, a humanized anti-C1s antibody of the present disclosure binds a complement C1s protein with a dissociation constant ($K_D$) of no more than 2.5 nM. In some embodiments, a humanized anti-C1s antibody of the present disclosure binds a complement C1s protein with a $K_D$ of no more than 2 nM. In some embodiments, a humanized anti-C1s antibody of the present disclosure binds a complement C1s protein with a $K_D$ of no more than 1 nM. In some embodiments, a humanized anti-C1s antibody of the present disclosure binds a complement C1s protein with a $K_D$ of no more than 0.9 nM, no more than 0.8 nM, no more than 0.7 nM, no more than 0.6 nM, no more than 0.5 nM, no more than 0.4 nM, no more than 0.3 nM, no more than 0.2 nM, no more than 0.1 nM. In some embodiments, a humanized anti-C1s antibody of the present disclosure binds a complement C1s protein with a $K_D$ of no more than 0.3 nM. In some embodiments, a humanized anti-C1s antibody of the present disclosure binds a complement C1s protein with a $K_D$ of no more than 0.2 nM. In some embodiments, a humanized anti-C1s antibody of the present disclosure binds a complement C1s protein with a $K_D$ of no more than 0.1 nM. Methods to measure binding of an antibody to C1s protein can be determined by one skilled in the art.

In some embodiments, a humanized anti-C1s antibody of the present disclosure binds a complement C1s protein with a $K_D$ of no more than 90 pM, no more than 80 pM, no more than 70 pM, no more than 60 pM, no more than 50 pM, no more than 40 pM, no more than 30 pM, no more than 20 pM, no more than 10 pM, no more than 9 pM, no more than 8 pM, no more than 7 pM, no more than 6 pM, no more than 5 pM, no more than 4 pM, no more than 3 pM, no more than 2 pM, no more than 1 pM.

In some embodiments, a humanized anti-C1s antibody of the present disclosure binds a human complement C1s protein with a dissociation constant ($K_D$) of no more than 2.5 nM. In some embodiments, a humanized anti-C1s antibody of the present disclosure binds a human complement C1s protein with a $K_D$ of no more than 2 nM. In some embodiments, a humanized anti-C1s antibody of the present disclosure binds a human complement C1s protein with a $K_D$ of no more than 1 nM. In some embodiments, a humanized anti-C1s antibody of the present disclosure binds a human complement C1s protein with a $K_D$ of no more than 0.9 nM, no more than 0.8 nM, no more than 0.7 nM, no more than 0.6 nM, no more than 0.5 nM, no more than 0.4 nM, no more than 0.3 nM, no more than 0.2 nM, no more than 0.1 nM. In some embodiments, a humanized anti-C1s antibody of the present disclosure binds a human complement C1s protein with a $K_D$ of no more than 0.3 nM. In some embodiments, a humanized anti-C1s antibody of the present disclosure binds a human complement C1s protein with a $K_D$ of no more than 0.2 nM. In some embodiments, a humanized anti-C1s antibody of the present disclosure binds a human complement C1s protein with a $K_D$ of no more than 0.1 nM. Methods to measure binding of an antibody to human C1s protein can be determined by one skilled in the art. In some embodiments, a binding assay as described in the Examples is used to determine the $K_D$ between an antibody and a human C1s protein.

In some embodiments, a humanized anti-C1s antibody of the present disclosure binds a human complement C1s protein with a $K_D$ of no more than 90 pM, no more than 80 pM, no more than 70 pM, no more than 60 pM, no more than 50 pM, no more than 40 pM, no more than 30 pM, no more than 20 pM, no more than 10 pM, no more than 9 pM, no more than 8 pM, no more than 7 pM, no more than 6 pM, no more than 5 pM, no more than 4 pM, no more than 3 pM, no more than 2 pM, no more than 1 pM.

In some embodiments, a humanized anti-C1s antibody of the present disclosure inhibits the classical complement pathway with a half-maximal inhibitory concentration ($IC_{50}$) of $10^{-8}$ M or less, $5 \times 10^{-9}$ M or less, or $10^{-9}$ M or less.

Nucleic Acids, Expression Vectors, and Host Cells

The present disclosure provides a nucleic acid comprising a nucleotide sequence encoding a humanized anti-C1s antibody of the present disclosure. In some cases, a nucleic acid of the present disclosure comprises a nucleotide sequence encoding the VH region of a humanized anti-C1s antibody of the present disclosure. In some cases, a nucleic acid of the present disclosure comprises a nucleotide sequence encoding the VL region of a humanized anti-C1s antibody of the present disclosure. In some cases, a nucleic acid of the present disclosure comprises a nucleotide sequence encoding the VH region and the VL region of a humanized anti-C1s antibody of the present disclosure.

A nucleotide sequence encoding a humanized anti-C1s antibody of the present disclosure can be operably linked to one or more regulatory elements, such as a promoter and enhancer, that allow expression of the nucleotide sequence in the intended target cells (e.g., a cell that is genetically modified to synthesize the encoded antibody). Thus, in some cases, the present disclosure provides a nucleic acid comprising a nucleotide sequence encoding a humanized anti-C1s antibody of the present disclosure, where the nucleotide sequence is operably linked to one or more regulatory elements, e.g., a promoter and/or an enhancer.

Suitable promoter and enhancer elements are known in the art. Suitable promoters for use in prokaryotic host cells include, but are not limited to, a bacteriophage T7 RNA polymerase promoter; a T3 promoter; a T5 promoter; a lambda P promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; a gpt promoter; an araBAD promoter; in vivo regulated promoters, such as an ssaG promoter or a related promoter (see, e.g., U.S. Patent Publication No. 20040131637), a pagC promoter (Pulkkinen and Miller, J. Bacteriol., 1991: 173(1): 86-93; Alpuche-Aranda et al., PNAS, 1992; 89(21): 10079-83), a nirB promoter (Harborne et al. (1992) Mol. Micro. 6:2805-2813), and the like (see, e.g., Dunstan et al. (1999) Infect. Immun. 67:5133-5141; McKelvie et al. (2004) Vaccine 22:3243-3255; and Chatfield et al. (1992) Biotechnol. 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) Infect. Immun. 70:1087-1096); an rpsM promoter (see, e.g., Valdivia and Falkow (1996). Mol. Microbiol. 22:367); a tet promoter (see, e.g., Hillen, W. and Wissmann, A. (1989) In Saenger, W. and Heinemann, U. (eds), *Topics in Molecular and Structural Biology, Protein-Nucleic Acid Interaction*. Macmillan, London, UK, Vol. 10, pp. 143-162); an SP6 promoter (see, e.g., Melton et al. (1984) Nucl. Acids Res. 12:7035); and the like. Suitable strong promoters for use in prokaryotes such as *Escherichia coli* include, but are not limited to Trc, Tac, T5, T7, and $P_{Lambda}$. Non-limiting examples of operators for use in bacterial host cells include a lactose promoter operator (LacI repressor protein changes conformation when contacted with lactose, thereby preventing the LacI repressor protein from binding the operator), a tryptophan promoter operator (when complexed with tryptophan, TrpR repressor protein has a conformation that binds the operator; in the absence of tryptophan, the TrpR repressor protein has a conformation that does not bind the operator), and a tac promoter operator (see, for example, deBoer et al. (1983) Proc. Natl. Acad. Sci. U.S.A. 80:21-25).

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*).

For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

Selection of the appropriate vector and promoter is well within the level of ordinary skill in the art.

A nucleic acid comprising a nucleotide sequence encoding a humanized anti-C1s antibody of the present disclosure can be present in an expression vector and/or a cloning vector. The present disclosure provides a recombinant vector comprising a nucleic acid comprising a nucleotide sequence encoding a humanized anti-C1s antibody of the present disclosure, where the recombinant vector is a cloning vector. The present disclosure provides a recombinant vector comprising a nucleic acid comprising a nucleotide sequence encoding a humanized anti-C1s antibody of the present disclosure, where the recombinant vector is an expression vector, e.g., where the nucleotide sequence is operably linked to appropriate regulatory sequence(s) in the expression vector to ensure expression of the encoded antibody. Where a subject antibody comprises two separate polypeptides, nucleic acids encoding the two polypeptides can be cloned in the same or separate vectors to form one or more recombinant vectors. A recombinant vector can include a selectable marker, an origin of replication, and other features that provide for replication and/or maintenance of the recombinant vector (e.g., recombinant expression vector).

Large numbers of suitable vectors and promoters are known to those of skill in the art; many are commercially available for generating a subject recombinant vector. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host can be present. Suitable expression vectors include, but are not limited to, viral vectors. Examples of viral vectors include, but are not limited to, viral vectors based on: vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus (see, e.g., Miyoshi et al., PNAS 94:10319 23, 1997; Takahashi et al., J Virol 73:7812 7816, 1999), myeloproliferative sarcoma virus, and mammary tumor virus); and the like.

Host Cells

The present disclosure provides isolated genetically modified host cells (e.g., in vitro cells) that are genetically modified with a subject nucleic acid. In some embodiments, a subject isolated genetically modified host cell can produce a subject antibody. Such a cell is referred to as a "recombinant cell" or a "genetically modified host cell." A genetically modified host cell of the present disclosure comprises a nucleic acid comprising a nucleotide sequence encoding a humanized anti-C1s antibody of the present disclosure.

Suitable host cells include eukaryotic host cells, such as a mammalian cell, an insect host cell, a yeast cell; and prokaryotic cells, such as a bacterial cell. Introduction of a subject nucleic acid into the host cell can be effected, for example by calcium phosphate precipitation, DEAE dextran mediated transfection, liposome-mediated transfection, electroporation, or other known method.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like. In some cases, the cells are HEK cells. In some cases, the cells are CHO cells, e.g., CHO-K1 cells (ATCC No. CCL-61), CHO-M cells, CHO-DG44 cells (ATCC No. PTA-3356), and the like. In some embodiments, the host cell is a COS cell. In some embodiments, the host cell is a 293 cell. In some embodiments, the host cell is a CHO cell.

Suitable yeast cells include, but are not limited to, *Pichia pastoris*, *Pichia finlandica*, *Pichia trehalophila*, *Pichia koclamae*, *Pichia membranaefaciens*, *Pichia opuntiae*, *Pichia thermotolerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, *Neurospora crassa*, *Chlamydomonas reinhardtii*, and the like. In some embodiments, the host cell is a *Saccharomyces*. In some embodiments, the host cell is a *Pichia*.

Suitable prokaryotic cells include, but are not limited to, any of a variety of laboratory strains of *Escherichia coli*, *Bacillus* (e.g., *B. subtilis*), *Lactobacillus* sp., and the like. See, e.g., Carrier et al. (1992) *J. Immunol.* 148:1176-1181; U.S. Pat. No. 6,447,784; and Sizemore et al. (1995) *Science* 270:299-302. Typically, the laboratory strain is one that is non-pathogenic. In some embodiments, the host cell is *Escherichia coli*. In some embodiments, the host cell is *Bacillus subtilis*.

Pharmaceutical Compositions

The present disclosure provides compositions, including pharmaceutical compositions comprising a humanized anti-C1s antibody of the present disclosure. In general, a pharmaceutical composition, also referred to herein as a formulation, comprises an effective amount of a humanized anti-C1s antibody of the present disclosure. An "effective amount" means a dosage sufficient to produce a desired result, e.g., reduction in an adverse symptom associated with a complement-mediated disease or disorder, amelioration of a symptom of a complement-mediated disease or disorder, slowing progression of a complement-mediated disease or disorder, etc. Generally, the desired result is at least a reduction in a symptom of a complement-mediated disease or disorder, as compared to a control. In some embodiments, a humanized anti-C1s antibody of the present disclosure is formulated and/or modified to enable the antibody to cross the blood-brain barrier. In some embodiments, a humanized anti-C1s antibody of the present disclosure is delivered in such a manner as to avoid the blood-brain barrier. In some embodiments, a humanized anti-C1s antibody of the present disclosure is formulated with an agent that facilitates crossing the blood-brain barrier. In some embodiments, a humanized anti-C1s antibody of the present disclosure is fused, directly or through a linker, to a compound that promotes the crossing of the blood-brain barrier.

Formulations

In the subject methods, a humanized anti-C1s antibody of the present disclosure can be administered to the host using any convenient means capable of resulting in the desired therapeutic effect or diagnostic effect. Thus, the agent can be incorporated into a variety of formulations for therapeutic administration. More particularly, a humanized anti-C1s antibody of the present disclosure can be formulated into pharmaceutical compositions by combination with appropriate, pharmaceutically acceptable carriers, pharmaceutically acceptable diluents, or other pharmaceutically acceptable excipients and can be formulated into preparations in solid, semi-solid, liquid or gaseous forms, such as tablets, capsules, powders, granules, ointments, solutions, suppositories, injections, inhalants and aerosols. In some embodiments, a pharmaceutical composition comprises a humanized anti-C1s antibody of the present disclosure and a pharmaceutically acceptable excipient.

In pharmaceutical dosage forms, a humanized anti-C1s antibody of the present disclosure can be administered in the form of their pharmaceutically acceptable salts, or they can also be used alone or in appropriate association, as well as in combination, with other pharmaceutically active compounds. The following methods and excipients are merely exemplary and are in no way limiting.

For oral preparations, a humanized anti-C1s antibody of the present disclosure can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A humanized anti-C1s antibody of the present disclosure can be formulated into preparations for injection by dissolving, suspending or emulsifying the antibody in an aqueous or nonaqueous solvent, such as vegetable or other similar oils, propylene glycol, synthetic aliphatic acid glycerides, injectable organic esters (e.g., ethyl oleate), esters of higher aliphatic acids or propylene glycol; and if desired, with conventional additives such as solubilizers, isotonic agents, suspending agents, emulsifying agents, stabilizers and preservatives. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Furthermore, the pharmaceutical composition of the present disclosure can comprise further agents such as dopamine or psychopharmacologic drugs, depending on the intended use of the pharmaceutical composition.

Pharmaceutical compositions comprising a humanized anti-C1s antibody of the present disclosure are prepared by mixing a humanized anti-C1s antibody of the present disclosure having the desired degree of purity with optional physiologically acceptable carriers, other excipients, stabilizers, surfactants, buffers and/or tonicity agents. Acceptable carriers, other excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition can be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents can be used for the production of pharmaceutical compositions for parenteral administration; see also Chen (1992) Drug Dev Ind Pharm 18, 1311-54.

Exemplary antibody concentrations in a subject pharmaceutical composition can range from about 1 mg/mL to about 200 mg/mL or from about 50 mg/mL to about 200 mg/mL, or from about 150 mg/mL to about 200 mg/mL.

An aqueous formulation of a humanized anti-C1s antibody of the present disclosure can be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

A tonicity agent can be included in the antibody formulation to modulate the tonicity of the formulation. Exemplary tonicity agents include sodium chloride, potassium chloride, glycerin and any component from the group of amino acids, sugars as well as combinations thereof. In some embodiments, the aqueous formulation is isotonic, although hypertonic or hypotonic solutions can be suitable. The term "isotonic" denotes a solution having the same tonicity as some other solution with which it is compared, such as a physiological salt solution or serum. Tonicity agents can be used in an amount of about 5 mM to about 350 mM, e.g., in an amount of 100 mM to 350 nM.

A surfactant can also be added to the antibody formulation to reduce aggregation of the formulated antibody and/or minimize the formation of particulates in the formulation and/or reduce adsorption. Exemplary surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, (sold under the trademark Tween 20™) and polysorbate 80 (sold under the trademark Tween 80™). Examples of suitable polyethylene-polypropylene copolymers are those sold under the names Pluronic® F68 or Poloxamer 188™. Examples of suitable Polyoxyethylene alkyl ethers are those sold under the trademark Brij™. Exemplary concentrations of surfactant can range from about 0.001% to about 1% w/v.

A lyoprotectant can also be added in order to protect the labile active ingredient (e.g. a protein) against destabilizing conditions during the lyophilization process. For example, known lyoprotectants include sugars (including glucose and sucrose); polyols (including mannitol, sorbitol and glycerol); and amino acids (including alanine, glycine and glutamic acid). Lyoprotectants can be included in an amount of about 10 mM to 500 nM.

In some embodiments, a subject formulation includes a humanized anti-C1s antibody of the present disclosure, and one or more of the above-identified agents (e.g., a surfactant, a buffer, a stabilizer, a tonicity agent) and is essentially free of one or more preservatives, such as ethanol, benzyl alcohol, phenol, m-cresol, p-chlor-m-cresol, methyl or propyl parabens, benzalkonium chloride, and combinations thereof. In other embodiments, a preservative is included in the formulation, e.g., at concentrations ranging from about 0.001 to about 2% (w/v).

For example, a subject formulation can be a liquid or lyophilized formulation suitable for parenteral administration, and can comprise: about 1 mg/mL to about 200 mg/mL of a humanized anti-C1s antibody of the present disclosure; about 0.001% to about 1% of at least one surfactant; about 1 mM to about 100 mM of a buffer; optionally about 10 mM to about 500 mM of a stabilizer; and about 5 mM to about 305 mM of a tonicity agent; and has a pH of about 4.0 to about 7.0.

As another example, a subject parenteral formulation is a liquid or lyophilized formulation comprising: about 1 mg/mL to about 200 mg/mL of a humanized anti-C1s antibody of the present disclosure; 0.04% Tween 20 w/v; 20 mM L-histidine; and 250 mM Sucrose; and has a pH of 5.5.

As another example, a subject parenteral formulation comprises a lyophilized formulation comprising: 1) 15 mg/mL of a subject antibody; 0.04% Tween 20 w/v; 20 mM L-histidine; and 250 mM sucrose; and has a pH of 5.5; or 2) 75 mg/mL of a subject antibody; 0.04% Tween 20 w/v; 20 mM L-histidine; and 250 mM sucrose; and has a pH of 5.5; or 3) 75 mg/mL of a subject antibody; 0.02% Tween 20 w/v; 20 mM L-histidine; and 250 mM sucrose; and has a pH of 5.5; or 4) 75 mg/mL of a subject antibody; 0.04% Tween 20 w/v; 20 mM L-histidine; and 250 mM trehalose; and has a pH of 5.5; or 5) 75 mg/mL of a subject antibody; 0.02% Tween 20 w/v; 20 mM L-histidine; and 250 mM trehalose; and has a pH of 5.5.

As another example, a subject parenteral formulation is a liquid formulation comprising: 1) 7.5 mg/mL of a subject antibody; 0.02% Tween 20 w/v; 120 mM L-histidine; and 250 125 mM sucrose; and has a pH of 5.5; or 2) 37.5 mg/mL of a subject antibody; 0.02% Tween 20 w/v; 10 mM L-histidine; and 125 mM sucrose; and has a pH of 5.5; or 3) 37.5 mg/mL of a subject antibody; 0.01% Tween 20 w/v; 10 mM L-histidine; and 125 mM sucrose; and has a pH of 5.5; or 4) 37.5 mg/mL of a subject antibody; 0.02% Tween 20 w/v; 10 mM L-histidine; 125 mM trehalose; and has a pH of 5.5; or 5) 37.5 mg/mL of a subject antibody; 0.01% Tween 20 w/v; 10 mM L-histidine; and 125 mM trehalose; and has a pH of 5.5; or 6) 5 mg/mL of a subject antibody; 0.02% Tween 20 w/v; 20 mM L-histidine; and 250 mM trehalose; and has a pH of 5.5; or 7) 75 mg/mL of a subject antibody; 0.02% Tween 20 w/v; 20 mM L-histidine; and 250 mM mannitol; and has a pH of 5.5; or 8) 75 mg/mL of a subject antibody; 0.02% Tween 20 w/v; 20 mM L histidine; and 140 mM sodium chloride; and has a pH of 5.5; or 9) 150 mg/mL of a subject antibody; 0.02% Tween 20 w/v; 20 mM L-histidine; and 250 mM trehalose; and has a pH of 5.5; or 10) 150 mg/mL of a subject antibody; 0.02% Tween 20 w/v; 20 mM L-histidine; and 250 mM mannitol; and has a pH of 5.5; or 11) 150 mg/mL of a subject antibody; 0.02% Tween 20 w/v; 20 mM L-histidine; and 140 mM sodium chloride; and has a pH of 5.5; or 12) 10 mg/mL of a subject antibody; 0.01% Tween 20 w/v; 20 mM L-histidine; and 40 mM sodium chloride; and has a pH of 5.5.

A subject antibody can be utilized in aerosol formulation to be administered via inhalation. A subject antibody can be formulated into pressurized acceptable propellants such as dichlorodifluoromethane, propane, nitrogen and the like. Aerosol formulations such as nasal spray formulations include purified aqueous or other solutions of the active agent with preservative agents and isotonic agents. Such formulations are adjusted to a pH and isotonic state compatible with the nasal mucous membranes.

Unit dosage forms for oral administration such as syrups, elixirs, and suspensions can be provided wherein each dosage unit, for example, teaspoonful, tablespoonful, or tablet, contains a predetermined amount of the composition. Similarly, unit dosage forms for injection or intravenous administration can comprise a subject antibody in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of a humanized anti-C1s antibody of the present disclosure, calculated in an amount sufficient to produce the desired effect in association with a pharmaceutically acceptable diluent, carrier or vehicle. The specifications for a subject antibody can depend on the particular antibody employed and the effect to be achieved, and the pharmacodynamics associated with each antibody in the host.

Other modes of administration will also find use with a method of the present disclosure. For instance, a subject antibody can be formulated in suppositories and, in some cases, aerosol and intranasal compositions. For suppositories, the vehicle composition will include traditional binders and carriers such as, polyalkylene glycols, or triglycerides. Such suppositories can be formed from mixtures containing the active ingredient in the range of about 0.5% to about 10% (w/w), e.g., about 1% to about 2%.

Intranasal formulations will usually include vehicles that neither cause irritation to the nasal mucosa nor significantly disturb ciliary function. Diluents such as water, aqueous saline or other known substances can be employed. The nasal formulations can also contain preservatives such as, but not limited to, chlorobutanol and benzalkonium chloride. A surfactant can be present to enhance absorption of the subject antibody by the nasal mucosa.

A subject antibody can be administered as an injectable formulation. Typically, injectable compositions are prepared as liquid solutions or suspensions; solid forms suitable for solution in, or suspension in, liquid vehicles prior to injection can also be prepared. The preparation can also be emulsified or the antibody encapsulated in liposome vehicles.

Suitable excipient vehicles are, for example, water, saline, dextrose, glycerol, ethanol, or the like, and combinations thereof. In addition, if desired, the vehicle can contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of a subject antibody adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, a humanized anti-C1s antibody of the present disclosure is formulated in a controlled release formulation. Sustained-release preparations can be prepared using methods well known in the art. Suitable examples of sustained-release preparations include semipermeable matrices of solid hydrophobic polymers containing the antibody in which the matrices are in the form of shaped articles, e.g. films or microcapsules. Examples of sustained-release matrices include polyesters, copolymers of L-glutamic acid and ethyl-L-glutamate, non-degradable ethylene-vinyl acetate, hydrogels, polylactides, degradable lactic acid-glycolic acid copolymers and poly-D-(−)-3-hydroxybutyric acid. Possible loss of biological activity and possible changes in immunogenicity of antibodies comprised in sustained-release preparations can be prevented by using appropriate additives, by controlling moisture content and by developing specific polymer matrix compositions.

Controlled release within the scope of the present disclosure can be taken to mean any one of a number of extended release dosage forms. The following terms can be considered to be substantially equivalent to controlled release, for the purposes of the present disclosure: continuous release, controlled release, delayed release, depot, extended release, gradual release, immediate release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, and sustained-action medications. Further discussions of these terms can be found in Lesczek Krowczynski, *Extended-Release Dosage Forms*, 1987 (CRC Press, Inc.).

The various controlled release technologies cover a very broad spectrum of drug dosage forms. Controlled release technologies include, but are not limited to physical systems and chemical systems.

Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable), and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release can be found in Agis F. Kydonieus, *Controlled Release Technologies: Methods, Theory and Applications*, 1980 (CRC Press, Inc.).

There are a number of controlled release drug formulations that are developed for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems can be found in Yie W. Chien, *Novel Drug Delivery Systems*, 1992 (Marcel Dekker, Inc.).

Dosages

A suitable dosage can be determined by an attending physician or other qualified medical personnel, based on various clinical factors. As is well known in the medical arts, dosages for any one patient depend upon many factors, including the patient's size, body surface area, age, the particular compound to be administered, sex of the patient, time, and route of administration, general health, and other drugs being administered concurrently. A subject antibody can be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 µg to 10 mg per kilogram of body weight per minute.

In some embodiments, a dose of a humanized anti-C1s antibody of the present disclosure is in the range of 0.001 µg to 1000 µg; however, doses below or above this exemplary range are envisioned, especially considering the aforementioned factors. In some embodiments, the dosage can range, e.g., from about 0.0001 to 100 mg/kg, or from about 0.01 to 5 mg/kg (e.g., 0.02 mg/kg, 0.25 mg/kg, 0.5 mg/kg, 0.75 mg/kg, 1 mg/kg, 2 mg/kg, etc.) body weight. For example dosages can be 1 mg/kg body weight or 10 mg/kg body weight or within the range of 1-10 mg/kg, or at least 1 mg/kg. Doses intermediate in the above ranges are also intended to be within the scope of the invention.

In some embodiments, a humanized anti-C1s antibody of the present disclosure is administered in an amount that provides for a peak serum concentration of from about 1 µg/ml to about 1 mg/ml, e.g., from about 1 µg/ml to about 2.5 µg/ml, from about 2.5 µg/ml to about 5 µg/ml, from about 5 µg/ml to about 7.5 µg/ml, from about 7.5 µg/ml to about 10 µg/ml, from about 10 µg/ml to about 25 µg/ml, from about 25 µg/ml to about 50 µg/ml, from about 50 µg/ml to about 100 µg/ml, from about 100 µg/ml to about 250

μg/ml, from about 250 μg/ml to about 500 μg/ml, from about 500 μg/ml to about 750 μg/ml, or from about 750 μg/ml to about 1000 μg/ml. In some embodiments, a subject anti-C1s antibody is administered in an amount that provides for a peak serum concentration of greater than 1 mg/ml, e.g., from about 1 mg/ml to about 2 mg/ml, from about 2 mg/ml to about 5 mg/ml, or from about 5 mg/ml to about 10 mg/ml. A humanized antibody of the present disclosure can be administered according to any schedule and for any period of time.

Those of skill will readily appreciate that dose levels and administration schedules can vary as a function of the specific antibody, the severity of the symptoms and the susceptibility of the subject to side effects. Preferred dosages and administration schedules for a given compound are readily determinable by those of skill in the art by a variety of means.

Routes of Administration

A subject antibody is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, intrathecal, intracranial, subcutaneous, intradermal, topical, intravenous, intraperitoneal, intraarterial (e.g., via the carotid artery), spinal or brain delivery, rectal, nasal, oral, and other enteral and parenteral routes of administration. Routes of administration can be combined, if desired, or adjusted depending upon the antibody and/or the desired effect. A subject antibody composition can be administered in a single dose or in multiple doses. In some embodiments, a subject antibody composition is administered orally. In some embodiments, a subject antibody composition is administered via an inhalational route. In some embodiments, a subject antibody composition is administered intranasally. In some embodiments, a subject antibody composition is administered locally. In some embodiments, a subject antibody composition is administered intracranially. In some embodiments, a subject antibody composition is administered intravenously. In some embodiments, a subject antibody composition is administered subcutaneously. In some embodiments, a subject antibody composition is administered intramuscularly. In some embodiments, a subject antibody composition is administered intrathecally.

An antibody of the present disclosure can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, intrathecal, and intravenous routes, i.e., any route of administration other than through the alimentary canal. Parenteral administration can be carried to effect systemic or local delivery of a subject antibody. Where systemic delivery is desired, administration typically involves invasive or systemically absorbed topical or mucosal administration of pharmaceutical preparations.

A subject antibody can also be delivered to the subject by enteral administration. Enteral routes of administration include, but are not necessarily limited to, oral and rectal (e.g., using a suppository) delivery.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as a complement-mediated disease or disorder. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

In some embodiments, a humanized anti-C1s antibody of the present disclosure is administered by injection and/or delivery, e.g., to a site in a brain artery or directly into brain tissue. A subject humanized antibody can also be administered directly to a target site e.g., by biolistic delivery to the target site.

A variety of hosts (wherein the term "host" is used interchangeably herein with the terms "subject," "individual," and "patient") are treatable according to the subject methods. Generally such hosts are "mammals" or "mammalian," where these terms are used broadly to describe organisms which are within the class mammalia, including the orders carnivore (e.g., cats), herbivores (e.g., cattle, horses, and sheep), omnivores (e.g., dogs, goats, and pigs), rodentia (e.g., mice, guinea pigs, and rats), and primates (e.g., humans, chimpanzees, and monkeys). In some embodiments, the host is an individual that has a complement system, such as a mammal, fish, or invertebrate. In some embodiments, the host is a complement system-containing mammal, fish, or invertebrate companion animal, agricultural animal, work animal, zoo animal, or lab animal. In some embodiments, the host is human.

The embodiments include compositions comprising a container suitable for containing a composition comprising a subject anti-C1s antibody for administration to an individual. For example, a subject antibody can be disposed within a container suitable for containing a pharmaceutical composition. The container can be, for example, a bottle (e.g., with a closure device, such as a cap), a blister pack (e.g., which can provide for enclosure of one or more doses per blister), a vial, flexible packaging (e.g., sealed Mylar or plastic bags), an ampule (for single doses in solution), a dropper, a syringe, thin film, a tube and the like. In some embodiments, a container, such as a sterile container, comprises a subject pharmaceutical composition. In some embodiments the container is a bottle or a syringe. In some embodiments the container is a bottle. In some embodiments the container is a syringe.

Kits with unit doses of a humanized anti-C1s antibody of the present disclosure, e.g. in oral or injectable doses, are provided. In such kits, in addition to the containers containing the unit doses will be an informational package insert describing the use and attendant benefits of the antibody in treating pathological condition of interest. Preferred compounds and unit doses are those described herein above.

Methods of Treating a Complement-Mediated Disease or Disorder

The present disclosure provides methods of treating a complement-mediated disease or disorder. The methods generally involve administering an effective amount of a humanized anti-C1s antibody of the present disclosure, or a pharmaceutical composition comprising such an antibody, to an individual in need thereof. In some cases, administration of a subject anti-C1s antibody modulates the activity of complement C1s in a cell, a tissue, a fluid, or an organ of an individual, and treats the complement-mediated disease or disorder. The present disclosure provides methods of inhibiting activation of complement component C4 in an individual, the methods comprising administering to the individual an effective amount of a humanized anti-C1s antibody of the present disclosure or a pharmaceutical composition comprising such an antibody. The present disclosure provides methods of inhibiting complement C1s activity in an individual, the methods comprising administering to the individual an effective amount of a humanized anti-C1s antibody of the present disclosure or a pharmaceutical composition comprising such an antibody. The present disclosure provides methods of reducing the level of a complement component cleavage product in an individual (e.g., in a fluid, tissue, or organ in an individual), the methods comprising administering to the individual an effective amount of a humanized anti-C1s antibody of the present disclosure or a pharmaceutical composition comprising such an antibody.

In some cases, a method of the present disclosure to treat an individual having a complement-mediated disease or disorder comprises administering to the individual an effective amount of a humanized anti-C1s antibody of the present disclosure or an effective amount of a pharmaceutical composition comprising: a) a humanized anti-C1s antibody of the present disclosure; and a pharmaceutically acceptable excipient suitable for administration to such individual. In some embodiments, the individual is a mammal. In some embodiments, the individual is a human Administration can be by any route known to those skilled in the art, including those disclosed herein. In some embodiments, administering is intravenous. In some embodiments, administering is intrathecal. In some embodiments, administering is subcutaneous. In some embodiments, administering intramuscular.

In some cases, an "effective amount" of a humanized anti-C1s antibody of the present disclosure, or an "effective amount" of a subject pharmaceutical composition comprising a humanized anti-C1s antibody of the present disclosure, is an amount that, when administered in one or more doses to an individual in need thereof, reduces the level of a complement component cleavage product in the individual (e.g., in a fluid, tissue, or organ in the individual). In some cases, an "effective amount" of a humanized anti-C1s antibody of the present disclosure, or an "effective amount" of a subject pharmaceutical composition comprising a humanized anti-C1s antibody of the present disclosure, is an amount that, when administered in one or more doses to an individual in need thereof, reduces the level of a complement component cleavage product in the individual (e.g., in a fluid, tissue, or organ in the individual) by at least 10%, at least 20%, at least 30%, at least 40%, at least 50%, at least 60%, at least 65%, at least 70%, at least 75%, at least 80%, at least 85%, at least 90%, at least 95%, or 100%, compared to the level of the complement component cleavage product in the fluid, tissue, or organ in the absence of treatment with the humanized anti-C1s antibody, e.g., before treatment with the humanized anti-C1s antibody. In some embodiments, the individual is a mammal. In some embodiments, the individual is a human Administering can be by any route known to those skilled in the art, including those disclosed herein. In some embodiments, administering is intravenous. In some embodiments, the route of administration is intrathecal. In some embodiments, the route of administration is intravenous. In some embodiments, the route of administration is subcutaneous. In some embodiments, the route of administration is intramuscular.

In some cases, an "effective amount" of a humanized anti-C1s antibody of the present disclosure, or an "effective amount" of a subject pharmaceutical composition comprising a humanized anti-C1s antibody of the present disclosure, is an amount that, when administered in one or more doses to an individual in need thereof, reduces the activity of the classical complement pathway in the individual (e.g., in a fluid, tissue, or organ in the individual). In some cases, an "effective amount" of a humanized anti-C1s antibody of the present disclosure, or an "effective amount" of a subject pharmaceutical composition comprising a humanized anti-C1s antibody of the present disclosure, is an amount that, when administered in one or more doses to an individual in need thereof, reduces, within about 48 hours, within about 24 hours, within about 12 hours, within about 8 hours, or within about 4 hours of administration of the humanized anti-C1s antibody, the activity of the classical complement pathway in the individual (e.g., in a fluid, tissue, or organ in the individual), by at least 10%, at least 20%, at least 30%, at least 40%, at least 50%, at least 60%, at least 65%, at least 70%, at least 75%, at least 80%, at least 85%, at least 90%, at least 95%, or 100%, compared to the activity of the classical complement pathway in the fluid, tissue, or organ in the absence of treatment with the humanized anti-C1s antibody, e.g., before treatment with the humanized anti-C1s antibody. In some embodiments, the individual is a mammal. In some embodiments, the individual is a human. Administration of the humanized anti-C1s antibody can be by any route known to those skilled in the art, including those disclosed herein. In some embodiments, the route of administration is intrathecal. In some embodiments, the route of administration is intravenous. In some embodiments, the route of administration is subcutaneous. In some embodiments, the route of administration is intramuscular. The level of activity of the classical complement pathway can be determined using any of a variety of methods. As one non-limiting example, the activity of the classical complement pathway can be determined ex vivo, e.g., by determining the level of activity of the classical complement pathway in a blood, serum, or plasma sample obtained from the individual. For example, the classical complement pathway in the blood, serum, or plasma sample can be activated ex vivo, and the amount of a complement component cleavage product (such as C5b-9) generated by such activation can be determined.

In some cases, an "effective amount" of a humanized anti-C1s antibody of the present disclosure, or an "effective amount" of a subject pharmaceutical composition comprising a humanized anti-C1s antibody of the present disclosure, is an amount that, when administered in one or more doses to an individual in need thereof, reduces the activity of the classical complement pathway in the individual (e.g., in a fluid, tissue, or organ in the individual). In some cases, an "effective amount" of a humanized anti-C1s antibody of the present disclosure, or an "effective amount" of a subject pharmaceutical composition comprising a humanized anti-C1s antibody of the present disclosure, is an amount that, when administered in one or more doses to an individual in need thereof, reduces, within about 48 hours, within about 24 hours, within about 12 hours, within about 8 hours, or within about 4 hours of administration of the humanized anti-C1s antibody, the level of activity of the classical complement pathway in the individual (e.g., in a fluid, tissue, or organ in the individual), by at least 50%, at least 60%, at least 65%, at least 70%, at least 75%, at least 80%, at least 85%, at least 90%, at least 95%, or 100%, compared to the level of the activity of the classical complement pathway in the fluid, tissue, or organ in the absence of treatment with the humanized anti-C1s antibody, e.g., before treatment with the humanized anti-C1s antibody. In some embodiments, the individual is a mammal. In some embodiments, the individual is a human. Administration of the humanized anti-C1s antibody can be by any route known to those skilled in the art, including those disclosed herein. In some embodiments, the route of administration is intrathecal. In some embodiments, the route of administration is intravenous. In some embodiments, the route of administration is subcutaneous. In some embodiments, the route of administration is intramuscular.

In some cases, an "effective amount" of a humanized anti-C1s antibody of the present disclosure, or an "effective amount" of a subject pharmaceutical composition comprising a humanized anti-C1s antibody of the present disclosure, is an amount that, when administered in one or more doses to an individual in need thereof, reduces the activity of the classical complement pathway in the individual (e.g., in a fluid, tissue, or organ in the individual). In some cases, an "effective amount" of a humanized anti-C1s antibody of the present disclosure, or an "effective amount" of a subject pharmaceutical composition comprising a humanized anti-C1s antibody of the present disclosure, is an amount that, when administered in one or more doses to an individual in need thereof, maintains a reduction in the level of activity of the classical complement pathway in the individual (e.g., in a fluid, tissue, or organ in the individual) of at least 10%, at least 20%, at least 30%, at least 40%, at least 50%, at least 60%, at least 65%, at least 70%, at least 75%, at least 80%, at least 85%, at least 90%, at least 95%, or 100%, compared to the level of the activity of the classical complement pathway in the fluid, tissue, or organ in the absence of treatment with the humanized anti-C1s antibody, e.g., before treatment with the humanized anti-C1s antibody, where the reduction is maintained for a period of time of from about 4 hours to about 30 days (e.g., from 4 hours to 8 hours, from 8 hours to 24 hours, from 2 days to 4 days, from 4 days to 7 days, from 7 days to 14 days, from 14 days to 21 days, or from 21 days to 30 days). In some embodiments, the individual is a mammal. In some embodiments, the individual is a human. Administration of the humanized anti-C1s antibody can be by any route known to those skilled in the art, including those disclosed herein. In some embodiments, the route of administration is intrathecal. In some embodiments, the route of administration is intravenous. In some embodiments, the route of administration is subcutaneous. In some embodiments, the route of administration is intramuscular.

In some cases, an "effective amount" of a humanized anti-C1s antibody of the present disclosure, or an "effective amount" of a subject pharmaceutical composition comprising a humanized anti-C1s antibody of the present disclosure, is an amount that, when administered in one or more doses to an individual in need thereof, reduces the activity of the classical complement pathway in the individual (e.g., in a fluid, tissue, or organ in the individual). In some cases, an "effective amount" of a humanized anti-C1s antibody of the present disclosure, or an "effective amount" of a subject pharmaceutical composition comprising a humanized anti-C1s antibody of the present disclosure, is an amount that, when administered in one or more doses to an individual in need thereof, maintains a reduction in the level of activity of the classical complement pathway in the individual (e.g., in a fluid, tissue, or organ in the individual) of at least 50%, at least 60%, at least 65%, at least 70%, at least 75%, at least 80%, at least 85%, at least 90%, at least 95%, or 100%, compared to the level of activity of the classical complement pathway in the fluid, tissue, or organ in the absence of treatment with the humanized anti-C1s antibody, e.g., before treatment with the humanized anti-C1s antibody, where the reduction is maintained for a period of time of from about 4 hours to about 21 days (e.g., from 4 hours to 8 hours, from 8 hours to 24 hours, from 2 days to 4 days, from 4 days to 7 days, from 7 days to 14 days, or from 14 days to 21 days). In some embodiments, the individual is a mammal. In some embodiments, the individual is a human. Administration of the humanized anti-C1s antibody can be by any route known to those skilled in the art, including those disclosed herein. In some embodiments, the route of administration is intrathecal. In some embodiments, the route of administration is intravenous. In some embodiments, the route of administration is subcutaneous. In some embodiments, the route of administration is intramuscular.

In some cases, an "effective amount" of a humanized anti-C1s antibody of the present disclosure, or an "effective amount" of a subject pharmaceutical composition comprising a humanized anti-C1s antibody of the present disclosure, is an amount that, when administered in one or more doses to an individual in need thereof, reduces the level of a complement component cleavage product in the individual (e.g., in a fluid, tissue, or organ in the individual). In some cases, an "effective amount" of a humanized anti-C1s antibody of the present disclosure, or an "effective amount" of a subject pharmaceutical composition comprising a humanized anti-C1s antibody of the present disclosure, is an amount that, when administered in one or more doses to an individual in need thereof, reduces, within about 48 hours, within about 24 hours, within about 12 hours, within about 8 hours, or within about 4 hours of administration of the humanized anti-C1s antibody, the level of a complement component cleavage product in the individual (e.g., in a fluid, tissue, or organ in the individual), by at least 10%, at least 20%, at least 30%, at least 40%, at least 50%, at least 60%, at least 65%, at least 70%, at least 75%, at least 80%, at least 85%, at least 90%, at least 95%, or 100%, compared to the level of the complement component cleavage product in the fluid, tissue, or organ in the absence of treatment with the humanized anti-C1s antibody, e.g., before treatment with the humanized anti-C1s antibody. In some embodiments, the individual is a mammal. In some embodiments, the individual is a human Administration of the humanized anti-C1s antibody can be by any route known to those skilled in the art, including those disclosed herein. In some embodiments, the route of administration is intrathecal. In some embodiments, the route of administration is intravenous. In some embodiments, the route of administration is subcutaneous. In some embodiments, the route of administration is intramuscular.

In some cases, an "effective amount" of a humanized anti-C1s antibody of the present disclosure, or an "effective amount" of a subject pharmaceutical composition comprising a humanized anti-C1s antibody of the present disclosure, is an amount that, when administered in one or more doses to an individual in need thereof, reduces the level of a complement component cleavage product in the individual (e.g., in a fluid, tissue, or organ in the individual). In some cases, an "effective amount" of a humanized anti-C1s antibody of the present disclosure, or an "effective amount" of a subject pharmaceutical composition comprising a humanized anti-C1s antibody of the present disclosure, is an amount that, when administered in one or more doses to an individual in need thereof, reduces, within about 48 hours, within about 24 hours, within about 12 hours, within about 8 hours, or within about 4 hours of administration of the humanized anti-C1s antibody, the level of a complement component cleavage product in the individual (e.g., in a fluid, tissue, or organ in the individual), by at least 50%, at least 60%, at least 65%, at least 70%, at least 75%, at least 80%, at least 85%, at least 90%, at least 95%, or 100%, compared to the level of the complement component cleavage product in the fluid, tissue, or organ in the absence of treatment with the humanized anti-C1s antibody, e.g., before treatment with the humanized anti-C1s antibody. In some embodiments, the individual is a mammal. In some embodiments, the individual is a human. Administration of the humanized anti-C1s antibody can be by any route known to those skilled in the art, including those disclosed herein. In some embodiments, the route of administration is intrathecal. In some embodiments, the route of administration is intravenous. In some embodiments, the route of administration is subcutaneous. In some embodiments, the route of administration is intramuscular.

In some cases, an "effective amount" of a humanized anti-C1s antibody of the present disclosure, or an "effective amount" of a subject pharmaceutical composition comprising a humanized anti-C1s antibody of the present disclosure, is an amount that, when administered in one or more doses to an individual in need thereof, reduces the level of a complement component cleavage product in the individual (e.g., in a fluid, tissue, or organ in the individual). In some cases, an "effective amount" of a humanized anti-C1s antibody of the present disclosure, or an "effective amount" of a subject pharmaceutical composition comprising a humanized anti-C1s antibody of the present disclosure, is an amount that, when administered in one or more doses to an individual in need thereof, maintains a reduction in the level of a complement component cleavage product in the individual (e.g., in a fluid, tissue, or organ in the individual) of at least 10%, at least 20%, at least 30%, at least 40%, at least 50%, at least 60%, at least 65%, at least 70%, at least 75%, at least 80%, at least 85%, at least 90%, at least 95%, or 100%, compared to the level of the complement component cleavage product in the fluid, tissue, or organ in the absence of treatment with the humanized anti-C1s antibody, e.g., before treatment with the humanized anti-C1s antibody, where the reduction is maintained for a period of time of from about 4 hours to about 30 days (e.g., from 4 hours to 8 hours, from 8 hours to 24 hours, from 2 days to 4 days, from 4 days to 7 days, from 7 days to 14 days, from 14 days to 21 days, or from 21 days to 30 days). In some embodiments, the individual is a mammal. In some embodiments, the individual is a human. Administration of the humanized anti-C1s antibody can be by any route known to those skilled in the art, including those disclosed herein. In some embodiments, the route of administration is intrathecal. In some embodiments, the route of administration is intravenous. In some embodiments, the route of administration is subcutaneous. In some embodiments, the route of administration is intramuscular.

In some cases, an "effective amount" of a humanized anti-C1s antibody of the present disclosure, or an "effective amount" of a subject pharmaceutical composition comprising a humanized anti-C1s antibody of the present disclosure, is an amount that, when administered in one or more doses to an individual in need thereof, reduces the level of a complement component cleavage product in the individual (e.g., in a fluid, tissue, or organ in the individual). In some cases, an "effective amount" of a humanized anti-C1s antibody of the present disclosure, or an "effective amount" of a subject pharmaceutical composition comprising a humanized anti-C1s antibody of the present disclosure, is an amount that, when administered in one or more doses to an individual in need thereof, maintains a reduction in the level of a complement component cleavage product in the individual (e.g., in a fluid, tissue, or organ in the individual) of at least 50%, at least 60%, at least 65%, at least 70%, at least 75%, at least 80%, at least 85%, at least 90%, at least 95%, or 100%, compared to the level of the complement component cleavage product in the fluid, tissue, or organ in the absence of treatment with the humanized anti-C1s antibody, e.g., before treatment with the humanized anti-C1s antibody, where the reduction is maintained for a period of time of from about 4 hours to about 21 days (e.g., from 4 hours to 8 hours, from 8 hours to 24 hours, from 2 days to 4 days, from 4 days to 7 days, from 7 days to 14 days, or from 14 days to 21 days). In some embodiments, the individual is a mammal. In some embodiments, the individual is a human. Administration of the humanized anti-C1s antibody can be by any route known to those skilled in the art, including those disclosed herein. In some embodiments, the route of administration is intrathecal. In some embodiments, the route of administration is intravenous. In some embodiments, the route of administration is subcutaneous. In some embodiments, the route of administration is intramuscular.

In some cases, an "effective amount" of a humanized anti-C1s antibody of the present disclosure, or an "effective amount" of a subject pharmaceutical composition comprising a humanized anti-C1s antibody of the present disclosure, is an amount that, when administered in one or more doses to an individual in need thereof, reduces production of C4b2a (i.e., complement C4b and C2a complex; also known as "C3 convertase") in the individual (or in a fluid, tissue, or organ of the individual) by at least 10%, at least 20%, at least 30%, at least 40%, at least 50%, at least 60%, at least 65%, at least 70%, at least 75%, at least 80%, at least 85%, at least 90%, at least 95%, or 100%, compared to the amount of C4b2a produced in the individual, or the fluid, tissue, or organ, in the absence of treatment with the humanized anti-C1s antibody, e.g., before treatment with the humanized anti-C1s antibody. In some embodiments, the individual is a mammal. In some embodiments, the individual is a human. Administering can be by any route known to those skilled in the art, including those disclosed herein. In some embodiments, administering is intravenous. In some embodiments, the route of administration is intrathecal. In some embodiments, the route of administration is intravenous. In some embodiments, the route of administration is subcutaneous. In some embodiments, the route of administration is intramuscular.

The present disclosure provides a method to modulate complement activation. In some embodiments the method inhibits complement activation, for example to reduce production of C4b2a. In some embodiments, the present disclosure provides a method to modulate complement activation in an individual having a complement-mediated disease or disorder, the method comprising administering to the individual a humanized anti-C1s antibody of the present disclosure or a pharmaceutical composition of the present disclosure, wherein the pharmaceutical composition comprises a humanized anti-C1s antibody of the present disclosure. In some embodiments such a method inhibits complement activation. In some embodiments, the individual is a mammal. In some embodiments, the individual is a human Administering can be by any route known to those skilled in the art, including those disclosed herein. In some embodiments, administering is intravenous. In some embodiments, administering is intrathecal. In some embodiments, administering is subcutaneous. In some embodiments, the route of administration is intramuscular.

A complement-mediated disease or disorder is a disorder characterized by an abnormal amount of complement C1s or an abnormal level of complement C1s proteolytic activity in a cell, a tissue, a fluid, or an organ of an individual.

In some cases, a complement-mediated disease or disorder is characterized by the presence in a cell, a tissue, or a fluid of an elevated (higher than normal) amount of C1s or of an elevated level of complement C1s activity. For example, in some cases, a complement-mediated disease or disorder is characterized by the presence in brain tissue and/or cerebrospinal fluid of an elevated amount and/or an elevated activity of C1s. A "higher than normal" amount of C1s in a cell, a tissue, or a fluid indicates that the amount of C1s in the cell, tissue or fluid is higher than a normal, control level, e.g., higher than a normal, control level for an individual or population of individuals of the same age group. A "higher than normal" level of C1s activity in a cell, a tissue, an organ, or a fluid indicates that the proteolytic cleavage effected by C1s in the cell, tissue, organ, or fluid is higher than a normal, control level, e.g., higher than a normal, control level for an individual or population of individuals of the same age group. In some cases, an individual having a complement-mediated disease or disorder exhibits one or more additional symptoms of such a disease or disorder.

In other cases, a complement-mediated disease or disorder is characterized by the presence in a cell, a tissue, or a fluid of a lower than normal amount of C1s or of a lower level of complement C1s activity. For example, in some cases, a complement-mediated disease or disorder is characterized by the presence in brain tissue and/or cerebrospinal fluid of a lower amount and/or a lower activity of C1s. A "lower than normal" amount of C1s in a cell, a tissue, or a fluid indicates that the amount of C1s in the cell, tissue or fluid is lower than a normal, control level, e.g., lower than a normal, control level for an individual or population of individuals of the same age group. A "lower than normal" level of C1s activity in a cell, a tissue, or a fluid indicates that the proteolytic cleavage effected by C1s in the cell, tissue or fluid is lower than a normal, control level, e.g., lower than a normal, control level for an individual or population of individuals of the same age group. In some cases, an individual having a complement-mediated disease or disorder exhibits one or more additional symptoms of such a disease or disorder.

A complement-mediated disease or disorder is a disease or disorder in which the amount or activity of complement C1s is such as to cause disease or disorder in an individual. In some embodiments, the complement-mediated disease or disorder is selected from the group consisting of alloimmune disease, autoimmune disease, cancer, hematological disease, infectious disease, inflammatory disease, ischemia-reperfusion injury, neurodegenerative disease, neurodegenerative disorder, ocular disease, renal disease, transplant rejection, vascular disease, and vasculitis disease. In some embodiments, the complement-mediated disease or disorder is an autoimmune disease. In some embodiments, the complement-mediated disease or disorder is an alloimmune disease. In some embodiments, the complement-mediated disease or disorder is cancer. In some embodiments, the complement-mediated disease or disorder is an infectious disease. In some embodiments, the complement-mediated disease or disorder is an inflammatory disease. In some embodiments, the complement-mediated disease or disorder is a hematological disease. In some embodiments, the complement-mediated disease or disorder is an ischemia-reperfusion injury. In some embodiments, the complement-mediated disease or disorder is ocular disease. In some embodiments, the complement-mediated disease or disorder is a renal disease. In some embodiments, the complement-mediated disease or disorder is transplant rejection. In some embodiments, the complement-mediated disease or disorder is antibody-mediated transplant rejection. In some embodiments, the complement-mediated disease or disorder is a vascular disease. In some embodiments, the complement-mediated disease or disorder is a vasculitis disorder. In some embodiments, the complement-mediated disease or disorder is a neurodegenerative disease or disorder. In some embodiments, the complement-mediated disease is a neurodegenerative disease. In some embodiments, the complement-mediated disorder is a neurodegenerative disorder.

Examples of a complement-mediated disease or disorder include, but are not limited to, age-related macular degeneration, Alzheimer's disease, amyotrophic lateral sclerosis, anaphylaxis, argyrophilic grain dementia, arthritis (e.g., rheumatoid arthritis), asthma, atherosclerosis, atypical hemolytic uremic syndrome, autoimmune diseases (including, e.g., autoimmune hemolytic anemia (AIHA); warm AIHA; mixed AIHA; etc.), Barraquer-Simons syndrome, Behçet's disease, British type amyloid angiopathy, bullous pemphigoid, Buerger's disease, C1q nephropathy, cancer, catastrophic antiphospholipid syndrome, cerebral amyloid angiopathy, cold agglutinin disease, corticobasal degeneration, Creutzfeldt-Jakob disease, Crohn's disease, cryoglobulinemic vasculitis, dementia pugilistic a, dementia with Lewy Bodies (DLB), diffuse neurofibrillary tangles with calcification, Discoid lupus erythematosus, Down's syndrome, Evan's syndrome, focal segmental glomerulosclerosis, formal thought disorder, frontotemporal dementia (FTD), frontotemporal dementia with parkinsonism linked to chromosome 17, frontotemporal lobar degeneration, Gerstmann-Straussler-Scheinker disease, Guillain-Barré syndrome, Hallervorden-Spatz disease, hemolytic-uremic syndrome, hereditary angioedema, hypophosphastasis, idiopathic pneumonia syndrome, immune complex diseases, inclusion body myositis, infectious disease (e.g., disease caused by bacterial (e.g., *Neisseria meningitidis* or *Streptococcus*) viral (e.g., human immunodeficiency virus (HIV)), or other infectious agents), inflammatory disease, ischemia/reperfusion injury, mild cognitive impairment, immuno-thrombocytopenic purpura (ITP), molybdenum cofactor deficiency (MoCD) type A, membranoproliferative glomerulonephritis (MPGN) I, membranoproliferative glomerulonephritis (MPGN) II (dense deposit disease), membranous nephritis, multi-infarct dementia, lupus (e.g., systemic lupus erythematosus (SLE)), glomerulonephritis, Kawasaki disease, multifocal motor neuropathy, multiple sclerosis, multiple system atrophy, myasthenia gravis, myocardial infarction, myotonic dystrophy, neuromyelitis optica, Niemann-Pick disease type C, non-Guamanian motor neuron disease with neurofibrillary tangles, Parkinson's disease, Parkinson's disease with dementia, paroxysmal nocturnal hemoglobinuria, Pemphigus vulgaris, Pick's disease, postencephalitic parkinsonism, polymyositis, prion protein cerebral amyloid angiopathy, progressive subcortical gliosis, progressive supranuclear palsy, psoriasis, sepsis, Shiga-toxin *E. coli* (STEC)-HuS, spinal muscular atrophy, stroke, subacute sclerosing panencephalitis, Tangle only dementia, transplant rejection, vasculitis (e.g., ANCA associated vasculitis), Wegner's granulomatosis, sickle cell disease, cryoglobulinemia, mixed cryoglobulinemia, essential mixed cryoglobulinemia, Type II mixed cryoglobulinemia, Type III mixed cryoglobulinemia, nephritis, drug-induced thrombocytopenia, lupus nephritis, *Epidermolysis bullosa acquisita*, delayed hemolytic transfusion reaction, hypocomplementemic urticarial vasculitis syndrome, pseudophakic bullous keratopathy, and platelet refractoriness.

In some embodiments, the complement-mediated disease or disorder comprises Alzheimer's disease. In some embodiments, the complement-mediated disease or disorder comprises Parkinson's disease. In some embodiments, the complement-mediated disease or disorder comprises transplant rejection. In some embodiments, the complement-mediated disease or disorder is antibody-mediated transplant rejection.

In some embodiments, a humanized anti-C1s antibody of the present disclosure prevents or delays the onset of at least one symptom of a complement-mediated disease or disorder in an individual. In some embodiment, an anti-C1s antibody of the present disclosure reduces or eliminates at least one symptom of a complement-mediated disease or disorder in an individual. Examples of symptoms include, but are not limited to, symptoms associated with autoimmune disease, cancer, hematological disease, infectious disease, inflammatory disease, ischemia-reperfusion injury, neurodegenerative disease, neurodegenerative disorder, renal disease, transplant rejection, ocular disease, vascular disease, or a vasculitis disorder. The symptom can be a neurological symptom, for example, impaired cognitive function, memory impairment, loss of motor function, etc. The symptom can also be the activity of C1s protein in a cell, tissue, or fluid of an individual. The symptom can also be the extent of complement activation in a cell, tissue, or fluid of an individual.

In some embodiments, administering a humanized anti-C1s antibody of the present disclosure to an individual modulates complement activation in a cell, tissue, or fluid of an individual. In some embodiments, administration of a subject anti-C1s antibody to an individual inhibits complement activation in a cell, tissue, or fluid of an individual. For example, in some embodiments, a subject humanized anti-C1s antibody, when administered in one or more doses as monotherapy or in combination therapy to an individual having a complement-mediated disease or disorder, inhibits complement activation in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to complement activation in the individual before treatment with the anti-C1s antibody.

In some embodiments, a humanized anti-C1s antibody of the present disclosure reduces C3 deposition onto red blood cells; for example, in some embodiments, an anti-C1s antibody of the present disclosure reduces deposition of C3b, iC3b, etc., onto RBCs). In some embodiments, an anti-C1s antibody of the present disclosure inhibits complement-mediated red blood cell lysis.

In some embodiments, a humanized anti-C1s antibody of the present disclosure reduces C3 deposition onto platelets; for example, in some embodiments, an anti-C1s antibody of the present disclosure reduces deposition of C3b, iC3b, etc., onto platelets).

In some embodiments, administering a humanized anti-C1s antibody of the present disclosure results in an outcome selected from the group consisting of: (a) a reduction in complement activation; (b) an improvement in cognitive function; (c) a reduction in neuron loss; (d) a reduction in glial cell activation; (e) a reduction in lymphocyte infiltration; (f) a reduction in macrophage infiltration; (g) a reduction in antibody deposition, (h) a reduction in glial cell loss; (i) a reduction in oligodendrocyte loss; (j) a reduction in dendritic cell infiltration; (k) a reduction in neutrophil infiltration; (l) a reduction in red blood cell lysis; (m) a reduction in red blood cell phagocytosis; (n) a reduction in platelet phagocytosis; (o) a reduction in platelet lysis; (p) an improvement in transplant graft survival; (q) a reduction in macrophage mediated phagocytosis; (r) an improvement in vision; (s) an improvement in motor control; (t) an improvement in thrombus formation; (u) an improvement in clotting; (v) an improvement in kidney function; (w) a reduction in antibody mediated complement activation; (x) a reduction in autoantibody mediated complement activation; (y) an improvement in anemia; (aa) reduction of demyelination; (ab) reduction of eosinophilia; (ac) a reduction of C3 deposition on red blood cells (e.g., a reduction of deposition of C3b, iC3b, etc., onto RBCs); and (ad) a reduction in C3 deposition on platelets (e.g., a reduction of deposition of C3b, iC3b, etc., onto platelets); and (ae) a reduction of anaphylatoxin toxin production; (af) a reduction in autoantibody mediated blister formation; (ag) a reduction in autoantibody induced pruritis; (ah) a reduction in autoantibody induced erythematosus; (ai) a reduction in autoantibody mediated skin erosion; (aj) a reduction in red blood cell destruction due to transfusion reactions; (ak) a reduction in red blood cell lysis due to alloantibodies; (al) a reduction in hemolysis due to transfusion reactions; (am) a reduction in allo-antibody mediated platelet lysis; (an) a reduction in platelet lysis due to transfusion reactions; (ao) a reduction in mast cell activation; (ap) a reduction in mast cell histamine release; (aq) a reduction in vascular permeability; (ar) a reduction in edema; (as) a reduction in complement deposition on transplant graft endothelium; (at) a reduction of anaphylatoxin generation in transplant graft endothelium; (au) a reduction in the separation of the dermal-epidermal junction; (av) a reduction in the generation of anaphylatoxins in the dermal-epidermal junction; (aw) a reduction in alloantibody mediated complement activation in transplant graft endothelium; (ax) a reduction in antibody mediated loss of the neuromuscular junction; (ay) a reduction in complement activation at the neuromuscular junction; (az) a reduction in anaphylatoxin generation at the neuromuscular junction; (ba) a reduction in complement deposition at the neuromuscular junction; (bb) a reduction in paralysis; (bc) a reduction in numbness; (bd) increased bladder control; (be) increased bowel control; (bf) a reduction in mortality associated with autoantibodies; and (bg) a reduction in morbidity associated with autoantibodies.

In some embodiments, a subject anti-C1s antibody, when administered in one or more doses as monotherapy or in combination therapy to an individual having a complement-mediated disease or disorder, is effect to achieve a reduction of at least about 10%, at least about 15%, at least about 20%, at least about 25%, at least about 30%, at least about 40%, at least about 50%, at least about 60%, at least about 70%, at least about 80%, at least about 90%, or more than 90%, of one or more of the following outcomes: (a) complement activation; (b) decline in cognitive function; (c) neuron loss; (d) glial cell activation; (e) lymphocyte infiltration; (f) macrophage infiltration; (g) antibody deposition, (h) glial cell loss; (i) oligodendrocyte loss; (j) dendritic cell infiltration; (k) neutrophil infiltration; (l) red blood cell lysis; (m) red blood cell phagocytosis; (n) platelet phagocytosis; (o) platelet lysis; (p) transplant graft rejection; (q) macrophage mediated phagocytosis; (r) vision loss; (s) antibody mediated complement activation; (t) autoantibody mediated complement activation; (u) demyelination; (v) eosinophilia;

compared to the level or degree of the outcome in the individual before treatment with the anti-C1s antibody.

In some embodiments, a subject anti-C1s antibody, when administered in one or more doses as monotherapy or in combination therapy to an individual having a complement-mediated disease or disorder, is effect to achieve an improvement of at least about 10%, at least about 15%, at least about 20%, at least about 25%, at least about 30%, at least about 40%, at least about 50%, at least about 60%, at least about 70%, at least about 80%, at least about 90%, or more than 90%, of one or more of the following outcomes: a) cognitive function; b) transplant graft survival; c) vision; d) motor control; e) thrombus formation; f) clotting; g) kidney function; and h) hematocrit (red blood cell count), compared to the level or degree of the outcome in the individual before treatment with the anti-C1s antibody.

In some embodiments, administering a humanized anti-C1s antibody of the present disclosure to an individual reduces complement activation in the individual. For example, in some embodiments, a subject anti-C1s antibody, when administered in one or more doses as monotherapy or in combination therapy to an individual having a complement-mediated disease or disorder, reduces complement activation in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to complement activation in the individual before treatment with the anti-C1s antibody.

In some embodiments, administering a humanized anti-C1s antibody of the present disclosure improves cognitive function in the individual. For example, in some embodiments, a subject anti-C1s antibody, when administered in one or more doses as monotherapy or in combination therapy to an individual having a complement-mediated disease or disorder, improves cognitive function in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to the cognitive function in the individual before treatment with the anti-C1s antibody.

In some embodiments, administering a humanized anti-C1s antibody of the present disclosure reduces the rate of decline in cognitive function in the individual. For example, in some embodiments, a subject anti-C1s antibody, when administered in one or more doses as monotherapy or in combination therapy to an individual having a complement-mediated disease or disorder, reduces the rate of decline of cognitive function in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to the rate of decline in cognitive function in the individual before treatment with the anti-C1s antibody.

In some embodiments, administering a humanized anti-C1s antibody of the present disclosure to an individual reduces neuron loss in the individual. For example, in some embodiments, a subject anti-C1s antibody, when administered in one or more doses as monotherapy or in combination therapy to an individual having a complement-mediated disease or disorder, reduces neuron loss in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to neuron loss in the individual before treatment with the anti-C1s antibody.

In some embodiments, administering a humanized anti-C1s antibody of the present disclosure to an individual reduces glial cell activation in the individual. For example, in some embodiments, a subject anti-C1s antibody, when administered in one or more doses as monotherapy or in combination therapy to an individual having a complement-mediated disease or disorder, reduces glial activation in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to glial cell activation in the individual before treatment with the anti-C1s antibody. In some embodiments, the glial cells are astrocytes or microglia.

In some embodiments, administering a humanized anti-C1s antibody of the present disclosure to an individual reduces lymphocyte infiltration in the individual. For example, in some embodiments, a subject anti-C1s antibody, when administered in one or more doses as monotherapy or in combination therapy to an individual having a complement-mediated disease or disorder, reduces lymphocyte infiltration in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to lymphocyte infiltration in the individual before treatment with the anti-C1s antibody.

In some embodiments, administering a humanized anti-C1s antibody of the present disclosure to an individual reduces macrophage infiltration in the individual. For example, in some embodiments, a humanized anti-C1s antibody of the present disclosure, when administered in one or more doses as monotherapy or in combination therapy to an individual having a complement-mediated disease or disorder, reduces macrophage infiltration in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to macrophage infiltration in the individual before treatment with the anti-C1s antibody.

In some embodiments, administering a humanized anti-C1s antibody of the present disclosure to an individual reduces antibody deposition in the individual. For example, in some embodiments, a humanized anti-C1s antibody of the present disclosure, when administered in one or more doses as monotherapy or in combination therapy to an individual having a complement-mediated disease or disorder, reduces antibody deposition in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to antibody deposition in the individual before treatment with the anti-C1s antibody.

In some embodiments, administering an anti-C1s antibody of the present disclosure to an individual reduces anaphylatoxin (e.g., C3a, C4a, C5a) production in an individual. For example, in some embodiments, a humanized anti-C1s antibody of the present disclosure, when administered in one or more doses as monotherapy or in combination therapy to an individual having a complement-mediated disease or disorder, reduces anaphylatoxin production in the individual by at least about 10%, at least about 15%, at least about 20%, at least about 25%, at least about 30%, at least about 40%, at least about 50%, at least about 60%, at least about 70%, at least about 80%, at least about 90%, or more than 90%, compared to the level of anaphylatoxin production in the individual before treatment with the anti-C1s antibody.

The present disclosure provides for use of a humanized anti-C1s antibody of the present disclosure or a pharmaceutical composition comprising a humanized anti-C1s antibody of the present disclosure and a pharmaceutically acceptable excipient to treat an individual having a complement-mediated disease or disorder. In some embodiments, the present disclosure provides for use of a humanized anti-C1s antibody of the present disclosure to treat an individual having a complement-mediated disease or disorder. In some embodiments, the present disclosure provides for use of a pharmaceutical composition comprising a humanized anti-C1s antibody of the present disclosure and a pharmaceutically acceptable excipient to treat an individual having a complement-mediated disease or disorder.

The present disclosure provides for use of a humanized anti-C1s antibody of the present disclosure in the manufacture of a medicament for the treatment of an individual having a complement-mediated disease or disorder.

The present disclosure provides for use of a humanized anti-C1s antibody of the present disclosure or a pharmaceutical composition comprising a humanized anti-C1s antibody of the present disclosure and a pharmaceutically acceptable excipient to inhibit complement activation. In some embodiments, the present disclosure provides for use of a humanized anti-C1s antibody of the present disclosure or a pharmaceutical composition comprising a humanized anti-C1s antibody of the present disclosure and a pharmaceutically acceptable excipient to inhibit complement activation in an individual having a complement-mediated disease or disorder. In some embodiments, the present disclosure provides for use of a humanized anti-C1s antibody of the present disclosure to inhibit complement activation in an individual having a complement-mediated disease or disorder. In some embodiments, the present disclosure provides for use of a pharmaceutical composition comprising a humanized anti-C1s antibody of the present disclosure and a pharmaceutically acceptable excipient to inhibit complement activation in an individual having a complement-mediated disease or disorder.

The present disclosure provides for use of a humanized anti-C1s antibody of the present disclosure in the manufacture of a medicament for modulating complement activation. In some embodiments, the medicament inhibits complement activation. In some embodiments, the medicament inhibits complement activation in an individual having a complement-mediated disease or disorder.

The present disclosure provides for a humanized anti-C1s antibody of the present disclosure or a pharmaceutical composition comprising a humanized anti-C1s antibody of the present disclosure and a pharmaceutically acceptable excipient for use in medical therapy. In some embodiments, the present disclosure provides for a humanized anti-C1s antibody of the present disclosure for use in medical therapy. In some embodiments, the present disclosure provides for a pharmaceutical composition comprising a humanized anti-C1s antibody of the present disclosure and a pharmaceutically acceptable excipient for use in medical therapy.

The present disclosure provides for a humanized anti-C1s antibody of the present disclosure or a pharmaceutical composition comprising a humanized anti-C1s antibody of the present disclosure and a pharmaceutically acceptable excipient for treating an individual having a complement-mediated disease or disorder. In some embodiments, the present disclosure provides for a humanized anti-C1s antibody of the present disclosure for treating an individual having a complement-mediated disease or disorder. In some embodiments, the present disclosure provides for a pharmaceutical composition comprising a humanized anti-C1s antibody of the present disclosure and a pharmaceutically acceptable excipient for treating an individual having a complement-mediated disease or disorder.

The present disclosure provides for a humanized anti-C1s antibody of the present disclosure or a pharmaceutical composition comprising a humanized anti-C1s antibody of the present disclosure and a pharmaceutically acceptable excipient for modulating complement activation. In some embodiments, the present disclosure provides for a humanized anti-C1s antibody of the present disclosure for modulating complement activation. In some embodiments, the present disclosure provides for a pharmaceutical composition comprising a humanized anti-C1s antibody of the present disclosure and a pharmaceutically acceptable excipient for modulating complement activation. In some embodiments, the anti-C1s antibody inhibits complement activation.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Humanized TNT005 Variants

Humanized variants of TNT005 were generated Amino acid sequences of the heavy chain VH domains of humanized variants 1-5; nucleotide sequences encoding the heavy chain VH domain of the humanized variants are also provided Amino acid sequences of the light chain VL domain of humanized variants 1, 2, and 5, and nucleotide sequences encoding the light chain VL domain of the humanized variants, are shown in FIGS. 6-8. Amino acid differences relative to the amino acid sequence of TNT005 (VL SEQ ID NO:7; VH SEQ ID NO:8) are summarized in Tables 2 and 3 (FIG. 9 and FIG. 10, respectively).

Single letter amino acid codes are as follows (with 3-letter amino acid codes in parentheses):
G—Glycine (Gly)
P—Proline (Pro)
A—Alanine (Ala)
V—Valine (Val)
L—Leucine (Leu)

I—Isoleucine (Ile)
M—Methionine (Met)
C—Cysteine (Cys)
F—Phenylalanine (Phe)
Y—Tyrosine (Tyr)
W—Tryptophan (Trp)
H—Histidine (His)
K—Lysine (Lys)
R—Arginine (Arg)
Q—Glutamine (Gln)
N—Asparagine (Asn)
E—Glutamic Acid (Glu)
D—Aspartic Acid (Asp)
S—Serine (Ser)
T—Threonine (Thr)

Example 2: Characterization of Humanized TNT005 Variants

Binding characteristics of humanized TNT005 variants are provided in Tables 4 and 5 (FIG. 11 and FIG. 12, respectively). The relative binding affinities for various humanized TNT005 variants to activated C1s are provided in Table 4 (first data column), which is presented in FIG. 11.

All 15 combinations (VH variant 1+Vk variant 1; VH variant 1+Vk variant 2; VH variant 1+Vk variant 5; VH variant 2+Vk variant 1; VH variant 2+Vk variant 2; VH variant 2+Vk variant 5; VH variant 3+Vk variant 1; VH variant 3+Vk variant 2; VH variant 3+Vk variant 5; VH variant 4+Vk variant 1; VH variant 4+Vk variant 2; VH variant 4+Vk variant 5; VH variant 5+Vk variant 1; VH variant 5+Vk variant 2; VH variant 5+Vk variant 5) were produced. Each humanized variant was tested for the ability to compete with biotinylated TNT005 for binding to active C1s. The data are shown in FIG. 11, second data column.

Each humanized variant was tested in a commercially available assay that measures complement classical pathway (CP) activation. The results are shown in FIG. 11, third data column. The data show that all 15 humanized variants inhibit CP activation with an $IC_{50}$ similar to that of TNT005.

Kinetic characterization of binding affinity was carried out on 8 of the humanized TNT005 variants. The data are depicted in Table 5, which is presented in FIG. 12.

Example 3: In Vivo Studies in Cynomolgus Monkeys

To assess the pharmacokinetic (PK) and pharmacodynamic (PD) properties of humanized TNT005, single- and repeat-dose studies of humanized TNT005 were performed in cynomolgus monkeys (*Macaca fascicularis*). Additionally, to compare the bioavailability of humanized TNT005 by various routes of administration, the humanized TNT005 variant was administered either by intravascular (IV) or subcutaneous (SC) injection. Following humanized TNT005 dosing, plasma and serum samples were taken at designated time points to determine circulating concentrations (PK) of humanized TNT005, and to assess inhibition of the classical complement pathway (PD) by humanized TNT005.

All study animals were female, between 2.4-3.9 kg body weight, and were between the ages of 3-5 years old. Additionally, all animals were naïve to pharmaceutical dosing.

The study consisted of two parts:
1) Phase 1—a single dose study comparing the PK/PD of humanized TNT005 in vehicle control (no drug administered), low dose, and high dose groups by intravenous (IV) administration, and a matching high dose humanized TNT005 group administered subcutaneously (SC); and
2) Phase 2—a multi-dose (daily for 7 days) low dose SC group.

The Phase 1 study design consisted of four groups of animals, of which three were dosed with humanized TNT005 (n=4 animals/dose cohort), and the fourth with vehicle control (phosphate buffered saline; n=3 animals) Animals dosed IV were provided a bolus injection in a peripheral vein, whereas SC injection was administered in the interscapular region of the back. Group 1 was designated the control group, and was administered vehicle IV. Group 2 and Group 3 were administered a single IV dose of humanized TNT005 at 10 mg/kg and 45 mg/kg, respectively. Finally, Group 4 was administered a single SC dose at 45 mg/kg to directly compare SC bioavailability with the corresponding IV group (Group 3). Table 6 summarizes the Phase 1 study design.

TABLE 6

| Group | Test Article | Route | Dose Level (mg/kg) | Dose Concentration (mg/mL) | Dose Volume (mL/kg) | Number of Female Animals |
|---|---|---|---|---|---|---|
| 1 | Vehicle | IV | 0 | 0 | 4.5 | 3 |
| 2 | humanized TNT005 | IV | 10 | 2.2 | 4.5 | 4 |
| 3 | humanized TNT005 | IV | 45 | 10 | 4.5 | 4 |
| 4 | humanized TNT005 | SC | 45 | 10 | 4.5 | 4 |

Whole blood was collected in $K_2$EDTA tubes and serum separator tubes for plasma and serum processing, respectively, and immediately stored at −15° C. to −25° C. Sample collections occurred before and after dosing with humanized TNT005 or vehicle control according to the schedule described in Table 7.

TABLE 7

| Group | Blood Collections (hr post dose) | Blood Volume | Collection Tube/Additive/ Processing | Aliquots/ Storage |
|---|---|---|---|---|
| All | Predose, 0.25, 0.5, 1, 4, 8, 12, 24, 48, 72, 96, 120, 168, 240, 336, 432, and 504 (Day 22) hours postdose. Additionally, samples were collected daily on Days 23 through 43 post dose | At least 1.3 mL | SST (~0.7 mL)/ Centrifuge per SOP $K_2$EDTA (~0.6 mL) on ice/ Centrifuge at 2 to 8° C. | 1 × 350 µL −15 to −25° C. 1 × 300 µL −15 to −25° C. |

The Phase 2 study was designed to assess the PK/PD relationship of repeated low dose humanized TNT005 administered SC. Phase 2 animals were appropriated from the Phase 1 control group (n=3) in addition to one animal from the low dose IV group (Group 1). Animals in Phase 2 were dosed daily with 4 mg/kg humanized TNT005 SC for 7 days. Phase 2 animals were dosed 57 days after Phase 1 dosing. Table 8 summarizes the Phase 2 study design.

TABLE 8

| Group | Test Article | Route | Dose Level (mg/kg) | Dose Concentration (mg/mL) | Dose Volume (mL/kg) | Number of Female Animals |
|---|---|---|---|---|---|---|
| 1 | humanized TNT005 | SC | 4 | 0.9 | 4.5 | 4 |

Whole blood was collected in $K_2$EDTA tubes and serum separator tubes for plasma and serum processing, respectively, and immediately stored at −15° C. to −25° C. Sample collections occurred before and after dosing with humanized TNT005 according to the schedule described in Table 9.

TABLE 9

Phase 2 Whole Blood Collection Schedule

| Group | Blood Collections (hr post dose) | Blood Volume | Collection Tube/Additive/ Processing | Aliquots/ Storage |
|---|---|---|---|---|
| 1 | Day 1: Predose, and at 1.5, 2, 3, 4, 6, 10, 12, and 24 hours postdose (predose on Day 2) Days 3 through 6: Predose Day 7: Predose, and at 1.5, 4, 8, 12, 24, and 48 hours postdose | At least 1.3 mL | SST (~0.7 mL)/ Centrifuge per SOP K2EDTA (~0.6 mL) on ice/ Centrifuge at 2 to 8° C. | 1 × 350 μL −15 to −25° C. 1 × 300 μL −15 to −25° C. |

Results

Phase 1 Pharmacokinetics and Pharmacodynamics

To assess the pharmacokinetic profile of humanized TNT005 in Phase 1, plasma samples taken at the time points designated in Table 7 were diluted and run in an ELISA to quantify humanized TNT005 plasma concentrations. Briefly, diluted plasma samples were added to a 96-well plate pre-coated with activated C1s. Following plasma sample incubation and subsequent washing, a horseradish peroxidase-conjugated detection antibody specific for human IgG was added to detect C1s-bound humanized TNT005. Finally, 3,3′,5,5′-tetramethylbenzidine (TMB) substrate was added to initiate a colorimetric reaction that was read on a spectrophotometer. By interpolating from a standard curve of humanized TNT005 run in parallel with the plasma samples, humanized TNT005 plasma concentrations were determined for all samples. Results of the pharmacokinetic analysis of Phase 1 of the study are shown in FIG. 14 (Day 1-43) and FIG. 15 (Day 32-43). After IV administration, plasma PK profiles of humanized TNT005 exhibited a typically high Cmax followed by clearance that was dose-dependent. SC administration resulted in a slower absorption phase, resulting in an overall lower Cmax that was delayed compared to the matched IV dose cohort. The rate of humanized TNT005 clearance in the 45 mg/kg IV and SC dose groups was comparable from 72 hours to the end of the study.

FIG. 14 depicts a pharmacokinetic profile of humanized TNT005 in cynomolgus monkeys dosed in Phase 1 (Day 1-Day 43). Dose groups received vehicle; 10 mg/kg (MPK) humanized TNT005 IV; 45 MPK humanized TNT005 IV; or 45 MPK humanized TNT005 SC. Average humanized TNT005 plasma concentrations for each dose group (n=4 animals/humanized TNT005 cohort) are plotted vs. time post dose.

Figure 15:
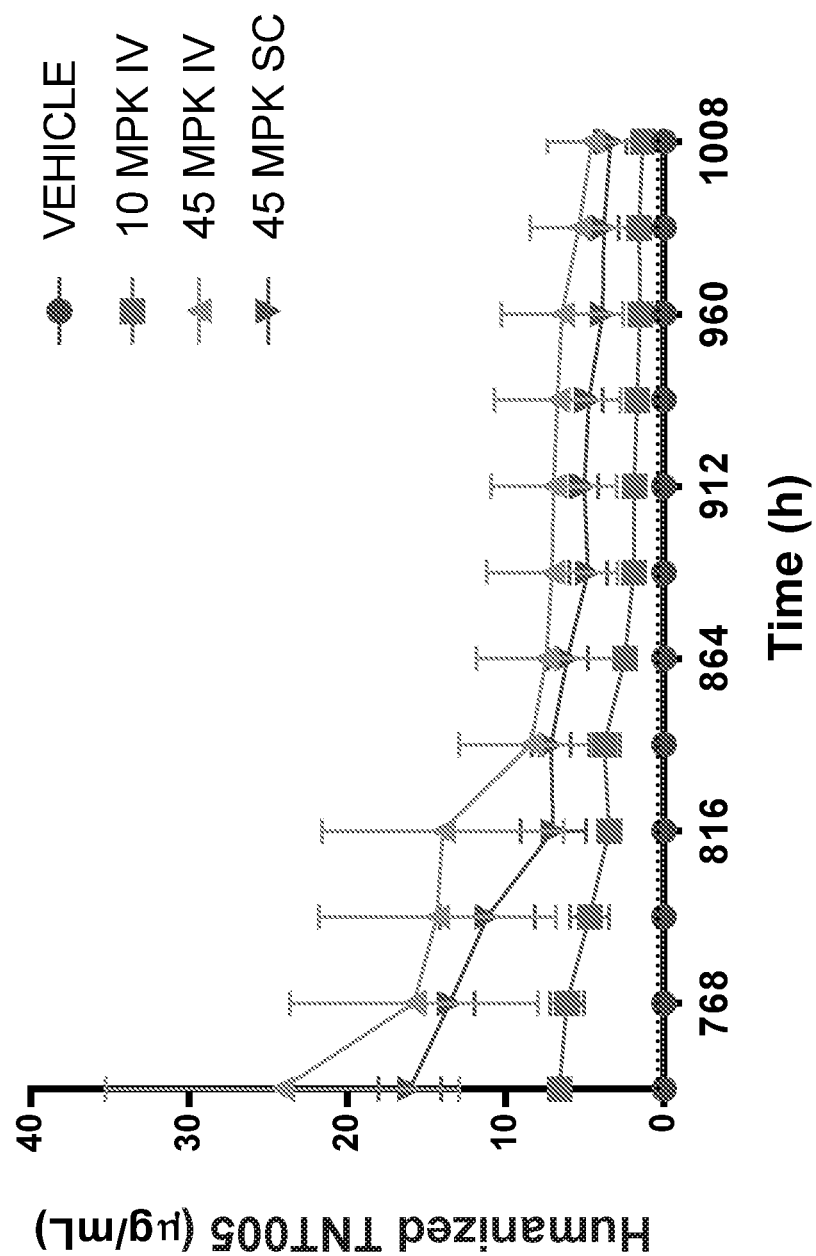
FIG. 15 depicts a pharmacokinetic profile of a humanized TNT005 variant in cynomolgus monkeys dosed in Phase 1 (Day 32-Day 43).

FIG. 15 depicts pharmacokinetic profiles of humanized TNT005 in cynomolgus monkeys dosed in Phase 1 (Day 32-Day 43). Dose groups were as for FIG. 14. Average humanized TNT005 plasma concentrations for each dose group (n=4 animals/humanized TNT005 cohort) are plotted vs. time post dose.

Figure 16:
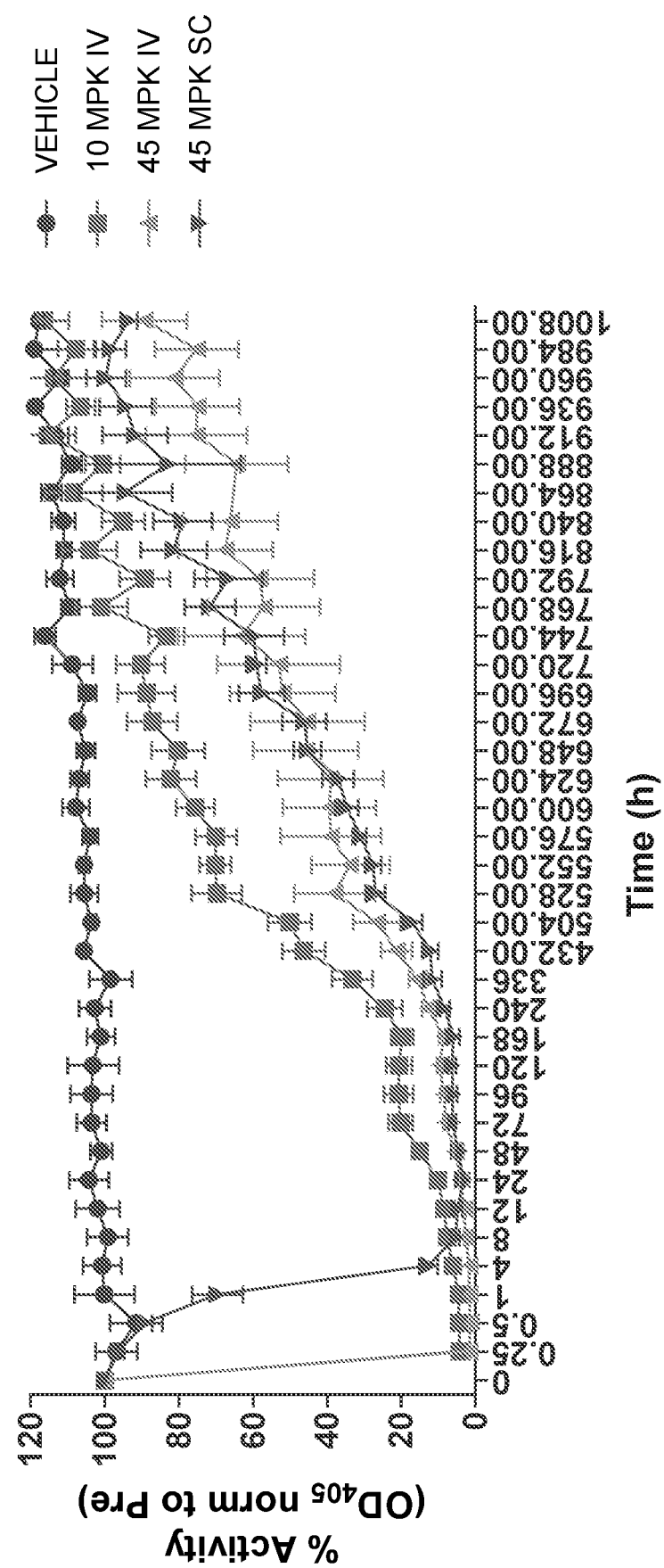
FIG. 16 depicts classical pathway activity of serum from cynomolgus monkeys dosed in Phase 1 (Day 1-Day 43).

The pharmacodynamic effects of humanized TNT005 were assessed using the Wieslab® classical complement pathway kit. The Wieslab® kit is commercially available, and involves use of an enzyme-linked immunosorbent assay (ELISA) that is designed to evaluate the strength of classical complement pathway activity in serum samples by activating the classical pathway of the sample ex vivo and measuring the ex vivo generation of the final split product of the pathway, C5b-9. Samples were assayed according to the manufacturer's instructions. Briefly, serum samples from the monkeys, collected at the time points shown in Table 7, were diluted and added to the wells of the provided 96-well plate. Following incubation, a detection antibody specific for the final split product of the classical pathway, C5b-9, was added and the colorimetric reaction measured on a spectrophotometer. All samples for an individual monkey were compared and normalized to the pre-dose sample of the same monkey (pre-dose=100% activity). Results for the pharmacodynamic readout in Phase 1 groups are shown in FIG. 16. IV administration of humanized TNT005 resulted in near-complete to complete inhibition of the classical pathway in both dose groups immediately after dosing. Recovery of classical pathway activity was gradual and dose dependent, with animals in the 45 mg/kg dose cohorts recovering more slowly than the 10 mg/kg cohort. IV and SC groups dosed at 45 mg/kg showed very similar recovery times for pathway activity, consistent with the similar humanized TNT005 pharmacokinetic profiles for those groups (FIG. 14).

FIG. 16 depicts the classical pathway activity (PD readout) of serum samples from cynomolgous monkeys dosed in Phase 1 (Day 1-Day 43). Dose groups received vehicle; 10 mg/kg (MPK) humanized TNT005 IV; 45 MPK humanized TNT005 IV; or 45 MPK humanized TNT005 SC. Classical pathway activity for each dose group (normalized to pre-dose activity; n=4 animals/humanized TNT005 group) are plotted vs. time post dose.

Phase 2 Pharmacokinetics (PK) and Pharmacodynamics (PD)

Figure 17:
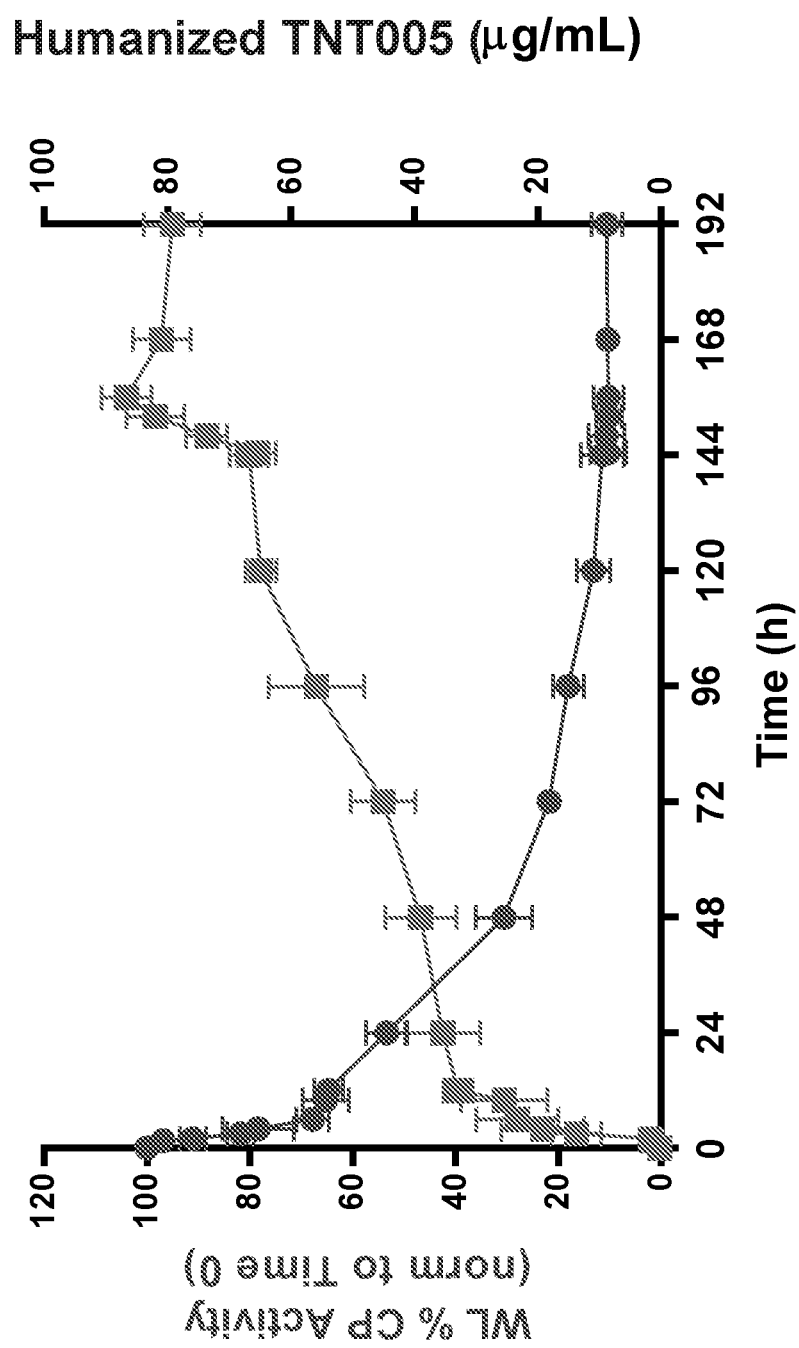
FIG. 17 depicts a PK and pharmacodynamic (PD) profile of a humanized TNT005 variant in cynomolgus monkeys dosed in Phase 2 (4 mg/kg daily subcutaneous administration for 7 days).

Humanized TNT005 pharmacokinetics and pharmacodynamics in Phase 2 were assayed in the same manner as described in Phase 1. Results of the pharmacokinetic and pharmacodynamics analyses of Phase 2 of the study are shown in FIG. 17. SC administration of low dose humanized TNT005 (4 mg/kg) resulted in a slow absorption phase within the first 24 hours of dosing (FIG. 17, red plot, right y-axis). Concomitant with the rise in plasma humanized TNT005 concentrations, serum classical pathway activity decreased (FIG. 17, blue plot, left y-axis). Repeated daily dosing at 4 mg/kg resulted in a gradual increase in plasma humanized TNT005 and further reduced serum classical pathway activity to 10% of pre-dose levels by Day 7 (i.e.—90% classical pathway inhibition).

FIG. 17 depicts a PK/PD profile of humanized TNT005 in cynomolgous monkeys dosed in Phase 2 (4 mg/kg daily SC administration for 7 days). Average humanized TNT005 plasma concentrations (right y-axis) and average serum classical pathway activity (left y-axis) were plotted vs. time for Phase 2 (n=4 animals)

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A humanized antibody that specifically binds complement component C1s, wherein the antibody comprises:

a) a VH region comprising the amino acid sequence:

(SEQ ID NO: 26)
(Q/E)VQL(V/Q)QSGAE(V/L)KKPGASVK(L/V)SC(T/A)ASGFNIKD

DYIHWV(K/R)QAPGQGLEWIGRIDPADGHTKYAPKFQVK(V/A)TITADT

ST(S/N)TAY(L/M)(E/Q)LSSL(R/T)SEDTAVYYCARYGYGREVFDYW

GQGTTVTSS;

SEQ ID NO:26); and b) a VL region comprising the amino acid sequence:

(SEQ ID NO: 27)
DIVLTQSPDSLAVSLGERATISCKASQSVDYDGDSYMNWYQQK(T/P)GQP

PK(I/L)LIYDASNLESGIPARFSGSGSGTDFTLTISSLE(E/P)EDFA(

I/V)YYCQQSNEDPWTFGGGTKVEIK.

SEQ ID NO:27).

2. The humanized antibody of claim 1, wherein the antibody is selected from the group consisting of:
a) an antibody comprising a VH region comprising the amino acid sequence set forth in SEQ ID NO:14 and a VL region comprising the amino acid sequence set forth in SEQ ID NO:22;
b) an antibody comprising a VH region comprising the amino acid sequence set forth in SEQ ID NO:10 and a VL region comprising the amino acid sequence set forth in SEQ ID NO:20;
c) an antibody comprising a VH region comprising the amino acid sequence set forth in SEQ ID NO:10 and a VL region comprising the amino acid sequence set forth in SEQ ID NO:22;
d) an antibody comprising a VH region comprising the amino acid sequence set forth in SEQ ID NO:10 and a VL region comprising the amino acid sequence set forth in SEQ ID NO:24;
e) an antibody comprising a VH region comprising the amino acid sequence set forth in SEQ ID NO:12 and a VL region comprising the amino acid sequence set forth in SEQ ID NO:20;
f) an antibody comprising a VH region comprising the amino acid sequence set forth in SEQ ID NO:12 and a VL region comprising the amino acid sequence set forth in SEQ ID NO:22;
g) an antibody comprising a VH region comprising the amino acid sequence set forth in SEQ ID NO:12 and a VL region comprising the amino acid sequence set forth in SEQ ID NO:24;
h) an antibody comprising a VH region comprising the amino acid sequence set forth in SEQ ID NO:14 and a VL region comprising the amino acid sequence set forth in SEQ ID NO:20;
i) an antibody comprising a VH region comprising the amino acid sequence set forth in SEQ ID NO:14 and a VL region comprising the amino acid sequence set forth in SEQ ID NO:24;
j) an antibody comprising a VH region comprising the amino acid sequence set forth in SEQ ID NO:16 and a VL region comprising the amino acid sequence set forth in SEQ ID NO:20;
k) an antibody comprising a VH region comprising the amino acid sequence set forth in SEQ ID NO:16 and a VL region comprising the amino acid sequence set forth in SEQ ID NO:22;
l) an antibody comprising a VH region comprising the amino acid sequence set forth in SEQ ID NO:16 and a VL region comprising the amino acid sequence set forth in SEQ ID NO:24;
m) an antibody comprising a VH region comprising the amino acid sequence set forth in SEQ ID NO:18 and a VL region comprising the amino acid sequence set forth in SEQ ID NO:20;
n) an antibody comprising a VH region comprising the amino acid sequence set forth in SEQ ID NO:18 and a VL region comprising the amino acid sequence set forth in SEQ ID NO:22; and
o) an antibody comprising a VH region comprising the amino acid sequence set forth in SEQ ID NO:18 and a VL region comprising the amino acid sequence set forth in SEQ ID NO:24.

3. The humanized antibody of claim 1, wherein the humanized antibody is a Fab fragment, a F(ab')$_2$ fragment, a scFv, or a Fv.

4. The humanized antibody of claim 1, wherein the humanized antibody comprises a heavy chain constant region of the isotype IgG1, IgG2, IgG3, or IgG4.

5. A composition comprising:
a) the humanized antibody of claim 1; and
b) a pharmaceutically acceptable excipient.

6. The composition of claim 5, wherein the composition comprises one or more of a tonicity agent, a suspending agent, an emulsifying agent, a stabilizer, a preservative, a lyoprotectant, a surfactant, and a sugar.

7. A method of reducing the level of a complement component cleavage product in a human, the method comprising administering to the human the composition of claim 5 in an amount effective to inhibit C1s and to reduce the level of the cleavage product.

8. The method of claim 7, wherein the administering is selected from the group consisting of intravenously administering, intramuscularly administering, intrathecally administering, and subcutaneously administering.

9. A method of inhibiting C1s-mediated cleavage of a complement component in a human, the method comprising administering to the human the composition of claim 5 in an amount effective to inhibit C1s-mediated cleavage of a complement component.

10. A method comprising administering to a human a composition comprising a humanized antibody that specifically binds complement component C1s, wherein the antibody comprises:

a) a VH region comprising the amino acid sequence:

(SEQ ID NO: 26)
(Q/E)VQL(V/Q)QSGAE(V/L)KKPGASVK(L/V)SC(T/A)ASGFNIK

DDYIHWV(K/R)QAPGQGLEWIGRIDPADGHTKYAPKFQVK(V/A)TITA

DTST(S/N)TAY(L/M)(E/Q)LSSL(R/T)SEDTAVYYCARYGYGREVF

DYWGQGTTVTSS;

(SEQ ID NO:26); and
b) a VL region comprising the amino acid sequence:

```
                                            (SEQ ID NO: 27)
DIVLTQSPDSLAVSLGERATISCKASQSVDYDGDSYMNWYQQK(T/P)GQ

PPK(I/L)LIYDASNLESGIPARFSGSGSGTDFTLTISSLE(E/P)EDFA (I/V)YYCQQSNEDPWTFGGGTKVEIK.
```

(SEQ ID NO:27).

11. The method of claim 9, wherein the human has Alzheimer's disease, amyotrophic lateral sclerosis, anaphylaxis, argyrophilic grain dementia, arthritis asthma, atherosclerosis, atypical hemolytic uremic syndrome, autoimmune diseases Barraquer-Simons syndrome, Behcet's disease, British type amyloid angiopathy, bullous pemphigoid, Buerger's disease, Clq nephropathy, cancer, catastrophic antiphospholipid syndrome, cerebral amyloid angiopathy, cold agglutinin disease, corticobasal degeneration, Creutzfeldt-Jakob disease, Crohn's disease, cryoglobulinemic vasculitis, dementia pugilistica, dementia with Lewy Bodies (DLB), diffuse neurofibrillary tangles with calcification, Discoid lupus erythematosus, Down's syndrome, Evan's syndrome, focal segmental glomerulosclerosis, formal thought disorder, frontotemporal dementia (FTD), frontotemporal dementia with parkinsonism linked to chromosome 17, frontotemporal lobar degeneration, Gerstmann-Straussler-Scheinker disease, Guillain-Barr syndrome, Hallervorden-Spatz disease, hemolytic-uremic syndrome, hereditary angioedema, hypophosphastasis, idiopathic pneumonia syndrome, immune complex diseases, inclusion body myositis, infectious disease, inflammatory disease, ischemia/reperfusion injury, mild cognitive impairment, immunothrombocytopenic purpura (ITP), molybdenum cofactor deficiency (MoCD) type A, membranoproliferative glomerulonephritis (MPGN) I, membranoproliferative glomerulonephritis (MPGN) II (dense deposit disease), membranous nephritis, multi-infarct dementia, lupus, glomerulonephritis, Kawasaki disease, multifocal motor neuropathy, multiple sclerosis, multiple system atrophy, myasthenia gravis, myocardial infarction, myotonic dystrophy, neuromyelitis optica, Niemann-Pick disease type C, non-Guamanian motor neuron disease with neurofibrillary tangles, Parkinson's disease, Parkinson's disease with dementia, paroxysmal nocturnal hemoglobinuria, Pemphigus vulgaris, Pick's disease, postencephalitic parkinsonism, polymyositis, prion protein cerebral amyloid angiopathy, progressive, subcortical gliosis, progressive supranuclear palsy, psoriasis, sepsis, Shiga-toxin *E. coli* (STEC)-HuS, spinal muscular atrophy, stroke, subacute sclerosing panencephalitis, Tangle only dementia, transplant rejection, vasculitis, Wegner's granulomatosis, sickle cell disease, cryoglobulinemia, mixed cryoglobulinemia, essential mixed cryoglobulinemia, Type II mixed cryoglobulinemia, Type III mixed cryoglobulinemia, nephritis, drug-induced thrombocytopenia, lupus nephritis, *Epidermolysis bullosa acquisita*, delayed hemolytic transfusion reaction, hypocomplementemic urticarial vasculitis syndrome, pseudophakic bullous keratopathy or platelet refractoriness.

12. The method of claim 10, wherein the administering is selected from the group consisting of intravenously administering, intramuscularly administering, intrathecally administering, and subcutaneously administering.

13. A humanized antibody that specifically binds complement component C1s, wherein the antibody comprises a VH region comprising the amino acid sequence set forth in SEQ ID NO:14, a VL region comprising the amino acid sequence set forth in SEQ ID NO:22, and a heavy chain constant region of the isotype IgG4.

14. The method of claim 10, wherein the human has cold agglutinin disease.

15. The method of claim 10, wherein the human has immunothrombocytopenic purpura (ITP).

16. The method of claim 10, wherein the human has bullous pemphigoid.

17. The method of claim 10, wherein the human has multifocal motor neuropathy.

18. The method of claim 10, wherein the human has an autoimmune disease.

19. The method of claim 10, wherein the human has antibody-mediated transplant rejection.

20. The method of claim 10, wherein the human has rheumatoid arthritis.

21. The humanized antibody of claim 13, wherein the humanized antibody is a Fab fragment, a F(ab')2 fragment, a scFv, or a Fv.

22. A composition comprising:
a) the humanized antibody of claim 13; and
b) a pharmaceutically acceptable excipient.

23. The composition of claim 22, wherein the composition comprises one or more of a tonicity agent, a suspending agent, an emulsifying agent, a stabilizer, a preservative, a lyoprotectant, a surfactant, and a sugar.

24. A method comprising administering to a human a humanized antibody that specifically binds complement component C1s, wherein the antibody comprises a VH region comprising the amino acid sequence set forth in SEQ ID NO:14, a VL region comprising the amino acid sequence set forth in SEQ ID NO:22, and a heavy chain constant region of the isotype IgG4.

25. The method of claim 24, wherein the administering is selected from the group consisting of intravenously administering, intramuscularly administering, intrathecally administering, and subcutaneously administering.

26. The method of claim 24, wherein the human has cold agglutinin disease.

27. The method of claim 24, wherein the human has immunothrombocytopenic purpura (ITP).

28. The method of claim 24, wherein the human has bullous pemphigoid.

29. The method of claim 24, wherein the human has multifocal motor neuropathy.

30. The method of claim 24, wherein the human has an autoimmune disease.

31. The method of claim 24, wherein the human has antibody-mediated transplant rejection.

32. The method of claim 24, wherein the human has rheumatoid arthritis.

* * * * *

UNITED STATES PATENT AND TRADEMARK OFFICE
CERTIFICATE OF CORRECTION

PATENT NO. : 10,729,767 B2
APPLICATION NO. : 15/564904
DATED : August 4, 2020
INVENTOR(S) : Sandip Panicker et al.

Page 1 of 2

It is certified that error appears in the above-identified patent and that said Letters Patent is hereby corrected as shown below:

In the Claims

In Claim 1, at Column 69, Line 3: "Cls" should read --C1s--

In Claim 7, at Column 70, Line 41: "Cls" should read --C1s--

In Claim 11, at Column 71, Line 18: "Clq" should read --C1q--

In Claim 11, at Column 71, Line 29: "Guillain-Barr" should read --Guillain-Barré--

In Claim 13, at Column 72, Line 5: "wherein the antibody comprises a VH region comprising the amino acid sequence set forth in SEQ ID NO:14 and a VL region comprising the amino acid sequence set forth in SEQ ID NO:22, and a heavy chain constant region of the isotype IgG4." should read --wherein the antibody comprises a VH region comprising the amino acid sequence set forth in SEQ ID NO:14 and a VL region comprising the amino acid sequence set forth in SEQ ID NO:22.--

At Column 72, Lines 25-59: cancel the text beginning with "21. The humanized antibody" and ending "rheumatoid arthritis." and insert the following claims:

--21. The humanized antibody of claim 13, wherein the antibody further comprises a heavy chain constant region of the isotype IgG4.

22. The humanized antibody of claim 13, wherein the humanized antibody is a Fab fragment, a F(ab')2 fragment, a scFv, or a Fv.

23. A composition comprising:
a) the humanized antibody of claim 13; and
b) a pharmaceutically acceptable excipient.

Signed and Sealed this
Fifth Day of January, 2021

Andrei Iancu
*Director of the United States Patent and Trademark Office*

24. The composition of claim 23, wherein the composition comprises one or more of a tonicity agent, a suspending agent, an emulsifying agent, a stabilizer, a preservative, a lyoprotectant, a surfactant, and a sugar.

25. A method comprising administering to a human a humanized antibody that specifically binds complement component C1s, wherein the antibody comprises a VH region comprising the amino acid sequence set forth in SEQ ID NO:14 and a VL region comprising the amino acid sequence set forth in SEQ ID NO:22.

26. The method of claim 25, wherein the antibody further comprises a heavy chain constant region of the isotype IgG4.

27. The method of claim 25, wherein the administering is selected from the group consisting of intravenously administering, intramuscularly administering, intrathecally administering, and subcutaneously administering.

28. The method of claim 25, wherein the human has cold agglutinin disease.

29. The method of claim 25, wherein the human has immunothrombocytopenic purpura (ITP).

30. The method of claim 25, wherein the human has bullous pemphigoid.

31. The method of claim 25, wherein the human has multifocal motor neuropathy.

32. The method of claim 25, wherein the human has an autoimmune disease.

33. The method of claim 25, wherein the human has antibody-mediated transplant rejection.

34. The method of claim 25, wherein the human has rheumatoid arthritis.--